US012792145B2

(12) United States Patent
Yuan et al.

(10) Patent No.: US 12,792,145 B2
(45) Date of Patent: Nov. 10, 2026

(54) # METHODS AND SYSTEMS FOR DETERMINING FINGER JOINT ANGLES

(71) Applicant: SHENZHEN SHOKZ CO., LTD., Shenzhen (CN)

(72) Inventors: Yongshuai Yuan, Shenzhen (CN); Wenjun Deng, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 0 days.

(21) Appl. No.: 18/989,029

(22) Filed: Dec. 20, 2024

(65) Prior Publication Data

US 2025/0123686 A1 Apr. 17, 2025

Related U.S. Application Data

(63) Continuation of application No. PCT/CN2024/099237, filed on Jun. 14, 2024.

(30) Foreign Application Priority Data

Oct. 12, 2023 (WO) ................ PCT/CN2023/124295

(51) Int. Cl.
*G06F 3/01* (2006.01)
*A61B 5/00* (2006.01)
*A61B 5/107* (2006.01)

(52) U.S. Cl.
CPC ............ *G06F 3/014* (2013.01); *A61B 5/1071* (2013.01); *A61B 5/4538* (2013.01);
(Continued)

(58) Field of Classification Search
CPC ....... G06F 3/014; G06F 3/017; A61B 5/1071; A61B 5/4538; A61B 5/6806; A61B 2503/12; A61B 2562/0261
See application file for complete search history.

(56) References Cited

U.S. PATENT DOCUMENTS 6,701,296 B1 3/2004 Kramer et al.
8,941,392 B1 1/2015 Reese
(Continued)

FOREIGN PATENT DOCUMENTS

CN 105446485 A 3/2016
CN 107704087 A 2/2018
(Continued)

OTHER PUBLICATIONS

The Second Office Action in Chinese Application No. 202410769648.9 mailed on May 8, 2026, 17 pages.
(Continued)

*Primary Examiner* — Towfiq Elahi
(74) *Attorney, Agent, or Firm* — METIS IP LLC

(57) ABSTRACT

Embodiments of the present disclosure provide a method and a system for determining a finger joint angle. The method includes obtaining first sensor data relating to at least two target finger joints of a user, the first sensor data is obtained using at least two strain sensors, each of the strain sensors is arranged in a glove body worn by the user and located at one target finger joints, and the at least two target finger joints include at least two adjacent metacarpophalangeal joints of the user; obtaining a first mapping relationship, wherein the first mapping relationship reflects a relationship between sensor data corresponding to the at least two target finger joints and joint angles of the at least two target finger joints; and determining a first joint angle of each of the at least two target finger joints based on the first sensor data and the first mapping relationship.

18 Claims, 16 Drawing Sheets

(52) U.S. Cl.
CPC ........ *A61B 5/6806* (2013.01); *A61B 2503/12* (2013.01); *A61B 2562/0261* (2013.01)

(56) References Cited

U.S. PATENT DOCUMENTS

| | | | | |
|---|---|---|---|---|
| 10,823,546 | B1 | 11/2020 | Reese et al. | |
| 10,860,101 | B1 | 12/2020 | Menguc et al. | |
| 2007/0188180 | A1 | 8/2007 | Deangelis et al. | |
| 2008/0000009 | A1 | 1/2008 | Kogawa et al. | |
| 2009/0015270 | A1 | 1/2009 | Hayakawa et al. | |
| 2009/0293631 | A1 | 12/2009 | Radivojevic | |
| 2010/0259472 | A1 | 10/2010 | Radivojevic et al. | |
| 2014/0334083 | A1 | 11/2014 | Bailey | |
| 2015/0187325 | A1 | 7/2015 | Yeo et al. | |
| 2017/0059418 | A1 | 3/2017 | Keller et al. | |
| 2017/0371403 | A1 | 12/2017 | Wetzler et al. | |
| 2018/0160940 | A1 | 6/2018 | Kim et al. | |
| 2019/0250708 | A1 * | 8/2019 | Gupta | G02B 27/017 |
| 2021/0032974 | A1 | 2/2021 | Sihler et al. | |

FOREIGN PATENT DOCUMENTS

| | | | | | |
|---|---|---|---|---|---|
| CN | 108073283 | A | | 5/2018 | |
| CN | 108444436 | A | * | 8/2018 | G01C 1/00 |
| CN | 109407836 | A | | 3/2019 | |
| CN | 211986922 | U | | 11/2020 | |
| CN | 112230769 | A | | 1/2021 | |
| CN | 113065458 | A | | 7/2021 | |
| CN | 113705378 | A | | 11/2021 | |
| CN | 215120758 | U | | 12/2021 | |
| CN | 113975084 | A | | 1/2022 | |
| CN | 114913542 | A | | 8/2022 | |
| CN | 115016645 | A | | 9/2022 | |
| CN | 115112272 | A | | 9/2022 | |
| CN | 116007488 | A | | 4/2023 | |
| CN | 116543449 | A | | 8/2023 | |
| KR | 20090020839 | A | | 2/2009 | |
| WO | WO-2016060031 | A1 | * | 4/2016 | G01B 7/30 |
| WO | WO-2019173678 | A1 | * | 9/2019 | G06F 3/014 |

OTHER PUBLICATIONS

The Extended European Search Report in European Application No. 23955153.4 mailed on Mar. 27, 2026, 9 pages.

First Office Action in Chinese Application No. 202410769648.9 mailed on Nov. 7, 2025, 15 pages.

International Search Report in PCT/CN2024/099238 mailed on Aug. 27, 2024, 7 pages.

* cited by examiner

600

700

METHODS AND SYSTEMS FOR DETERMINING FINGER JOINT ANGLES

CROSS-REFERENCE TO RELATED APPLICATIONS

This application is a continuation of International Application No. PCT/CN2024/099237, filed on Jun. 14, 2024, which claims priority to International Application No. PCT/CN2023/124295, filed on Oct. 12, 2023, the entire contents of which are incorporated herein by reference.

TECHNICAL FIELD

The present disclosure relates to the field of data processing, and in particular, to methods and systems for determining finger joint angles.

BACKGROUND

As augmented reality/virtual reality (AR/VR) technology matures and the metaverse concept rises, intelligent electronic devices have put forward higher requirements for advanced human-computer interaction technology. Flexible sensors may be conveniently integrated into wearable devices such as smart garments, smart gloves, etc., enabling accurate recognition and restoration of human body motions. This makes them one of the essential underlying technologies of the metaverse, receiving extensive attention and research. To realize accurate recognition and reduction of hand movements, it is necessary to capture the motions of the hand, especially the fingers, in multiple degrees of freedom through sensors, and then determine the angles of the finger joints (bending and/or swinging angles) based on the captured sensor data.

To capture the multi-dimensional motion of the finger, inertial sensors (e.g., nine-axis sensors, gyroscopes) are generally arranged at non-joint positions on the finger. The bending of the finger is deduced by measuring the morphology (e.g., the spatial position) of various positions, which requires multiple gyroscopes, resulting in high costs. Alternatively, single-degree-of-freedom strain sensors may be arranged at the joint, with gyroscopes arranged at other positions. The combination of these sensors may determine the bending of the finger. However, since fingers can move in multiple degrees of freedom (e.g., the metacarpophalangcal joint may have at least two degrees of freedom of motion, such as bending and swinging), the measurements and calculations of the single-degree-of-freedom strain sensor arranged at the joint are not sufficiently accurate.

SUMMARY

One embodiment of the present disclosure provides a method of determining a finger joint angle. The method may include obtaining first sensor data relating to at least two target finger joints of a user, the first sensor data being obtained using at least two strain sensors, each of the strain sensors being arranged in a glove body worn by the user and located at one of the at least two target finger joints, and the at least two target finger joints including at least two adjacent metacarpophalangeal joints of the user; obtaining a first mapping relationship, the first mapping relationship reflecting a relationship between sensor data corresponding to the at least two target finger joints and joint angles of the at least two target finger joints; and determining a first joint angle of each of the at least two target finger joints based on the first sensor data and the first mapping relationship.

In some embodiments, the at least two target finger joints may include a portion of finger joints of the user.

In some embodiments, the at least two target finger joints may include all metacarpophalangeal joints and all proximal interphalangeal joints of the user.

In some embodiments, the at least two metacarpophalangeal joints may include metacarpophalangeal joints of at least one finger of the index finger, the middle finger, or the ring finger of the user and two adjacent fingers on two sides of the at least one finger.

In some embodiments, the at least two metacarpophalangeal joints may include metacarpophalangeal joints of at least one finger of the thumb or the pinky thumb of the user and one adjacent finger of the at least one finger.

In some embodiments, the at least two strain sensors may include at least two first strain sensors disposed at the at least two metacarpophalangeal joints, each of the at least two first strain sensors being configured to measure a deformation of a corresponding metacarpophalangeal joint in two degrees of freedom.

In some embodiments, the at least two target finger joints may further include at least two proximal interphalangeal joints corresponding to the at least two metacarpophalangeal joints.

In some embodiments, the at least two strain sensors may include at least two second strain sensors disposed at the at least two proximal interphalangeal joints, each of the second strain sensors being configured to measure a deformation of a corresponding proximal interphalangeal joint in a single degree of freedom.

In some embodiments, the method may further include for each proximal interphalangeal joint among the at least two proximal interphalangeal joints, determining, based on a second mapping relationship and the first joint angle of the proximal interphalangeal joint, a second joint angle of a distal interphalangeal joint corresponding to the proximal interphalangcal joint. The second mapping relationship may reflect a relationship between a joint angle of the proximal interphalangcal joint and a joint angle of the distal interphalangeal joint.

In some embodiments, the second mapping relationship may be represented by a mapping function or a trained machine learning model.

In some embodiments, the first sensor data may include decoupling data of the at least two target finger joints, the decoupling data being determined based on raw data collected by the at least two strain sensors.

In some embodiments, the first sensor data may include raw data collected by the at least two strain sensors.

In some embodiments, the determining a first joint angle of each of the at least two target finger joints based on the first sensor data and the first mapping relationship may include obtaining reference sensor data relating to the at least two target finger joints of the user, the reference sensor data being collected using the at least two strain sensors when the user makes a preset gesture; obtaining a corrected mapping relationship corresponding to the user by correcting the first mapping relationship based on the reference sensor data; and determining the first joint angle of each of the at least two target finger joints based on the corrected mapping relationship and the first sensor data.

In some embodiments, the first mapping relationship may be represented by a trained machine learning model, and the first mapping relationship may be corrected based on a migration learning algorithm.

In some embodiments, the at least two target finger joints may only include at least two adjacent metacarpophalangeal joints of the user, and the method may further include obtaining second sensor data relating to at least two proximal interphalangeal joints corresponding to the at least two adjacent metacarpophalangeal joints, the second sensor data being obtained using at least two second strain sensors, each of the second strain sensors being arranged in the glove body worn by the user and located at one of the at least two proximal interphalangcal joints; and determining a third joint angle of each of the at least two proximal interphalangeal joints based on the second sensor data, the first joint angle of each of the at least two target finger joints, and a third mapping relationship, the third mapping relationship reflecting a relationship between joint angles of the at least two adjacent metacarpophalangeal joints, sensor data relating to the at least two proximal interphalangeal joints, and joint angles of the at least two proximal interphalangcal joints.

In some embodiments, the glove body may include fabric wrapped around each finger of the user and fabric disposed between adjacent fingers, an elastic modulus of the fabric disposed between the adjacent fingers is less than an clastic modulus of the fabric wrapped around each finger. The method may further include obtaining a value of a characteristic parameter of the fabric disposed between the adjacent fingers, the characteristic parameter including at least one of an elastic coefficient, a transverse dimension, or a resilience coefficient. The first mapping relationship may further reflect a relationship between the characteristic parameter, the sensor data corresponding to the at least two target finger joints, and the joint angles of the at least two target finger joints. The first joint angle of each of the at least two target finger joints may be further determined based on the value of the characteristic parameter.

In some embodiments, the glove body may include a position sensor arranged at each of the at least two target finger joints. The method may further include determining distance information between the at least two strain sensors based on position data collected by the position sensor arranged at each of the at least two target finger joints. The first mapping relationship further may reflect a relationship between a distance between the at least two strain sensors, the sensor data corresponding to the at least two target finger joints, and the joint angles of the at least two target finger joints. The first joint angle of each of the at least two target finger joints may be further determined based on the distance information.

In some embodiments, the first mapping relationship may be determined by obtaining a plurality of data samples and determining, based on the plurality of data samples, the first mapping relationship based on a data fitting algorithm or a machine learning algorithm. Each of the plurality of data samples may correspond to a sample user making a sample gesture and include sample sensor data relating to at least two sample finger joints of the sample user and sample joint angles of the at least two sample finger joints. The sample sensor data may be collected using at least two sample sensors arranged in a sample glove body worn by the sample user, and the at least two sample finger joints may be of the same type as the at least two target finger joints.

In some embodiments, the at least two sample finger joints may include a portion of finger joints of the sample user.

In some embodiments, the at least two sample finger joints may include all metacarpophalangeal joints and all proximal interphalangeal joints of the sample user.

In some embodiments, at least one data sample of the plurality of data samples may be obtained by: for each data sample of the at least one data sample, obtaining sensor data collected by the at least two sample sensors when the sample user makes the sample gesture as the sample sensor data of the data sample, obtaining an optical image of a hand captured when the sample user makes the sample gesture, and determining the sample joint angles of the data sample based on the optical image of the hand.

In some embodiments, at least one of the plurality of data samples may be obtained by: for each data sample of at least one data sample, controlling a terminal device to display a hand model corresponding to the sample gesture to the sample user corresponding to the data sample, obtaining sensor data collected by the at least two sample sensors when the sample user imitates the sample gesture as the sample sensor data of the data sample, and determining the sample joint angles of the data sample based on the hand model.

In some embodiments, the obtaining sensor data collected by the at least two sample sensors when the sample user imitates the sample gesture as the sample sensor data of the data sample may include obtaining an optical image of a hand of the sample user captured when the sample user imitates the sample gesture; determining, based on the optical image of the hand, whether a gesture of the sample user is the sample gesture; and in response to determining that the gesture of the sample user is the sample gesture, obtaining sensor data currently collected by the at least two sample sensors as the sample sensor data, or in response to determining that the gesture of the sample user is not the sample gesture, controlling the terminal device to display an alert message for adjusting the gesture to the sample user.

In some embodiments, the first mapping relationship may be represented by a mapping function, and the glove body may include a position sensor arranged at each of the at least two target finger joints. The determining a first joint angle of each of the at least two target finger joints based on the first sensor data and the first mapping relationship may include determining distance information between the at least two strain sensors based on position data captured by the position sensor arranged at each of the at least two target finger joints; obtaining a corrected mapping function corresponding to the user by correcting the mapping function based on the distance information; and determining the first joint angle of each of the at least two target finger joints based on the corrected mapping function and the first sensor data.

One embodiment of the present disclosure provides a system for determining a finger joint angle. The system may include at least one storage medium storing a set of instructions and at least one processor in communication with the at least one storage medium. The at least one processor, when executing the set of instructions, may cause the system to perform the method for determining the finger joint angle described in the present disclosure.

One embodiment of the present disclosure provides a non-transitory computer-readable medium storing executable instructions that, when executed by at least one processor, cause the at least one processor to perform the method for determining the finger joint angle described in the present disclosure.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

DETAILED DESCRIPTION

Figure 1:
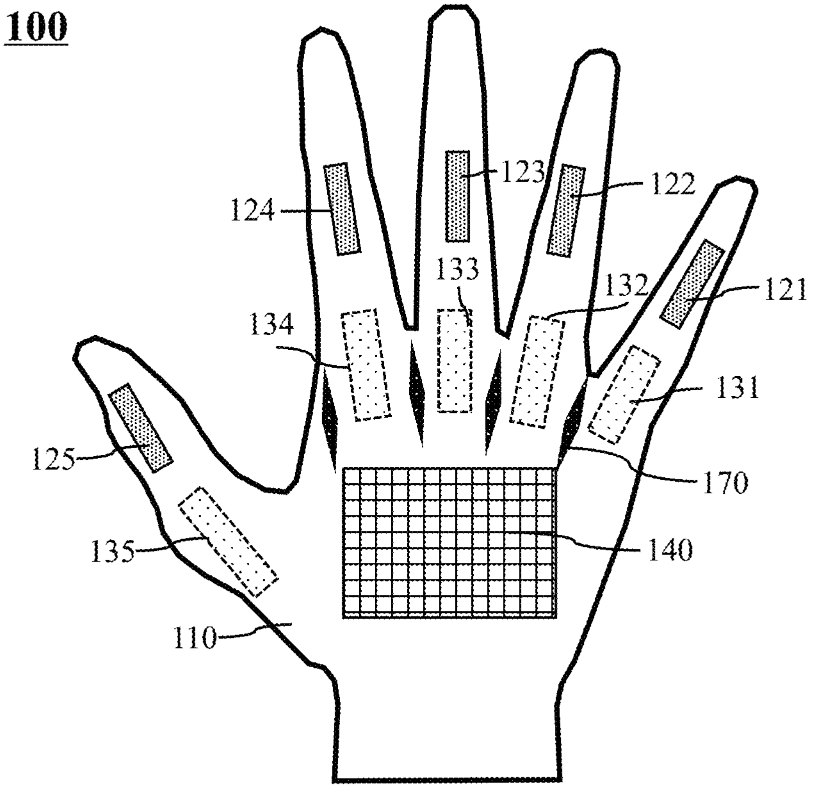
FIG. 1 is a schematic diagram illustrating an exemplary glove system according to some embodiments of the present disclosure.

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that “system,” “device,” “unit,” and/or “module” as used herein is a manner used to distinguish different components, elements, parts, sections, or assemblies at different levels. However, if other words serve the same purpose, the words may be replaced by other expressions.

As shown in the present disclosure and claims, the words “one,” “a,” “a kind,” and/or “the” are not especially singular but may include the plural unless the context expressly suggests otherwise. In general, the terms “comprise,” “comprises,” “comprising,” “include,” “includes,” and/or “including” merely prompt to include operations and elements that have been clearly identified, and these operations and elements do not constitute an exclusive listing. The methods or devices may also include other operations or elements.

The flowcharts used in the present disclosure illustrate operations that systems implement according to some embodiments of the present disclosure. It should be understood that the previous or subsequent operations may not be accurately implemented in order. Instead, each step may be processed in reverse order or simultaneously. Meanwhile, other operations may also be added to these processes, or a certain step or several steps may be removed from these processes.

In order to achieve precise recognition and restoration of hand movements, it is necessary to collect the motions of the hand, especially the fingers, in a plurality of degrees of freedom. For example, a glove system may capture the hand movements (including finger movements) of the user. FIG. 1 is a schematic diagram illustrating an exemplary glove system according to some embodiments of the present disclosure. As shown in FIG. 1, a glove system 100 includes a glove body 110, a plurality of strain sensors (e.g., first strain sensors 131-135 and second strain sensors 121-125), an elastic fabric structure 170, and a processor 140. The plurality of strain sensors may be distributed at different positions on the glove body 110.

The glove system 100 refers to a system configured to capture the hand movements (including finger movements) of a user. The glove system 100 may recognize hand movements by one or more devices including, for example, a movement capture glove, a sign language glove, a virtual reality (VR) glove, a force feedback glove, a haptic feedback glove, or the like.

The glove body 110 refers to a wearable member configured to fit to the hand. In some embodiments, to facilitate fitting the glove body 110 with hand joints (e.g., interphalangeal joints, metacarpophalangeal joints, wrist joints, etc.), the glove body 110 has a structure adapted to the shape of the hand and extending along the hand joints. In some embodiments, the glove body 110 may be a flexible fabric and is prone to deform (e.g., bend) following the finger when subjected to an external force. In some embodiments, the glove body 110 may provide support for the strain sensors, facilitating the arrangement of the strain sensors. For example, the glove body 110 may include one or more layers of flexible structure (e.g., flexible fabric). The strain sensors may be fixed to the surface of a layer of flexible structure by taping, pressing, or stitching.

In some embodiments, the strain sensor may be configured to collect sensor data from the finger. When the user wearing the glove body 110 generates finger movement, the regions corresponding to the fingers on the glove body 110 are deformed. The strain sensors may convert deformation information (e.g., a deformation direction, a deformation size, etc.) at the joints of the fingers into an electrical signal, and the electrical signal generated by the strain sensors may reflect posture data at the regions corresponding to the fingers. In some embodiments, the strain sensors may include, but are not limited to, a capacitance strain sensor, an inductive sensor, a resistive sensor, a fiber optic sensor, or the like.

Figure 2:
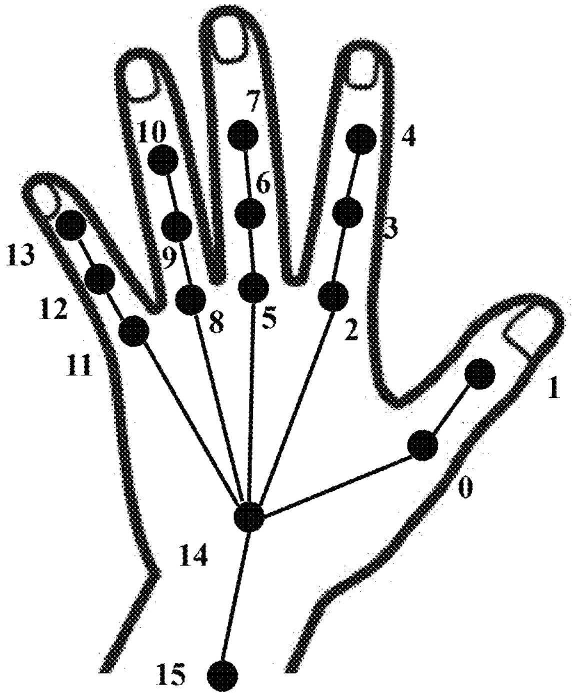
FIG. 2 is a schematic diagram illustrating joint positions of a hand of a user according to some embodiments of the present disclosure.

In some embodiments, the strain sensors may be arranged at the knuckles of the glove body 110. FIG. 2 is a schematic diagram illustrating the joint positions of a hand of a user according to some embodiments of the present disclosure. The knuckles of the hand may include metacarpophalangeal joints at positions 0, 2, 5, 8, 11 and interphalangeal joints at positions 1, 3, 6, 9, 12, 4, 7, 10, 13. The plurality of strain sensors may include first strain sensors (e.g., first strain sensors 131, 132, 133, 134, and 135) disposed at the metacarpophalangeal joints 0, 2, 5, 8, 11, respectively. The first strain sensors may be configured to measure the deformation of the metacarpophalangeal joints in two degrees of freedom. The plurality of strain sensors may also include second strain sensors (e.g., second strain sensors 121, 122, 123, 124, and 125) disposed at the interphalangeal joints 1, 3, 6, 9, 12, 4, 7, 10, 13, respectively. The second strain sensors may be configured to measure the deformation of the interphalangeal joints in a single degree of freedom. In some embodiments, the second strain sensors include a single-degree-of-freedom sensor, such as a single-axis sensor (e.g., an inductive bending sensor, a resistive bending sensor, or a capacitance stretching sensor). The first strain sensors include a multi-degree-of-freedom sensor, such as a multi-axis sensor (e.g., a capacitance multi-axis motion sensor).

The degree of freedom described in the present disclosure refers to a dimension in which an object is capable of moving. To illustrate the degree of freedom of the movement of the hand, a three-dimensional coordinate system is established for the movement of the hand, for example, a three-dimensional coordinate system illustrated in FIG. 3. In this coordinate system, one metacarpophalangeal joint is taken as the origin, an extension direction of the fingers is taken as a Y-axis, and a direction perpendicular to a hand plane is taken as a Z-axis. The hand plane refers to the fitting plane of the palm. For example, when the palm is pressed against the tabletop, the tabletop, or a plane that passes through the hand and is parallel to the tabletop, may be the hand plane. The three-dimensional coordinate system may be used to describe the degree of freedom of the movement of the hand. Specifically, in the three-dimensional coordinate system shown in FIG. 3, the rotation of the hand about the X-axis is defined as bending, the rotation of the hand about the Z-axis is defined as swinging, and the rotation of the hand about the Y-axis is defined as turning. The interphalangcal joints can only bend and turn. In other words, the deformation of the interphalangeal joints corresponds to only one degree of freedom, bending. The metacarpophalangcal joints can bend, swing, and turn. In other words, the deformation of the metacarpophalangcal joints corresponds to the two degrees of freedom, bending and swinging. In such cases, when any of the interphalangcal joints undergo a bending movement, the second strain sensors may measure the deformation of the glove body 110 that occurs at the corresponding interphalangeal joint. When any of the metacarpophalangeal joints undergo a bending or swinging movement, the first strain sensors may measure the deformation of the glove body 110 at the corresponding metacarpophalangcal joint.

Continuing to refer to FIG. 2, interphalangeal joints 4, 7, 10, and 13 are distal interphalangeal joints relatively remote from the palm, and interphalangeal joints 1, 3, 6, 9, and 12 are proximal interphalangeal joints relatively close to the palm. In some embodiments, the movement of a distal interphalangeal joint is manifested as a follow-through to the preceding joint (the proximal interphalangeal joint), which in general does not bend independently, but instead bends with the proximal interphalangeal joint. Therefore, instead of arranging the second strain sensors separately at the distal interphalangeal joints, the second strain sensors may be arranged only at the proximal interphalangeal joints. In some embodiments, the deformation data at the distal interphalangeal joints may be generated by mapping the deformation data corresponding to the proximal interphalangeal joints. Thus, the glove system 100 may collect deformation data at at least five proximal interphalangeal joints at a single degree of freedom via the plurality of second strain sensors and collect deformation data at five metacarpophalangeal joints at two degrees of freedom via the plurality of first strain sensors. In total, the plurality of second strain sensors and the plurality of first strain sensors together provide deformation data for at least 15 degrees of freedom on the user's fingers, thereby determining the posture data of the finger.

Typically, in order to capture the multi-degree-of-freedom movement of the finger, it is necessary to arrange gyroscopes at non-joint positions on the finger and deduce the bending of the finger by measuring the morphology of the finger at various positions. Alternatively, single-degree-of-freedom strain sensors (e.g., a second strain sensor) are arranged at the joints of the finger, with the gyroscopes arranged at the non-joint positions of the finger. The measurement results of the two are combined to calculate the bending of the finger. Some embodiments of the present disclosure control the cost of the product, reduce the cost of subsequent data processing, and ensure the accuracy of the measurements by using a combination of dual-degree-of-freedom strain sensors (e.g., the first strain sensors) and single-degree-of-freedom strain sensors (e.g., the second strain sensors). More descriptions regarding the first strain sensors and the second strain sensors may be found in FIG. 7 and related descriptions thereof.

In some embodiments, the glove system 100 further includes elastic fabric structures 170 provided between adjacent finger roots (near the metacarpophalangeal joints) for reducing or avoiding fabric pulling at adjacent finger roots during finger movement. The data collected by the strain sensors at adjacent metacarpophalangeal joints may interfere with each other due to the possibility that the flexible fabric between adjacent finger roots may pull against each other under external force. In some embodiments, the flexible fabric structure 170 may be a slit structure or a pleated structure including a structure that reduces or avoids pulling between the fabrics on the adjacent fingers, such that an elastic modulus of the fabric between the adjacent fingers is less than an clastic modulus of the fabric on each finger. Therefore, the effect of mutual interference between the first strain sensors arranged at the roots of different fingers is reduced, ensuring that the data captured by each of the first strain sensors may accurately reflect the deformation at the corresponding position.

The glove system 100 may also include a processor 140. The processor 140 is configured to receive and process data collected by the plurality of strain sensors (including the plurality of first strain sensors and the plurality of second strain sensors). For example, the processor 140 may obtain deformation data from the strain sensors and analyze and process the deformation data, e.g., by calculating the deformation magnitude and deformation angle of each joint of the finger through a mapping relationship (e.g., a mapping function or a trained machine learning model). In some embodiments, the processor 140 may directly process data collected by the plurality of strain sensors or receive data collected by the plurality of strain sensors and transmit the data to an external device for data processing. In some embodiments, the processor 140 may perform a corresponding function, such as gesture reproduction, voice announcement, gesture manipulation, or the like, based on the processing results of data. In some embodiments, the processor 140 may interact with an external processing device based on the processing results of the data. The external processing device includes a computer, a cell phone, a VR device, and other uplinks. Interactions may include, for example, controlling the on/off switching of an external device, volume adjustments, program progression of an external device (e.g., controlling the movement of a game character), fitness feedback, or the like.

When using dual-degree-of-freedom strain sensors to capture hand movement, there is coupling between a plurality of finger joints. If the movement or deformation (e.g., bending, swinging) of one knuckle leads to a linked change in the sensor data of the other knuckle, the two knuckles may be referred to as being coupled. For example, when one finger joint bends, it pulls the fabric of the adjacent finger joint, causing the fabric of the adjacent finger joint to deform, resulting in a change in the sensor data corresponding to the adjacent finger joint (e.g., a change in the sensor data corresponding to the swinging degree of freedom, or a change in the sensor data corresponding to the bending degree of freedom caused by the change in the swinging). Therefore, the coupling between different finger joints needs to be taken into account when determining the finger joint angle. More descriptions regarding determining the finger joint angle may be found in FIG. 6 and related descriptions thereof.

Figure 4:
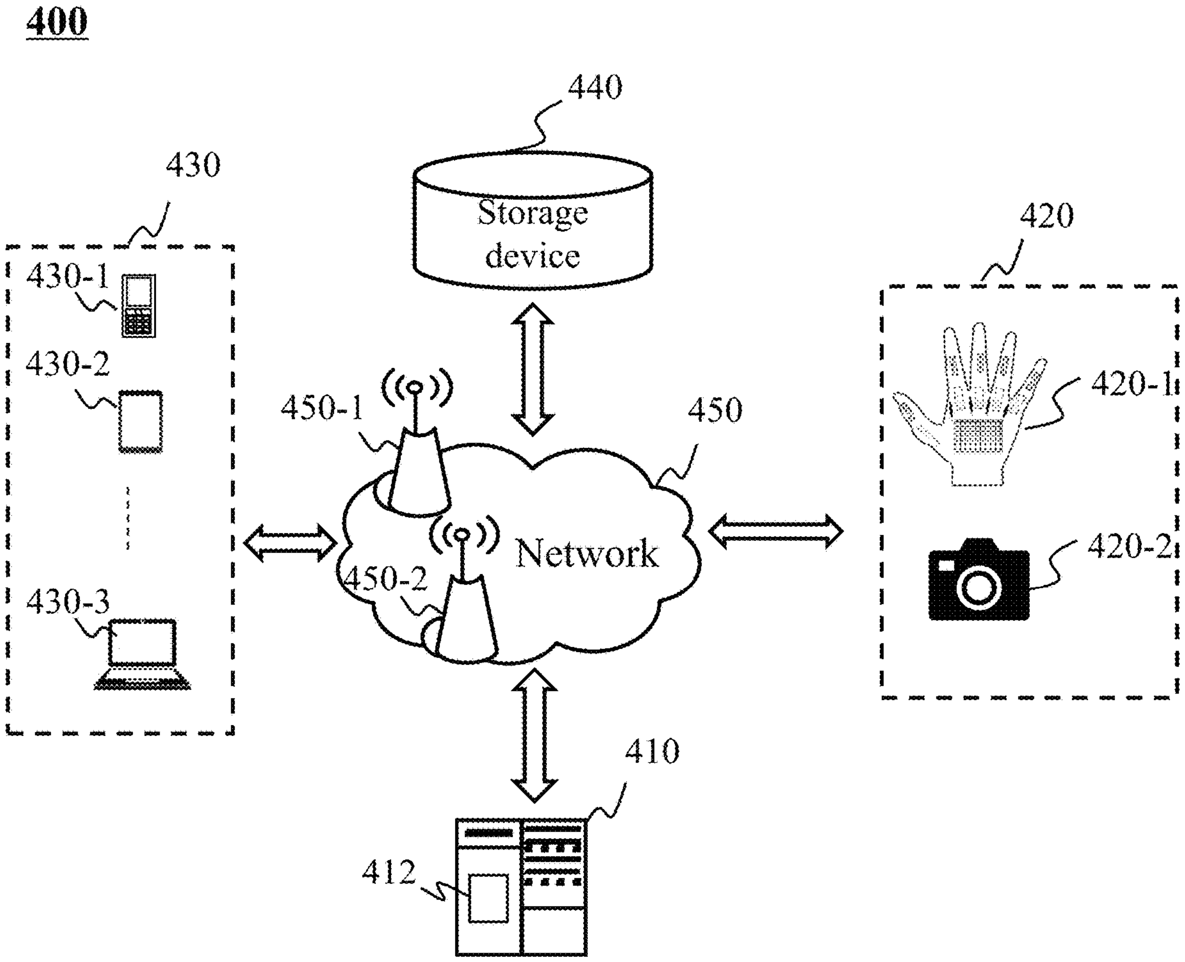
FIG. 4 is a schematic diagram illustrating an exemplary system for determining a finger joint angle according to some embodiments of the present disclosure.

FIG. 4 is a schematic diagram illustrating an exemplary system for determining a finger joint angle according to some embodiments of the present disclosure. The system 400 shown in embodiments of the present disclosure may be applied in various software, systems, platforms, and devices. In some embodiments, the system 400 may be used to determine a correspondence relationship between sample sensor data and a sample finger joint angle. In some embodiments, the system 400 may be used to determine a joint angle of a target finger joint. For example, the system may determine a mapping relationship between sensor data and a finger joint angle based on the correspondence relationship between the sample sensor data and the joint angle of the sample finger joint and determine the joint angle of the target finger joint.

As shown in FIG. 4, the system 400 may include a processing device 410, an acquisition device 420, a terminal 430, a storage device 440, and a network 450.

In some embodiments, the processing device 410 may process data and/or information obtained from other devices or system components. The processing device 410 may execute program instructions based on the data, information, and/or processing results to perform one or more of the functions described herein. For example, the processing device 410 may obtain the first sensor data relating to at least two target finger joints of the user from the acquisition device 420, where the first sensor data is acquired using at least two strain sensors. As another example, the processing device 410 may obtain a first mapping relationship, the first mapping relationship reflecting a relationship between sensor data corresponding to the at least two target finger joints and joint angles of the at least two target finger joints, and thus determine a first joint angle of each of the at least two target finger joints based on the first sensor data and the first mapping relationship. As yet another example, the processing device 410 may obtain an optical image of the hand of the user from the acquisition device 420 and determine the joint angles of two finger joints of the user at least based on the optical image.

In some embodiments, the processing device 410 may be a single processing device or a group of processing devices, such as a server or a server group. The group of processing devices may be centralized or distributed (e.g., the processing device 410 may be a distributed system). In some embodiments, the processing device 410 may be local or remote. For example, the processing device 410 may be a processor 140 on a glove system. As another example, the processing device 410 may access information and/or data in the acquisition device 420, the terminal 430, and the storage device 440 via the network 450. As yet another example, the processing device 410 may be directly connected to the acquisition device 420, the terminal 430, and the storage device 440 to access the stored information and/or data. In some embodiments, the processing device 410 may be implemented on a cloud platform.

In some embodiments, the processing device 410 may include a processing engine 412. The processing engine 412 may process data and/or information related to sensor data to perform one or more of the methods or functions described herein. For example, the processing engine 412 may process a plurality of sets of sample sensor data and corresponding optical images of the hand, and determine a correspondence relationship between the sample sensor data and the sample joint angle corresponding to the sample sensor data. As another example, the processing engine 412 may obtain the first sensor data relating to the at least two target finger joints of the user and process the first sensor data to determine the first joint angle of each of the at least two target finger joints.

In some embodiments, the processing engine 412 may include one or more processing engines (e.g., a single-chip processing engine or a multi-chip processor). In some embodiments, the processing engine 412 may be integrated into the acquisition device 420 or the terminal 430.

In some embodiments, the acquisition device 410 may be configured to capture posture data of the finger of the user and/or deformation information indicating movement of the finger joint. For example, the acquisition device 420 may include a first acquisition device 420-1 for capturing the first sensor data relating to the at least two target finger joints of the user. In some embodiments, the first acquisition device 420-1 may be one or a combination of an acquisition device such as a movement capture glove, a sign language glove, a VR glove, a force feedback glove, a haptic feedback glove, or the like. In some embodiments, the first acquisition device 420-1 may be the glove system 100 or a portion of the glove system 100. Descriptions regarding the glove system 100 may be found in FIG. 1 and related descriptions thereof. As another example, the acquisition device 420 may include a second acquisition device 420-2 for capturing an optical image of the hand of the user. In some embodiments, the second capture device 420-2 may be a device for capturing an optical image, e.g., a camera, a camcorder, etc.

In some embodiments, the acquisition device 420 may transmit information and/or data with the processing device 410, the terminal 430, and the storage device 440 via the network 450. In some embodiments, the acquisition device 420 may be directly connected to the processing device 410 or the storage device 440 to transmit information and/or data. For example, the acquisition device 420 (e.g., the first acquisition device 420-1) and the processing device 410 may be different portions on the same electronic device (e.g., a glove system) and are connected by metal wires.

In some embodiments, the terminal 430 may be a terminal used by the user or other entity. For example, the terminal 430 may be a terminal hosting the above-described acquisition device 420. As another example, the terminal 430 may be a terminal that communicates with any one or more components of the acquisition device 420 or the system 400 via the network 450. In some embodiments, the acquisition device 420 may be part of the terminal 430.

In some embodiments, the terminal 430 may include a mobile device 430-1, a tablet 430-2, a laptop 430-3, etc., or any combination thereof. In some embodiments, the mobile device 430-1 may include a smart home device, a wearable device, a smart mobile device, a VR device, an augmented reality (AR) device, etc., or any combination thereof. In some embodiments, the smart home device may include a smart lighting device, a smart appliance control device, a smart surveillance device, a smart TV, a smart camera, a walkie-talkie, or the like, or any combination thereof. In some embodiments, the wearable device may include a smart bracelet, smart footwear, smart glasses, a smart helmet, a smart watch, a smart headset, a smart garment, a smart backpack, a smart accessory, or the like, or any combination thereof. In some embodiments, the smart mobile device may include a smart phone, a personal digital assistant (PDA), a gaming device, a navigation device, a point of sale (POS), or the like, or any combination thereof. In some embodiments, the VR device and/or the AR device may include a VR helmet, VR glasses, a VR eyepatch, an augmented VR helmet, AR glasses, AR eyepatch, etc., or any combination thereof.

In some embodiments, the terminal 430 may obtain/receive data relating to other components in the system 400. For example, the terminal 430 may obtain the first sensor data relating to at least two target finger joints of the user captured by the acquisition device 420. As another example, the terminal 430 may obtain/receive the first joint angle of each of the at least two target finger joints determined by the processing device 410 based on the first sensor data. As yet another example, the terminal device may be used to present information and/or data (e.g., the optical image of the hand, a hand model, etc.) relating to the system 400 to the user and receive feedback from the user.

The storage device 440 may store data and/or information obtained from other devices or system components. In some embodiments, the storage device 440 may store data obtained from the acquisition device 420 or data obtained from processing by the processing device 410. For example, the storage device 440 may store the correspondence relationship and/or the mapping relationship between the sensor data and the joint angles. As another example, the storage device 440 may store the first sensor data captured by the acquisition device 420 and store the first joint angle of the target finger joint obtained after processing by the processing device 410. In some embodiments, the storage device 440 may also store data and/or instructions used by the processing device 410 to execute or accomplish the exemplary method described in the present disclosure. In some embodiments, the storage device 440 may include mass memory, removable memory, volatile read-write memory, read-only memory (ROM), or the like, or any combination thereof. In some embodiments, the storage device 440 may be implemented on a cloud platform.

In some embodiments, the storage device 440 may be connected to the network 450 to communicate with one or more components (e.g., the processing device 410, the acquisition device 420, the terminal 430) in the system 400. One or more components of the system 400 may access data or instructions stored in the storage device 440 via the network 450. The network 450 may facilitate the exchange of information and/or data. In some embodiments, one or more components of the system 400 (e.g., the processing device 410, the acquisition device 420, the terminal 430, and the storage device 440) may send/receive information and/or data to/from the other components of the system 400 via the network 450. For example, the processing device 410 may obtain the first sensor data or the deformation information of the movement of the finger joints from the acquisition device 420 or the storage device 440 via the network 450. The terminal 430 may obtain any one or more of the first sensor data, the first joint angle of the target finger joint, or the like, from the processing device 410 or the storage device 440 via the network 450. In some embodiments, the network 450 may be any form of wired or wireless network, or any combination thereof. In some embodiments, the system 400 may include one or more network access points. For example, the system 400 may include a wired or wireless network access point, such as a base station and/or a wireless access point 450-1, 450-2, . . . , and one or a plurality of components of the system 400 may be connected to the network 450 to exchange data and/or information.

The above description is Merely by way of example only, and actual application scenarios may vary. It should be noted that the system 400 is provided Merely by way of example only and is not intended to limit the scope of the present disclosure. For a person of ordinary skill in the art, a variety of modifications or variations may be made according to the description in the present disclosure. However, these changes and modifications do not depart from the scope of this application.

Figure 5A:
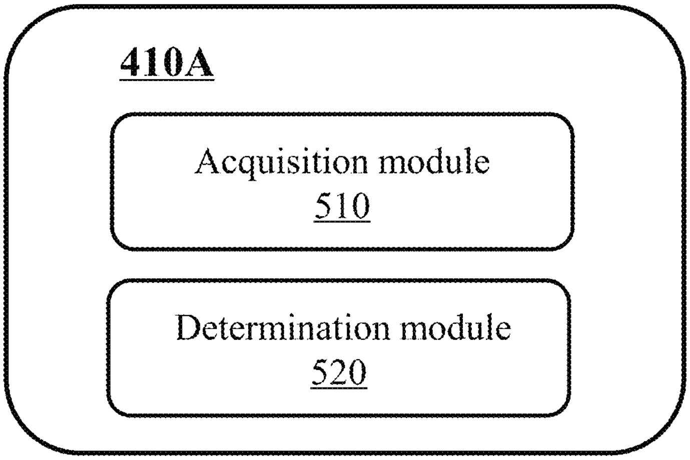
FIG. 5A is a block diagram illustrating an exemplary processing device 410A according to some embodiments of the present disclosure.
Figure 5B:
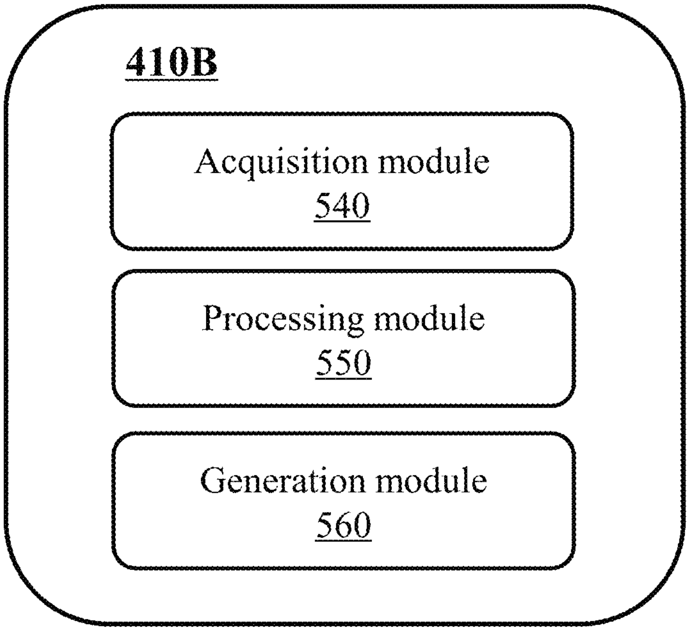
FIG. 5B is a block diagram illustrating an exemplary processing device 410B according to some embodiments of the present disclosure.

FIG. 5A and FIG. 5B are exemplary block diagrams illustrating processing devices 410A and 410B according to some embodiments of the present disclosure. The processing device 410A and the processing device 410B may be the processing devices 410 described in FIG. 4. In some embodiments, the processing device 410A may be configured to determine a finger joint angle based on sensor data and a mapping relationship. The processing device 410B may be configured to determine a mapping relationship between the sensor data and finger joint angles. In some embodiments, processing device 410A and the processing device 410B may be implemented on the same or different devices.

As shown in FIG. 5A, the processing device 410A may include an acquisition module 510 and a determination module 520.

The acquisition module 510 may be configured to obtain the first sensor data relating to at least two target finger joints of a user, and the first sensor data is obtained using at least two strain sensors. Each of the at least two strain sensors is arranged in a glove body worn by the user and located at one of the at least two target finger joints. The at least two target finger joints may include at least two adjacent metacarpophalangeal joints of the user. In some embodiments, the acquisition module 510 may obtain the first sensor data from the glove system or the storage device.

The acquisition module 510 may also be configured to obtain a first mapping relationship, the first mapping relationship reflecting a relationship between sensor data corresponding to the at least two target finger joints and joint angles of the at least two target finger joints. The first mapping relationship may be represented in the form of a mapping function, a machine learning model, or the like. The first mapping relationship may be determined by the processing device 410A or the processing device 410B based on a plurality of data samples. More descriptions regarding generating the first mapping relationship may be found in FIG. 19 and its related descriptions.

The determination module 520 may be configured to determine a first joint angle of each of the at least two target finger joints based on the first sensor data and the first mapping relationship. In some embodiments, the determination module 520 may input the first sensor data into the first mapping relationship and output the first joint angle of the target finger joint after processing the first mapping relationship.

As shown in FIG. 5B, the processing device 410B may include an acquisition module 540, a processing module 550, and a generation module 560.

The acquisition module 540 may be configured to obtain a plurality of sets of sample sensor data, each set of the plurality of sets of sample sensor data relating to at least two sample finger joints of a sample user and obtained using at least two sample strain sensors at a target moment. Each of the at least two sample strain sensors is arranged in a sample glove body worn by the sample user and located at one of the at least two sample finger joints, and the at least two sample finger joints include at least two adjacent metacarpophalangeal joints of the sample user.

The processing module 550 may be configured to determine, for each set of the plurality of sets of sample sensor data, sample joint angles of at least two sample finger joints of the corresponding sample user. In some embodiments, the processing module 550 may obtain, for each set of the plurality of sets of sample sensor data, an optical image of the hand of the sample user corresponding to the set of sample sensor data captured at the target moment, and determine the sample joint angles of at least two sample finger joints of the corresponding sample user based on the optical image of the hand. For example, the processing module 550 may determine a hand model based on the optical image of the hand and determine the sample joint angles based on the hand model.

The generation module 560 may be configured to determine a correspondence relationship between each set of the plurality of sets of sample sensor data and sample joint angles corresponding to the set of sample sensor data. In some embodiments, the generation module 560 may also be configured to determine a mapping relationship (i.e., a first mapping relationship) between the sensor data and the joint angles corresponding to the at least two sample finger joints based on the correspondence relationship. For example, the generation module 560 may determine the mapping relationship based on the correspondence relationship using a data fitting algorithm or a machine learning algorithm.

In some embodiments, the processing device 410A and/or the processing device 410B may share two or more modules, and any of the modules may be divided into two or more units. For example, the processing device 410A and the processing device 410B may share the same acquisition module, i.e., the acquisition module 510 and the acquisition module 540 are the same module. In some embodiments, the processing device 410A and/or the processing device 410B may include one or more additional modules, such as a storage module (not shown) for storing data. In some embodiments, the processing device 410A and the processing device 410B may be integrated into a single processing device 410.

The methods disclosed in the present disclosure may be stored in a storage device (e.g., the storage device 440 or a storage unit of the processing device 410) in the form of a program or instructions, which may be implemented when the processing device 410, the processing engine 412, or the module shown in FIG. 5A or FIG. 5B executes the program or instructions. In some embodiments, the methods disclosed in the present disclosure may include one or more additional operations/steps, and/or omit one or more operations/steps. Additionally, the order of the individual operations/steps in the method is not limiting.

Figure 6:
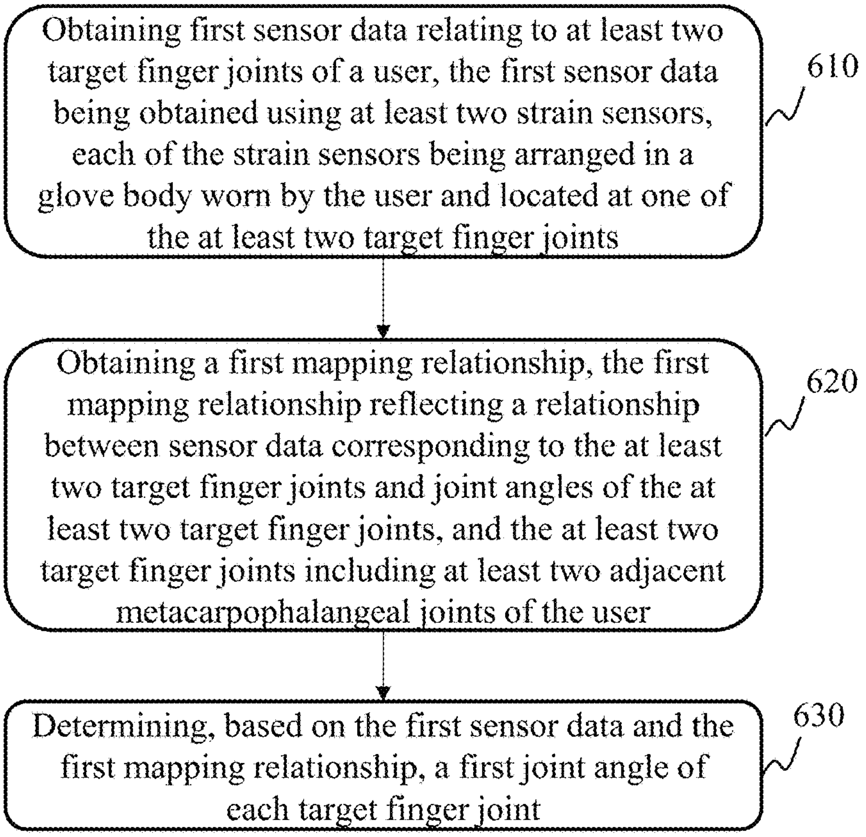
FIG. 6 is a flowchart illustrating an exemplary process for determining a finger joint angle according to some embodiments of the present disclosure.

FIG. 6 is a flowchart illustrating an exemplary process for determining a finger joint angle according to some embodiments of the present disclosure.

In some embodiments, process 600 may be performed by the processing device 410A. As shown in FIG. 6, the process 600 may include the following operations.

In 610, the processing device 410A obtains the first sensor data relating to at least two target finger joints of the user.

The first sensor data may be configured to indicate posture information and/or motion information of the target finger joints of the user, which may be obtained using at least two strain sensors. Each of the at least two strain sensors is arranged in a glove body worn by the user and located at one of the at least two target finger joints. For example, the first sensor data may be obtained using the glove system 100 (hereinafter referred to as the glove system) as described in FIG. 1. The glove system includes a plurality of strain sensors, and the plurality of strain sensors may include first strain sensors and second strain sensors arranged in the glove body 110. More descriptions regarding the glove system 100, the glove body 110, the first strain sensors, and the second strain sensors, may be found in FIG. 1 and related descriptions thereof.

In some embodiments, the processing device 410A may be independent of the glove system, and the processing device 410A may obtain the first sensor data from the glove system. For example, the processing device 410A may obtain the first sensor data from the glove system via a network. As another example, the processing device 410A may be a processor 140 on the glove system and connected to a plurality of strain sensors on the glove body to obtain the first sensor data. In some embodiments, the processing device 410A may obtain the first sensor data from a storage device, such as the storage device 440.

The finger joint may be a joint of the user's finger (e.g., thumb, index finger, middle finger, ring finger, and pinky finger), such as an interphalangeal joint (e.g., a proximal interphalangcal joint and a distal interphalangcal joint), a metacarpophalangcal joint, etc. The target finger joint may be one or a combination of the above finger joints.

In some embodiments, the at least two target finger joints include a part of the finger joints of the user. The part of the finger joints refers to finger joints that are more easily coupled or have a relatively large coupling relationship.

If the movement or deformation (e.g., bending, swinging) of one finger joint leads to a change in the sensor data corresponding to the other finger joint, there is a coupling relationship between the two finger joints. For example, when one finger joint bends, it pulls the fabric of the adjacent finger joint, causing the fabric of the adjacent finger joint to deform, resulting in a change in the sensor data corresponding to the adjacent finger joint (e.g., a change in the sensor data corresponding to the swinging degree of freedom, or a change in the sensor data in the bending degree of freedom further caused by the swinging change). The coupling relationship may include a coupling relationship between finger joints of the same finger, and a coupling relationship between finger joints of different fingers (e.g., adjacent fingers). Merely by way of example, when one finger (e.g., the index finger) is bent, it may lead to the bending of the adjacent finger (e.g., the middle finger), and the index finger has a linkage/coupling relationship with the middle finger and its finger joints.

In some embodiments, the strength of the coupling relationship between the finger joints may be measured in terms of the coupling degree between the finger joints. The coupling degree may be expressed in the form of a numerical value (e.g., a value in the interval [0-1]) or some other forms (e.g., a level). For example, when a slight degree of deformation (e.g., bending, swinging, etc.) of one finger joint may trigger a linked change in the sensor data of the other finger joint, it indicates a high coupling degree (strong coupling relationship) between the two.

In some embodiments, the coupling relationship between the finger joints may be predetermined. For example, a table of coupling relationships may be predetermined, which may include coupling relationships between different finger joints and their coupling degrees. The processing device 410A may determine the target finger joint based on the coupling relationship between the finger joints. For example, the processing device 410A may determine finger joints with a relatively high coupling degree (greater than a predetermined threshold) as the target finger joints. In some embodiments of the present disclosure, a part of the finger joints is determined based on the coupling relationship between different finger joints and their coupling degrees. Thus, the processing device 410A may obtain only the sensor data corresponding to the part of the finger joints, making the calculation process more targeted and reducing the amount of data in the calculation process.

In some embodiments, the at least two target finger joints include at least two adjacent metacarpophalangeal joints of the user. It will be appreciated that the coupling degree between the adjacent metacarpophalangeal joints is relatively high. The processing device 410A may determine at least two adjacent metacarpophalangeal joints of the user as the target finger joints. In some embodiments, the at least two target finger joints include all of the metacarpophalangeal joints of the user.

In some embodiments, the at least two metacarpophalangeal joints include the metacarpophalangeal joints of at least one of the user's index, middle, and ring fingers, and two adjacent fingers on two sides thereof. For example, for the index finger, the thumb and the middle are the two adjacent fingers on two sides of the index finger, thus the at least two metacarpophalangeal joints include the metacarpophalangeal joint of the index finger and the metacarpophalangcal joints of the thumb and the middle finger.

In some embodiments, the at least two metacarpophalangeal joints include the metacarpophalangcal joints of at least one of the thumb and pinky and one of their adjacent fingers. For example, for a thumb, one of whose adjacent fingers is the index finger, thus the at least two metacarpophalangeal joints include a metacarpophalangeal joint of the thumb and a metacarpophalangeal joint of the index finger.

In some embodiments, the at least two target finger joints include at least two adjacent metacarpophalangeal joints of the user and proximal interphalangeal joints corresponding to the at least two metacarpophalangeal joints. For example, the at least two target fingers include the metacarpophalangeal joints of the index and middle fingers and the proximal interphalangeal joints. In some embodiments, the at least two target finger joints include all of the metacarpophalangeal joints and all of the proximal interphalangeal joints of the user. When the metacarpophalangeal joints move or deform, it may also have a coupling effect on the sensor data of the proximal interphalangeal joints. Thus, the processing device 410A also takes into account the coupling relationship between the metacarpophalangeal joints and the proximal interphalangeal joints when determining the finger joint angles.

It should be noted that the interphalangeal joints include the proximal interphalangeal joints and the distal interphalangeal joints, but the distal interphalangeal joints are generally difficult to move (e.g., bend) completely independently, and they exhibit a follow-through to the proximal interphalangcal joints. Thus, the target finger joints may include only all of the metacarpophalangeal joints and all of the proximal interphalangeal joints of the user, but not the distal interphalangcal joints.

In some embodiments of the present disclosure, all metacarpophalangeal joints and all proximal interphalangcal joints are determined as the target finger joints, so that sensors do not need to be arranged at distal interphalangeal joints, which simplifies the structure of the glove system and saves costs. At the same time, the sensor data corresponding to the target finger joints may be processed without data screening, thereby simplifying the processing operation. Additionally, taking all metacarpophalangeal joints and all proximal interphalangeal joints as the target finger joints allows the processing to take into account the coupling relationship between all metacarpophalangeal joints and all proximal interphalangeal joints, so that more accurate first angles of the target finger joints are obtained.

In some embodiments, the at least two first strain sensors include at least two first strain sensors arranged at at least two metacarpophalangeal joints, and each of the at least two first strain sensors is configured to measure the deformation of a corresponding metacarpophalangcal joint in two degrees of freedom.

The degree of freedom refers to a dimension in which an object may move, which may be used to reflect information about the posture or deformation of the object in a specific dimension. The degree of freedom may include, but is not limited to, bending and swinging. The degrees of freedom for different finger joints may or may not be the same. More descriptions regarding the degree of freedom may be found elsewhere in the present disclosure (e.g., FIG. 1).

The first strain sensor refers to a strain sensor arranged at the metacarpophalangeal joint to capture the deformation of the metacarpophalangeal joint in two degrees of freedom (e.g., bending and swinging). In some embodiments, the first strain sensor may be a multi-axis sensor, which may include a plurality of flexible bending sensors, such as inductive sensors, resistive sensors, capacitance sensors, fiber optic sensors, or the like. Merely by way of example, the first strain sensor includes a plurality of capacitance structures, and the capacitance of the plurality of capacitance structures can change in response to the change of the metacarpophalangeal joint in each degree of freedom.

In some embodiments of the present disclosure, movement information detection of a user's joint in a plurality of degrees of freedom (e.g., three dimensions including X-axis bending, Z-axis bending, and Y-axis stretching) may be realized simultaneously by the first strain sensor, which is simple in structure and easy to fabricate. There is no need to provide a sensitive unit (e.g., a capacitance structure) on the sides (sidewalls adjacent to two surfaces in a thickness direction) of the first strain sensor, which reduces the overall size of the sensor (especially the size in the thickness direction). The sensor may be made thinner so as to be applied to smart wearable devices to improve the user's wearing experience. In addition, the electrical quantity of the capacitance structure is positively proportional to its arca or the parameter influencing the arca, having high sensitivity and stability.

Figure 7:
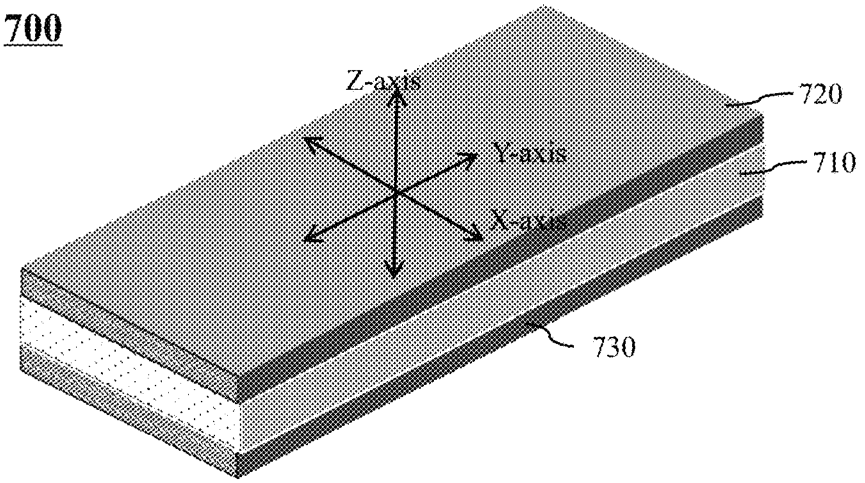
FIG. 7 is a schematic diagram illustrating an exemplary structure of a first strain sensor according to some embodiments of the present disclosure.
Figure 8:
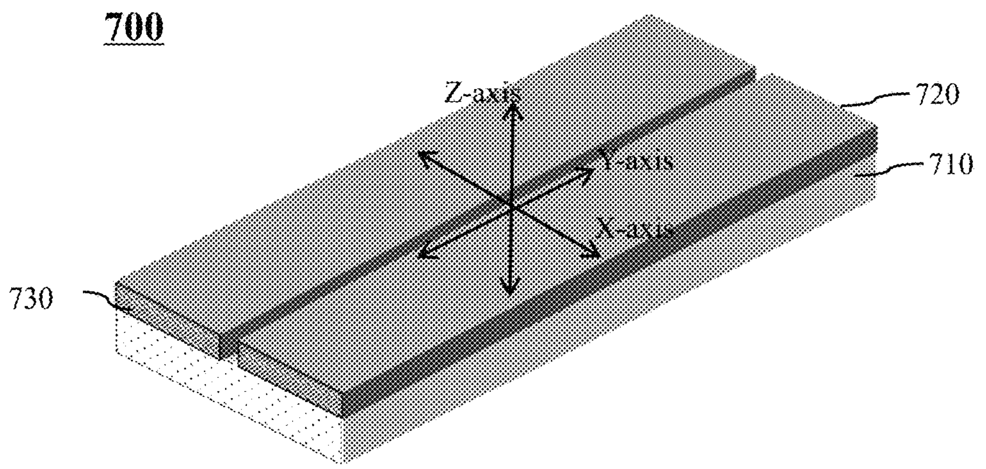
FIG. 8 is a schematic diagram illustrating an exemplary structure of another first strain sensor according to some embodiments of the present disclosure.

FIG. 7 is a schematic diagram illustrating an exemplary structure of a first strain sensor according to some embodiments of the present disclosure, and FIG. 8 is a schematic diagram illustrating an exemplary structure of another first strain sensor according to some embodiments of the present disclosure.

Referring to FIG. 7 and FIG. 8, a first strain sensor 700 includes a flexible substrate 710, a first capacitance structure 720, and a second capacitance structure 730. As shown in FIG. 7, the first capacitance structure 720 and the second capacitance structure 730 are disposed on two sides of the flexible substrate 710 along a thickness direction, and a projection of the first capacitance structure 720 on the flexible substrate 710 and a projection of the second capacitance structure 730 on the flexible substrate at least partially overlaps. In some embodiments, as shown in FIG. 8, the first capacitance structure 720 and the second capacitance structure 730 are disposed on the same side of the flexible substrate 710 in the thickness direction.

The flexible substrate 710 has flexible properties and is prone to deformation (e.g., bending deformation) when subjected to external forces. In some embodiments, the flexible substrate 710 may have a flattened structure to facilitate fit to a human joint. At this point, the flexible substrate 710 has a thickness direction, which may be a Z-axis direction as shown in FIG. 7.

The capacitance structures (including the first capacitance structure 720 and the second capacitance structure 730) are structures used to measure the bending deformation of the flexible substrate 710. Specifically, the capacitance structure has an area, and an electrical quantity (e.g., capacitance) of the capacitance structure is proportional to its area (or a dimensional parameter influencing the area, e.g., a length, a width of the capacitance structure, or a bending angle of the first strain sensor, etc.), i.e., the electrical quantity of the capacitance structure in different directions is proportional to the amount of deformation of the first strain sensor in different degrees of freedom, thus reflecting the deformation situation (e.g. the bending angle and the bending direction). It is to be understood that the first strain sensor may include, but not be limited to, a capacitance structure. For example, the first strain sensor may also be a resistive structure, a capacitor-resistor composite structure, or the like. In some embodiments, both the first capacitance structure 720 and the second capacitance structure 730 may include multilayer structures arranged on the same side of the surface of the thickness direction (Z-axis direction as shown in FIG. 7 or FIG. 8) of the flexible substrate 710, with each layer of multilayer structure stacked along the thickness direction. The multilayer structure is a structure including a stack of layers. The stacking of the each layer of multilayer structure along the thickness direction may be understood as that the plurality of layer structures of the first capacitance structure 720 and the second capacitance structure 730 are aligned along the thickness direction of the flexible substrate 710 and stacked together. In some embodiments, a multilayer structure includes a second conductive layer, an intermediate layer, and a first conductive layer. In some embodiments, the multilayer structure includes a second conductive layer, a second intermediate layer, a third conductive layer, a first intermediate layer, and a first conductive layer. Descriptions regarding the specific layer structures of the multilayer structure may be found hereinafter.

When different capacitance structures are arranged at different positions of the first strain sensor 700, respectively, these capacitance structures generate differentiated responses to deformations in different dimensions of the flexible substrate 710. When the flexible substrate 710 produces deformation of a certain dimension, detection parameters generated by these capacitance structures have characteristics corresponding to the deformation of the dimension. When the flexible substrate 710 produces deformation of another dimension, detection parameters generated by these capacitance structures may again have characteristics corresponding to the dimension of deformation. It may be understood that the characteristics of the detection parameters generated by these capacitance structures correspond to the dimensions of the deformation of the flexible substrate 710 one by one. On this basis, the deformation of the flexible substrate 710 may be recognized based on the detection parameters of each capacitance structure. In some embodiments, a processor (e.g., the processor 140 or an external computing device (e.g., the processor 410A)) may determine the deformation of the flexible substrate 710 in at least two dimensions based on parameters relating to the capacitance of each capacitance structure (e.g., the first capacitance structure 720 and the second capacitance structure 730) using a specific algorithm. For example, the deformation of the flexible substrate 710 in at least two dimensions is determined using a machine learning model, a mapping relationship, or a functional relationship. Descriptions regarding the deformation in at least two dimensions may be found hereinafter.

A bending deformation of the first strain sensor 700 (or the flexible substrate 710) results in a subsequent change in the physical shapes of at least some of the capacitance structures (e.g., the first capacitance structure 720 and the second capacitance structure 730) disposed on the flexible substrate 710, which results in a change in the capacitance thereto. For example, the bending of the first strain sensor 700 causes a change in the area of the capacitance structure, which changes the capacitance of the capacitance structure. By capturing the capacitance of the capacitance structure or a parameter relating to the capacitance and analyzing the change in the capacitance of the capacitance structure or the parameter relating to the capacitance, the bending of the first strain sensor 700 (e.g., the bending angle, the bending direction) may be sensed more accurately.

As shown in FIG. 7, in some embodiments, the first capacitance structure 720 and the second capacitance structure 730 are disposed on two sides of the flexible substrate 710 along the thickness direction. In some embodiments, the first capacitance structure 720 and the second capacitance structure 730 are disposed symmetrically along the flexible substrate 710 in the thickness direction. In such cases, a projection of the first capacitance structure 720 on the flexible substrate 710 and a projection of the second capacitance structure 730 on the flexible substrate 710 overlap completely. When the first capacitance structure 720 and the second capacitance structure 730 are symmetrically disposed about the flexible substrate 710 in the thickness direction, the two capacitance structures have the same response to a portion of the external disturbance (e.g., an overall stretching or compression of the first strain sensor along a certain direction). In such cases, according to the parameters relating to the capacitance of the capacitance structure, the influence of the external disturbance on the first strain sensor 700 may be eliminated through the differential processing algorithm, thereby increasing the sensitivity of determining the deformation in least two degrees of freedom of the flexible substrate 710.

In some embodiments, the flexible substrate 710 includes a short-axis direction and a long-axis direction that are perpendicular to the thickness direction, and the deformation in the plurality of degrees of freedom generated by the first strain sensor 700 (the flexible substrate 710) shown in FIG. 7 includes at least a bending deformation around an axis parallel to the short-axis direction and a stretching or compressive deformation along the long-axis direction. The short-axis direction may be the X-axis direction shown in FIG. 7, and the long-axis direction may be the Y-axis direction shown in FIG. 7.

As shown in FIG. 7, when the first strain sensor 700 is deformed by bending around an axis parallel to the short-axis direction (i.e., the X-axis direction), the first capacitance structure 720 and the second capacitance structure 730 may undergo a stretching deformation and a compression deformation, respectively. For example, the first capacitance structure 720 is bent and elongated and the second capacitance structure 730 is bent and compressed such that the first capacitance structure 720 and the second capacitance structure 730 may undergo opposite changes in capacitance. In this case, the difference between the capacitances of the first capacitance structure 720 and the second capacitance structure 730 may reflect the direction of bending and the degree of bending of the first strain sensor 700 around the axis parallel to the X-axis direction. Since the first capacitance structure 720 and the second capacitance structure 730 are stretched and compressed to substantially the same degree, the sum of their capacitances may remain substantially constant.

When the first strain sensor 700 is deformed by stretching or compression in the long-axis direction, the first capacitance structure 720 and the second capacitance structure 730 are stretched or compressed synchronously such that the capacitance of the first capacitance structure 720 and the capacitance of the second capacitance structure 730 may be simultaneously changed. In this case, the difference between the capacitances of the first capacitance structure 720 and the second capacitance structure 730 remains essentially constant (or close to 0), while the sum of the capacitances may reflect the degree of stretching or compression of the first strain sensor 700 along the long-axis direction.

In some embodiments, by comparing the characteristics of the capacitances of the first capacitance structure 720 and the second capacitance structure 730 in the two degrees of freedom, such as a relationship between the sum (difference) of the capacitances and the deformation of the flexible substrate 710, mutual interference between the deformations of the two degrees of freedom may be avoided, and the deformation of the flexible substrate 710 in the two degrees of freedom may be effectively distinguished. For example, when the first strain sensor 700 is stretched or compressed as a whole, the first capacitance structure 720 and the second capacitance structure 730 may be stretched or compressed synchronously. The synchronized stretching or compression of the first capacitance structure 720 and the second capacitance structure 730 is regarded as a common-mode interference, at this time, differential processing of the signals (e.g., capacitance) may exclude such common-mode interference such that the first strain sensor 700 is not sensitive to its own stretching or compression deformation and is only sensitive to the bending deformation around the axis parallel to the short-axis direction (i.e., the X-axis direction), enabling the first strain sensor 700 to detect the bending deformation of this degree of freedom accurately. That is, the difference between the capacitances of the first capacitance structure 720 and the second capacitance structure 730 primarily reflects the bending deformation of the flexible substrate 710 around the axis parallel to the short-axis direction (i.e., the X-axis direction). Similarly, the sum of the capacitances of the first capacitance structure 720 and the second capacitance structure 730 primarily reflects the stretching or compressive deformation of the flexible substrate 710 along the long-axis direction. The detection principle of stretching or compressive deformation in the long-axis direction is similar to the detection principle of the first strain sensor 700 having the four capacitance structures, more descriptions regarding which can be found in FIG. 10A to FIG. 12 and their related descriptions.

As shown in FIG. 8, in some embodiments, the flexible substrate 710 includes a long-axis direction perpendicular to the thickness direction, the first capacitance structure 720 and the second capacitance structure 730 are distributed on the same side of the flexible substrate 710 in the thickness direction, the first capacitance structure 720 and the second capacitance structure 730 are disposed side by side and both extend along the long-axis direction of the flexible substrate 710.

In some embodiments, the first capacitance structure 720 and the second capacitance structure 730 are symmetrically disposed along a middle cross-section parallel to a plane formed by the thickness direction and the long-axis direction. The middle cross-section is located on the flexible substrate 710. When the first capacitance structure 720 and the second capacitance structure 730 are symmetrically disposed about the middle cross-section on the flexible substrate 710, the two capacitance structures have the same response to a portion of the external disturbance (e.g., an overall stretching or compression of the first strain sensor 700 in a certain direction). At this time, a processor (e.g., a processor 140) or an external computational device (e.g., the processor 410A) may exclude the effect of the external disturbance on the first strain sensor 700 based on the parameters relating to the capacitance of the capacitance structures (such as the first capacitance structure 720 and the second capacitance structure 730) using the differential processing algorithm, thereby increasing the sensitivity of determining the deformation in at least two degrees of freedom of the flexible substrate 710. More descriptions regarding the middle cross-section may be found in FIG. 9A and FIG. 9B and their related descriptions.

In some embodiments, the first strain sensor 700 (or the flexible substrate 710) shown in FIG. 8 produces deformations including at least bending deformation around an axis parallel to the thickness direction and a stretching or compression deformation along the long-axis direction.

As shown in FIG. 8, when the first strain sensor 700 is deformed by bending along an axis parallel to the thickness direction (i.e., the Z-axis direction), the first capacitance structure 720 and the second capacitance structure 730 may undergo a stretching deformation, and a compressive deformation, respectively, for example, the first capacitance structure 720 is bent and elongated and the second capacitance structure 730 is bent and compressed. At this time, the first capacitance structure 720 and the second capacitance structure 730 may undergo opposite changes in capacitance. In this case, the difference between the capacitances of the first capacitance structure 720 and the second capacitance structure 730 may reflect the direction of the bending and the degree of the bending of the first strain sensor 700 around the axis parallel to the Z-axis direction. Since the first capacitance structure 720 and the second capacitance structure 730 are stretched and compressed to substantially the same degree, the sum of their capacitances may remain substantially constant.

When the first strain sensor 700 shown in FIG. 8 is deformed by stretching or compression along the long-axis direction, the first capacitance structure 720 and the second capacitance structure 730 may be stretched or compressed synchronously. The first capacitance structure 720 and the second capacitance structure 730 may undergo a synchronized change in capacitance. In this case, the difference between the capacitance of the first capacitance structure 720 and the capacitance of the second capacitance structure 730 remains essentially constant (or close to 0), while the sum of the capacitances may reflect the degree of stretching or compression of the first strain sensor 700 along the long-axis direction.

In some embodiments, by comparing the characteristics of the capacitances of the first capacitance structure 720 and the second capacitance structure 730 in the two degrees of freedom, such as a relationship between the sum (difference) of the capacitances and the deformation of the flexible substrate 710, mutual interference between the deformations of the two degrees of freedom may be avoided, and the deformation of the flexible substrate 710 in the two degrees of freedom may be effectively distinguished. For example, when the first strain sensor 700 is stretched or compressed as a whole, the first capacitance structure 720 and the second capacitance structure 730 may be stretched or compressed synchronously. The synchronized stretching or compression of the first capacitance structure 720 and the second capacitance structure 730 is regarded as a common-mode interference. A differential processing of the signals (e.g., capacitances) may exclude such common-mode interference. Thus, the first strain sensor 700 is not sensitive to its own stretching or compression deformation and is only sensitive to the bending deformation around the axis parallel to the thickness direction (i.e., the Z-axis direction), enabling the first strain sensor 700 to detect the bending deformation of this degree of freedom accurately. That is, the difference between the capacitances of the first capacitance structure 720 and the second capacitance structure 730 primarily reflects the bending deformation of the flexible substrate 710 around the axis parallel to the thickness direction (i.e., the Z-axis direction). Similarly, the sum of the capacitances of the first capacitance structure 720 and the second capacitance structure 730 primarily reflects the stretching or compressive deformation of the flexible substrate 710 along the long-axis direction. The detection principle of stretching or compressive deformation in the long-axis direction is similar to the detection principle of the first strain sensor 700 having the four capacitance structures, more descriptions regarding which can be found in FIG. 10A to FIG. 12 and their related descriptions.

In some embodiments, the first sensor data obtained by the processing device 410A may include raw data collected by at least two strain sensors. Merely by way of example, when the strain sensor includes the capacitance structure, the raw data may include the capacitance valuc of the capacitance structure. When the strain sensor includes an inductive structure, the raw data may include an inductance value of the inductive structure. Using the raw data directly as the first sensor data may simplify the data processing process.

In some embodiments, the processing device 410A may determine decoupling data of at least two target finger joints based on the raw data. The first sensor data obtained by the processing device 410A may include the decoupling data. The decoupling data may include parameters that reflect the deformations of the first strain sensor in different dimensions. For example, the raw data may be decoupled into parameters (e.g., Ctotal, dCx, dCz, etc. obtained according to the differential processing algorithm in the following) that reflect the bending deformation of the strain sensor around the axis parallel to the thickness direction, the bending deformation of the strain sensor around the axis parallel to the short-axis direction, and the stretching or compressive deformation of the strain sensor along the long-axis direction, thereby restoring the actual bending movement of the sensor. More descriptions regarding the data decoupling may be found in FIGS. 9A-14 and related descriptions thereof.

Figure 9A:
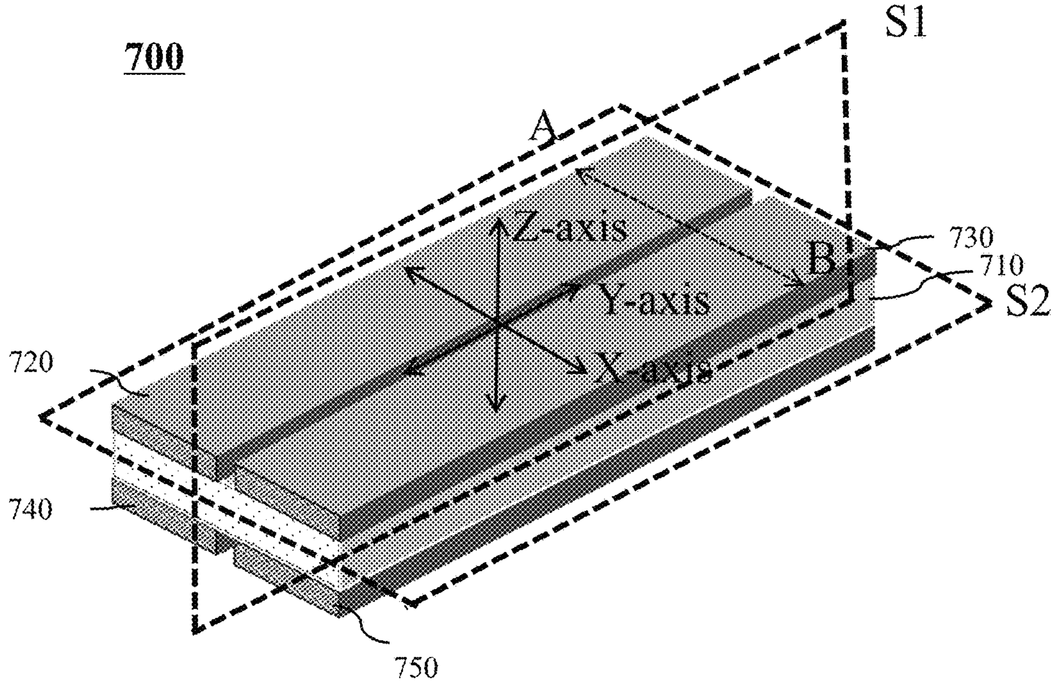
FIG. 9A is a schematic diagram illustrating a distribution of four capacitance structures on a flexible substrate according to some embodiments of the present disclosure.
Figure 9B:
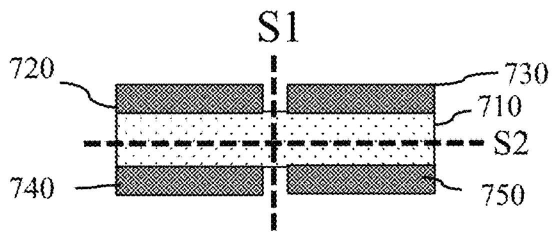
FIG. 9B is a schematic diagram illustrating a cross-sectional structure of the four capacitance structures in FIG. 9A along a Y-axis.

FIG. 9A is a schematic diagram illustrating the distribution of four capacitance structures on a flexible substrate according to some embodiments of the present disclosure, and FIG. 9B is a schematic diagram illustrating a cross-sectional structure of the four capacitance structures in FIG. 9A along a Y-axis.

As shown in FIG. 9A and FIG. 9B, in some embodiments, compared to FIG. 8, the first strain sensor 700 further includes a third capacitance structure 740 and a fourth capacitance structure 750. The first capacitance structure 720 and the second capacitance structure 730 are disposed side-by-side on one side surface of the flexible substrate 710 along the thickness direction and both extend in the long-axis direction. The third capacitance structure 740 and the fourth capacitance structure 750 are disposed side-by-side on the other side surface of the flexible substrate 710 along the thickness direction and both extend in the long-axis direction.

In some embodiments, the processor reads parameters relating to the capacitance of the first capacitance structure 720, the second capacitance structure 730, the third capacitance structure 740, and the fourth capacitance structure 750, respectively, and determines, based on the parameters, the deformation in at least two degrees of freedom of the flexible substrate 710.

In some embodiments, the first strain sensor 700 (the flexible substrate 710) shown in FIG. 9A generates deformations including at least a bending deformation around the axis parallel to the thickness direction, a bending deformation around the axis parallel to the short-axis direction, and a stretching or compressive deformation along the long-axis direction of the flexible substrate 710. Merely by way of example, the following descriptions of parameters relating to the capacitance of each capacitance structure under deformation with different degrees of freedom are given in conjunction with FIG. 10A, FIG. 10B, FIG. 11, and FIG. 12, respectively.

In some embodiments, parameters relating to the capacitance include C1, C2, C3, C4, Ctotal, dCx, and dCz. Ctotal=C1+C2+C3+C4, dCx=(C1+C2)–(C3+C4) according to a composite difference operation, and dCz=(C1+C3)–(C2+C4) according to a composite differential operation. C1, C2, C3, and C4 denote capacitances of the first capacitance structure 720, the second capacitance structure 730, the third capacitance structure 740, and the fourth capacitance structure 750, respectively.

In some embodiments, the first capacitance structure 720 and the second capacitance structure 730 are symmetrically disposed about a first middle cross-section S1, and the third capacitance structure 740 and the fourth capacitance structure 750 are symmetrically disposed about the first middle cross-section S1. The first middle cross-section S1 represents a cross-section in the flexible substrate 710 that is parallel to a plane formed by the thickness direction and the long-axis direction. The first capacitance structure 720 and the third capacitance structure 740 are symmetrically disposed about the second middle cross-section S2 of the flexible substrate 710, and the second capacitance structure 730 and the fourth capacitance structure 750 are symmetrically disposed about the second middle cross-section S2. The second middle cross-section S2 represents a middle plane parallel to the plane formed by the long-axis direction and the short-axis direction in the flexible substrate 710.

By providing four capacitance structures symmetrically on the first strain sensor 700 and performing the composite differential operation, common-mode interference may be effectively excluded during the process of recognizing the bending deformation of the sensor. Merely by way of example, when the first strain sensor 700 is deformed by stretching or compression as a whole, the first capacitance structure 720, the second capacitance structure 730, the third capacitance structure 740, and the fourth capacitance structure 750 arc synchronously stretched or compressed. The stretching or compression of the four capacitance structures is regarded as the common-mode interference, and the dCx and dCz obtained by setting up the four capacitance structures and performing the composite differential operation of the signals are kept unchanged, which effectively excludes the common-mode interference, so that the flexible first strain sensor 700 is insensitive to the stretching or compression of the first strain sensor 700, but only to the bending of the first strain sensor 700, which increases the accuracy of the first strain sensor 700.

Figure 10A:
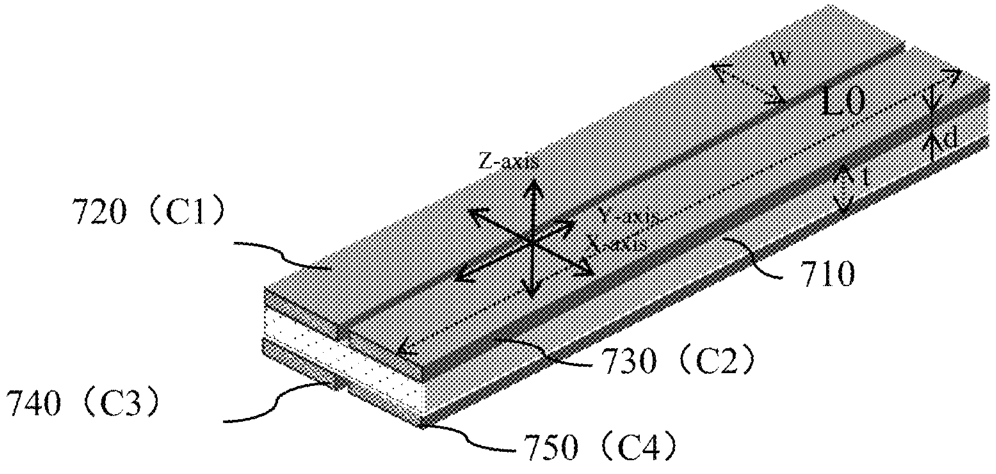
FIG. 10A is a schematic diagram illustrating a second sensor without deformation according to some embodiments of the present disclosure.
Figure 10B:
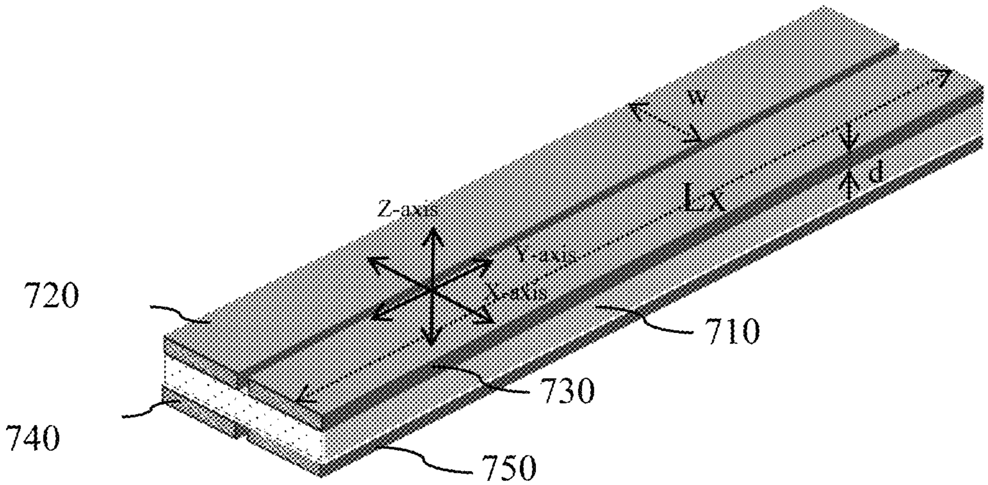
FIG. 10B is a schematic diagram illustrating the second sensor in FIG. 10A deformed by stretching or compression along a long-axis.

FIG. 10A is a schematic diagram illustrating a second sensor without deformation according to some embodiments of the present disclosure, and FIG. 10B is a schematic diagram illustrating the second sensor in FIG. 10A deformed by stretching or compression along a long-axis.

In some embodiments, when the first capacitance structure 720, the second capacitance structure 730, the third capacitance structure 740, and the fourth capacitance structure 750 are all capacitors, the stretching or compressive deformation in the long-axis direction of the flexible substrate 11 of the first strain sensor 700 may be recognized based on parameters relating to the capacitance.

In some embodiments, when the first strain sensor 700 shown in FIG. 10A is not deformed, the capacitances of the four capacitance structures may be obtained according to the following equation (1). Merely by way of example, the four capacitance structures of the first strain sensor 700 are considered to be identical and symmetrical about the flexible substrate 710 (i.e., the first center section S1 and the second center section S2) in all directions:

$$C1 = C2 = C3 = C4 = \varepsilon_0\varepsilon\frac{A}{d} = \varepsilon_0\varepsilon\frac{L0w}{d}, \tag{1}$$

where $\varepsilon_0$ denotes the vacuum dielectric constant; ε denotes the relative dielectric constant of each of the four capacitance structures (i.e., the intermediate layer as described below); d denotes the thickness of the dielectric layer of each of the four capacitance structures; A denotes the area of each of the four capacitance structures on the plane formed by the long-axis direction and the short-axis direction; L0 denotes the initial length of each of the four capacitance structures in the long-axis direction of the flexible substrate 710; and w denotes the width of each of the four capacitance structures in the short-axis direction of the flexible substrate 710.

In some embodiments, as shown in FIG. 10B, the initial length L0 of each of the four capacitance structures is elongated or compressed to Lx when the first strain sensor 700 after stretching or compression along the long-axis direction (i.e., the Y-axis direction). Considering that the thickness of each of the four capacitance structures changes very little, it is approximated that the thickness of each of the four capacitance structures remains unchanged, and then according to equation (1), the capacitances of the four capacitance structures may be determined according to equation (2) below:

$$C1 = C2 = C3 = C4 = \varepsilon_0\varepsilon\frac{Lxw}{d}. \tag{2}$$

At this time, Ctotal, dCx, dCz are determined according to the following equations (3), (4), and (5), respectively.

$$Ctotal = C1 + C2 + C3 + C4 = 4\varepsilon_0\varepsilon\frac{Lxw}{d}, \tag{3}$$

$$dCx = (C1 + C2) - (C3 + C4) = 0, \tag{4}$$

$$dCz = (C1 + C3) - (C2 + C4) = 0. \tag{5}$$

When the first strain sensor 700 is deformed by stretching or compression in the long-axis direction, the four capacitance structures are stretched or compressed synchronously. In this case, the sum of the capacitances of the four capacitance structures may reflect the degree of stretching or compression of the first strain sensor 700 (or the flexible substrate 710) along the long-axis direction. According to the equations (2) and (3), Ctotal is related only to the length Lx after the capacitance structure is deformed, and Lx may be used to represent the stretching or compressive deformation of the first strain sensor 700 along the long-axis direction. Thus Ctotal may be used to reflect the stretching or compressive deformation of the first strain sensor 700 (the flexible substrate 710) along the long-axis direction.

According to equation (4), dCx reflects a difference between a sum of the capacitance C1 of the first capacitance structure 720 and the capacitance C2 of the second capacitance structure 730, and a sum of the capacitance C3 of the third capacitance structure 740 and the capacitance C4 of the fourth capacitance structure 750. According to the structural distribution of the four capacitance structures in FIG. 10B, the sum of the capacitance C1 of the first capacitance structure 720 and the capacitance C2 of the second capacitance structure 730, i.e., C1+C2, may reflect the bending deformation of the upper side of the flexible substrate 710 in the thickness direction. The sum of the capacitance C3 of the third capacitance structure 740 and the capacitance C4 of the fourth capacitance structure 750, i.e., C3+C4, may reflect the bending deformation of the lower side of the flexible substrate 710 in the thickness direction. Therefore, dCx is used to reflect the difference in the bending deformations of the upper side and the lower side (i.e., the upper and lower side in the thickness direction) of the flexible substrate 710 when it is deformed, which is related to the bending deformation around the axis parallel to the short-axis direction (i.e., the X-axis direction). Whereas the stretching or the compression deformation along the long-axis direction (i.e., the Y-axis direction) does not result in the difference in the deformations of the upper and lower sides of the flexible substrate 710, so dCx is a constant 0.

Similarly, according to equation (5), dCz is used to reflect the difference in bending deformations of the two sides of the flexible substrate 710 along the short-axis direction when it deforms, dCz is only related to the bending deformation around the axis parallel to the thickness direction (i.e., the Z-axis direction), and the stretching or compressive deformation in the long-axis direction (i.e., Y-axis direction) may not result in the difference in the bending deformations of the two sides of the flexible substrate 710 in the short-axis direction, so dCz is a constant 0.

In some embodiments, the output parameter Ctotal of the first strain sensor 700 stretched or compressed along the Y-axis varies linearly in direct proportion to the length Lx after the stretching or compression deformation, which has a very high degree of linearity, while dCz and dCx are both 0 and are not affected by the length Lx. Therefore, the stretching or compressive deformation along the long-axis direction of the flexible substrate 710 of the first strain sensor 700 may be recognized based on the Ctotal.

Figure 11:
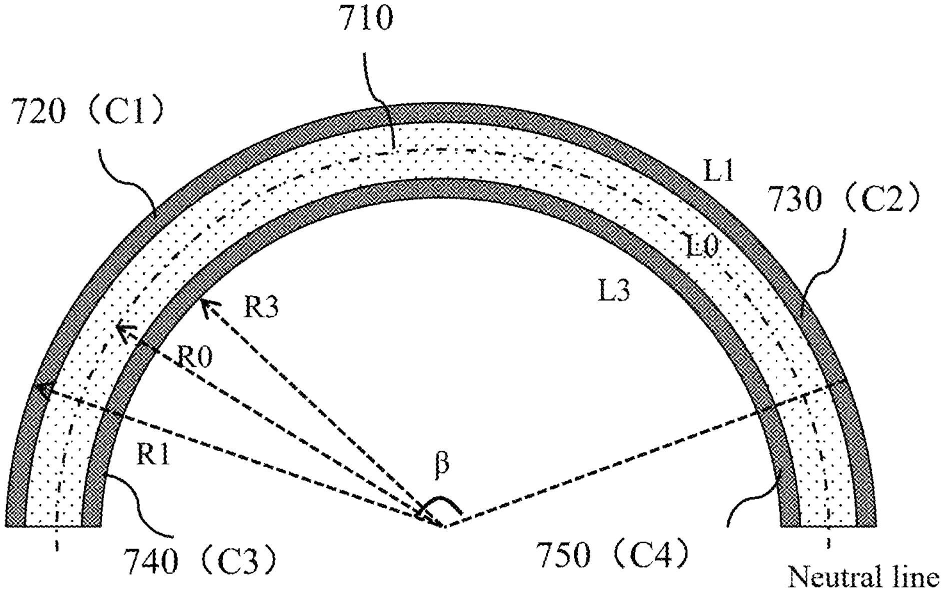
FIG. 11 is a schematic diagram illustrating a side view of the first strain sensor in FIG. 10A deformed by bending around an axis parallel to a short-axis direction.

FIG. 11 is a schematic diagram illustrating a side view of the first strain sensor in FIG. 10A deformed by bending around an axis parallel to the short-axis direction.

In some embodiments, when the first capacitance structure 720, the second capacitance structure 730, the third capacitance structure 740, and the fourth capacitance structure 750 are all capacitors, a bending deformation of the flexible substrate 710 around an axis parallel to the short-axis direction of the first strain sensor 700 may be recognized based on the parameter relating to the capacitance dCx.

As shown in FIGS. 10A and 11, when the first strain sensor 700 is deformed by bending along the axis parallel to the short-axis direction (i.e., the X-axis direction), for convenience of illustration, it is approximated that the first strain sensor 700 after the bending deformation is a circular arc, the first capacitance structure 720 and the second capacitance structure 730 are bent and elongated to L1, and the third capacitance structure 740 and the fourth capacitance structure 750 are bent and compressed to L3. Considering that the thickness of each of the four capacitance structures changes very little, approximating that the thickness of each of the four capacitance structures remains unchanged for convenience of illustration, and according to equation (1), the capacitance C1 of the first capacitance structure 720 and the capacitance C2 of the second capacitance structure 730 may be determined according to equation (6) as described below, and the capacitance C3 of the third capacitance structure 740 and the capacitance C4 of the fourth capacitance structure 750 may be determined according to equation (7) as described below:

$$C1 = C2 = \varepsilon_0\varepsilon\frac{L1w}{d} = \varepsilon_0\varepsilon\frac{R1\beta w}{d} = \varepsilon_0\varepsilon\frac{(R0+t/2)\beta w}{d}, \tag{6}$$

$$C3 = C4 = \varepsilon_0\varepsilon\frac{L3w}{d} = \varepsilon_0\varepsilon\frac{R3\beta w}{d} = \varepsilon_0\varepsilon\frac{(R0-t/2)\beta w}{d}. \tag{7}$$

At this time, Ctotal, dCx, dCz are determined according to the following equations (8), (9), and (10):

$$Ctotal = C1 + C2 + C3 + C4 = 4\varepsilon_0\varepsilon\frac{L0w}{d}, \tag{8}$$

$$dCx = (C1 + C2) - (C3 + C4) = \frac{2\varepsilon_0\varepsilon wt}{d}\beta, \tag{9}$$

$$dCz = (C1 + C3) - (C2 + C4) = 0, \tag{10}$$

where R0 denotes a radius of the circular arc formed by the bending deformation of the flexible substrate 710; R1 denotes a radius of the circular arc formed by the bending deformation of the first capacitance structure 720 and the second capacitance structure 730; R2 denotes a radius of the circular arc formed by the bending deformation of the third capacitance structure 740 and the fourth capacitance structure 750; t denotes the thickness of the first strain sensor 700 as shown in FIG. 10A; L1 denotes a length of the circular arc formed by the bending deformation of the first capacitance structure 720 and the second capacitance structure 730; and L3 denotes a length of the circular arc formed by the bending deformation of the third capacitance structure 740 and the fourth capacitance structure 750.

When the first strain sensor 700 bends and deforms around the axis parallel to the short-axis direction, for example, when the first capacitance structure 720 and the second capacitance structure 730 undergo a bending and stretching, and the third capacitance structure 740 and the fourth capacitance structure 750 undergo a bending and compression, a sum of the capacitance C1 of the first capacitance structure 720 and the capacitance C2 of the second capacitance structure 730, i.e., C1+C2, has an opposite change relationship to a sum of the third capacitance C3 of the capacitance structure 740 and the capacitance C4 of the fourth capacitance structure 750, i.e., C3+C4. At this time, the Ctotal obtained by adding the capacitances of the four capacitance structures may offset the changing trends of the C1+C2 and the C3+C4, i.e., Ctotal is a constant shown in equation (8), and Ctotal can't be used for reflecting the bending deformation of the first strain sensor 700 around the axis parallel to the short-axis direction.

In some embodiments, the output parameter dCx of the first strain sensor 700 after the bending deformation around the axis parallel to the short-axis direction (i.e., the X-axis direction) varies linearly in direct proportion to a bending angle β, which has a very high degree of linearity. Whereas dCz and Ctotal are both constants and are not affected by the bending angle β. Thus, the bending deformation around the axis parallel to the short-axis direction of the first strain sensor 700 may be recognized based on the parameter dCx relating to the capacitance.

It should be noted that, in addition to the case of the four capacitance structures described above, there may be three or more capacitance structures on the first strain sensor 700 distributed on two sides of the surface of the flexible substrate 710 along the thickness direction, and all of them extend along the long-axis direction. As long as the deformation in different dimensions may be characterized by the parameters relating to the capacitance of these capacitance structures, the deformation in multiple dimensions may be recognized. Merely by way of example, there are three capacitance structures on the first strain sensor 700, two of which are distributed on the upper side of the flexible substrate and the other on the lower side of the flexible substrate. At this time, parameters relating to the capacitance of each of the three capacitance structures are also related to the bending deformation around the X-axis (or Z-axis). The bending deformation of the first strain sensor 700 around the X-axis (or Z-axis) may also be calculated by combining the parameters relating to the capacitance generated by each of the three sensor structures.

Figure 12:
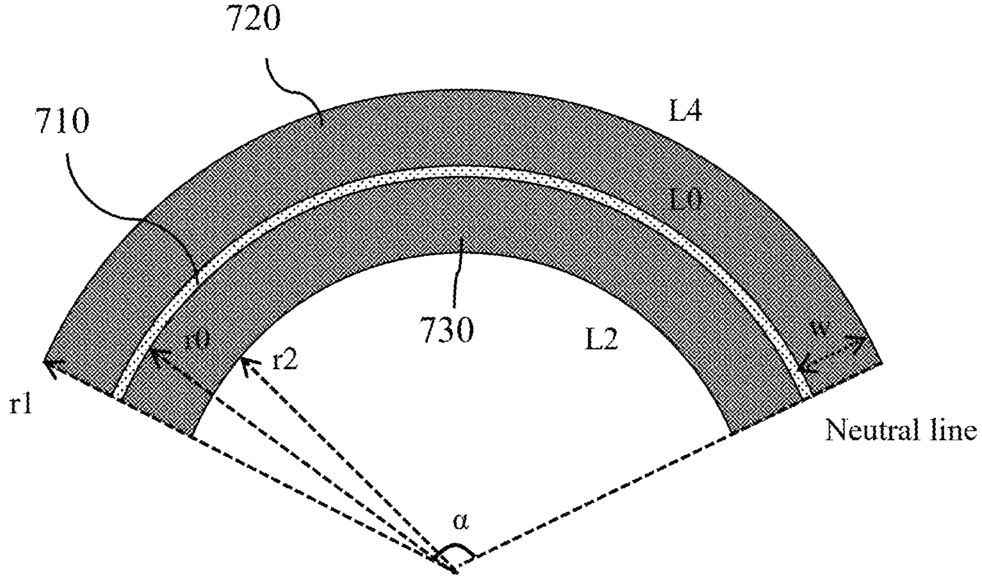
FIG. 12 is a schematic diagram illustrating a top view of the first strain sensor in FIG. 10A deformed by bending around an axis parallel to a thickness direction.

FIG. 12 is a schematic diagram illustrating a top view of the first strain sensor in FIG. 10A deformed by bending around an axis parallel to a thickness direction.

In some embodiments, when the first capacitance structure 720, the second capacitance structure 730, the third capacitance structure 740, and the fourth capacitance structure 750 are all capacitors, a bending deformation of the flexible substrate 710 around the axis parallel to the thickness direction of the first strain sensor 700 may be recognized based on the parameter relating to the capacitance dCz.

As shown in FIGS. 10A and 12, when the first strain sensor 700 is deformed by bending around the axis parallel to the thickness direction (i.e., the Z-axis direction), for convenience of illustration, it is approximated that the first strain sensor 700 after the bending deformation may be a circular arc, the first capacitance structure 720 and the third capacitance structure 740 (not shown in FIG. 12) are bent and elongated to L4, the second capacitance structure 730 and the fourth capacitance structure 750 (not shown in FIG. 12) are bent and compressed to L2. Considering that the thickness of each of the four capacitance structures changes very little, for convenience of illustration, it is approximated that the thickness of each of the four capacitance structures remains unchanged. Then, according to equation (1), the capacitance C1 of the first capacitance structure 720 and the capacitance C3 of the third capacitance structure 740 may be determined according to equation (11), and the capacitance C2 of the second capacitance structure 730 and the capacitance C4 of the fourth capacitance structure 750 may be determined according to equation (12):

$$C1 = C3 = \varepsilon_0\varepsilon\frac{(L0+L4)w}{2d} = \varepsilon_0\varepsilon\frac{(r0\alpha+r1\alpha)w}{2d} = \varepsilon_0\varepsilon\frac{(2r0+w)\alpha w}{2d}, \quad (11)$$

$$C2 = C4 = \varepsilon_0\varepsilon\frac{(L0+L2)w}{2d} = \varepsilon_0\varepsilon\frac{(r0\alpha+r2\alpha)w}{2d} = \varepsilon_0\varepsilon\frac{(2r0-w)\alpha w}{2d}. \quad (12)$$

At this time, Ctotal, dCx, dCz are determined according to the following equations (13), (14), and (15), respectively.

$$Ctotal = C1 + C2 + C3 + C4 = 4\varepsilon_0\varepsilon\frac{L0w}{d}, \quad (13)$$

$$dCx = (C1 + C2) - (C3 + C4) = 0, \quad (14)$$

$$dCz = (C1 + C3) - (C2 + C4) = \frac{2\varepsilon_0\varepsilon w^2}{d}\alpha, \quad (15)$$

where r0 denotes a radius of the circular arc formed by the bending deformation of the flexible substrate 710; r1 denotes a radius of the circular arc formed by the bending deformation of the first capacitance structure 720 and the third capacitance structure 740; r2 denotes a radius of the circular arc formed by the bending deformation of the second capacitance structure 730 and the fourth capacitance structure 750; L2 denotes a length of the circular arc formed by the bending deformation of the first capacitance structure 720 and the third capacitance structure 740; and L4 denotes a length of the circular arc formed by the bending deformation of the second capacitance structure 730 and the fourth capacitance structure 750.

In some embodiments, the output parameter dCz of the first strain sensor 700 after bending deformation around the axis parallel to the thickness direction (i.e., the Z-axis direction) varies linearly in proportion to a bending angle α, and has a very high degree of linearity, whereas dCx and Ctotal are both constants and are not affected by the bending angle α. Thus, the bending deformation around the axis parallel to the thickness direction of the first strain sensor 700 may be recognized based on a parameter dCz relating to the capacitance.

In some embodiments, when the first capacitance structure 720, the second capacitance structure 730, the third capacitance structure 740, and the fourth capacitance structure 750 are all resistive structures, the processor may determine the deformation of the flexible substrate 710 in at least two dimensions based on resistance-related parameters of the four capacitance structures. For example, the resistance of each of the four capacitance structures is R1=R2=R3=R4=ρd/A. The area of each capacitance structure after deformation is substituted into the equation and a differential operation is performed, a result similar to the parameters relating to the capacitance may be obtained, such that the processor to determine the bending deformation of the first strain sensor 700 around the axis parallel to the thickness direction, the bending deformation of the first strain sensor 700 around the axis parallel to the short-axis direction, and the stretching or compressive deformation of the first strain sensor 700 along the long-axis direction of the flexible substrate. ρ denotes the resistivity of each of the four capacitance structures (i.e., the intermediate layer, referring to the following description).

In some embodiments, the processor may recognize a composite deformation coexisting with deformations of any one of the bending deformation of the first strain sensor 700 around the axis parallel to the thickness direction, the bending deformation of the first strain sensor 700 around the axis parallel to the short-axis direction, and the stretching or compressive deformation of the first strain sensor 700 along the long-axis direction of the flexible substrate 710. For example, the processor may simultaneously calculate the changes of the parameters Ctotal, dCx, and dCz relating to the capacitance, thereby simultaneously restoring the deformation components in different dimensions to restore the actual bending deformation of the first strain sensor 700.

Figure 13:
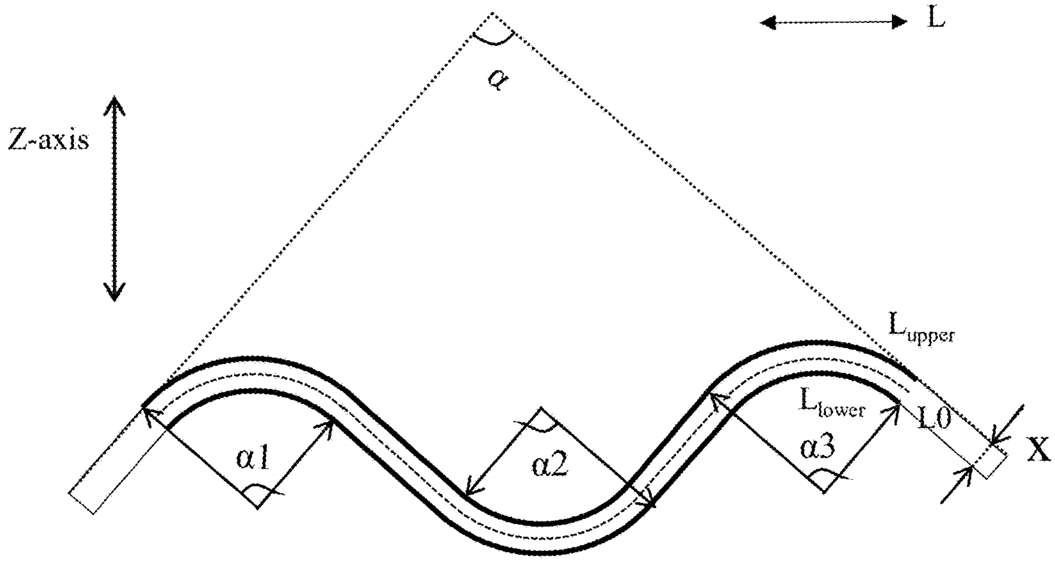
FIG. 13 is a schematic diagram illustrating a flexible sensor that is wrinkled according to some embodiments of the present disclosure.

FIG. 13 is a schematic diagram illustrating a flexible sensor that is wrinkled according to some embodiments of the present disclosure.

The flexible sensor may be a first strain sensor, as shown in FIG. 13, when the sensor has a composite deformation in a plurality of dimensions, resulting in wrinkles on the flexible sensor (FIG. 13 illustrates wrinkles in the length direction L), which is equivalent to the emergence of more than one bend (the bending angles may include α1, α2, α3), and through geometric integration, α1, α2, α3 do not need to be taken into account again, and only the included angle between the head and tail of the flexible sensor need to be taken into account. That is to say, regardless of how many bends the flexible sensor has, the length $L_{upper}$=L0+αx/2 of the upper surface of the sensor and the length $L_{lower}$=L0−αx/2 of the lower surface of the flexible sensor along the thickness direction remain applicable, while the length of the neutral line L0 remains unchanged, where α denotes the included angle between the head and the tail of the flexible sensor, and x denotes the width (or thickness) of the flexible sensor in the bending direction, which indicates that the four capacitance structures of the flexible sensor may effectively prevent the effect of the wrinkles.

Figure 14:
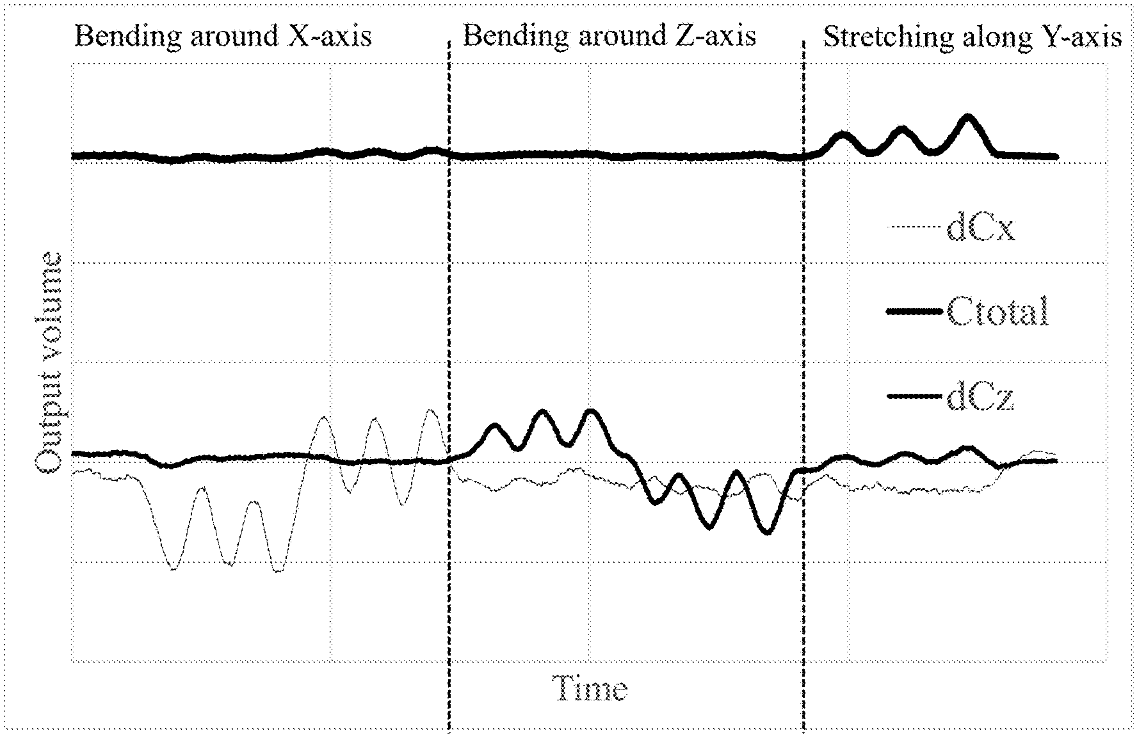
FIG. 14 is a schematic diagram illustrating curves of the flexible sensor in FIG. 13.

FIG. 14 is a schematic diagram illustrating curves of the flexible sensor in FIG. 13.

As shown in FIG. 14, when the sensor is deformed by bending around the axis parallel to the short-axis direction (i.e., the X-axis direction), dCx may change significantly with the bending angle, while Ctotal and dCz remain stable. When the sensor is deformed by bending around the axis parallel to the thickness direction (i.e., the Z-axis direction), dCz may change significantly with the bending angle, while Ctotal and dCx remain stable. When the sensor is deformed by stretching and compression along the long-axis direction of the flexible substrate (i.e., Y-axis direction), Ctotal changes significantly with the length of stretching or compression, while dCx and dCz remain stable. As a result, when the sensor undergoes the bending deformation, the output parameters Ctotal, dCx, and dCz relating to the capacitance in the sensor maintain a high degree of independence and stability, which enables the processing device to recognize different dimensions of deformation based on Ctotal, dCx, and dCz, respectively.

In some embodiments, when the sensor is in free bending motion (i.e., the sensor has a compound deformation), dCx, dCz, and Ctotal all change, and at this time, the free bending motion of the sensor may be decoupled into the bending deformation around the axis parallel to the thickness direction, the bending deformation around the axis parallel to the short-axis direction, and the stretching or compressive deformation along the long-axis direction, thereby restoring the actual bending motion of the sensor.

By decoupling the raw data to obtain decoupled data, the composite deformation of the first strain sensor may be decoupled into separate deformations in each degree of freedom. The decoupled data corresponding to each degree of freedom may be maintained with a high degree of independence and stability, thereby improving the accuracy and sensitivity of the deformation obtained in at least two degrees of freedom.

The embodiments of the present disclosure may measure the deformation of a plurality of degrees of freedom (e.g., three dimensions including the bending around the X-axis, bending around the Z-axis, and stretching along the Y-axis) by a single sensor to realize the detection of posture data of the finger in a plurality of dimensions, which is conducive to the simplification of the preparation process and the miniaturization of the design while improving the detection accuracy.

Figure 15:
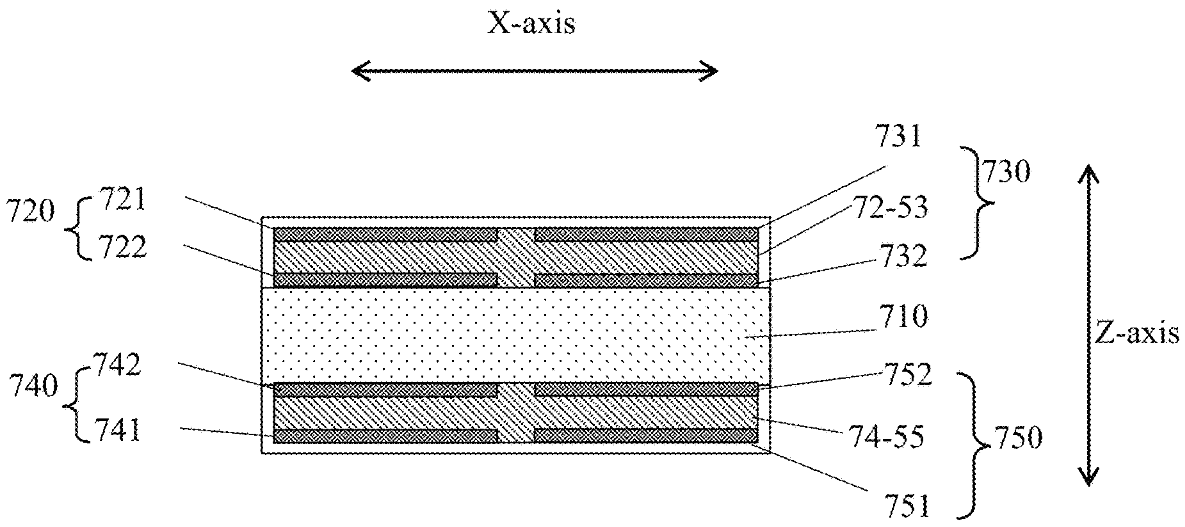
FIG. 15 is a schematic diagram illustrating a cross-sectional view of a first strain sensor according to some embodiments of the present disclosure.

FIG. 15 is a schematic diagram illustrating a cross-sectional view of a first strain sensor according to some embodiments of the present disclosure.

As shown in FIG. 15, in some embodiments, each capacitance structure includes a second conductive layer, an intermediate layer, and a first conductive layer stacked sequentially away from the flexible substrate 710 in a thickness direction. For example, the first capacitance structure 720 includes the second conductive layer 722, the intermediate layer 72-53, and the first conductive layer 721 stacked sequentially away from the flexible substrate 710. The second capacitance structure 730 includes the second conductive layer 732, the intermediate layer 72-53, and the first conductive layer 731 stacked sequentially away from the flexible substrate 710. The third capacitance structure 740 includes the second conductive layer 742, the intermediate layer 74-55, and the first conductive layer 741 stacked sequentially away from the flexible substrate 710. The fourth capacitance structure 750 includes the second conductive layer 752, the intermediate layer 74-55, and the first conductive layer 751 stacked sequentially away from the flexible substrate 710. In some embodiments, the intermediate layer is between the first conductive layer and the second conductive layer.

In some embodiments, the first conductive layer and the second conductive layer of each capacitance structure include clastic conductive material, and the elastic conductive material may cause the first conductive layer and the second conductive layer to be electrically conductive and may return to the initial shape when the external force disappears. In some embodiments, the elastic conductive material includes but is not limited to, a conductive adhesive film, a conductive ink, a conductive polymer material, a conductive gel, a liquid metal, or the like. In some embodiments, the first conductive layer and the second conductive layer include the conductive adhesive film, and the conductive adhesive film is made by mixing the conductive particles with the polymeric material. In some embodiments, the polymeric material includes but is not limited to, silicone, rubber, resin, etc. In some embodiments, the first conductive layer and the second conductive layer include the conductive ink, the conductive ink being made by mixing the conductive particles with an ink material, and the conductive ink being capable of being prepared by printing to obtain a pattern having electrical conductivity. In some embodiments, the first conductive layer and the second conductive layer include the conductive polymer material, the conductive gel, the liquid metal, or the like. In some embodiments, the conductive polymeric material includes, but is not limited to, polypyrrole, poly(3,4-ethylenedioxythiophene)-polystyrene sulfonate (PEDOT: PSS,), or the likc.

In some embodiments, the elastic conductive material includes an clastic material that is internally filled with conductive particles. The electrical conductivity of the first conductive layer and the second conductive layer may be adjusted by adjusting the density of the conductive particles filled within the clastic material. In some embodiments, the elastic material includes silicone, rubber, resin, polydimethylsiloxane (PDMS), polyurethane, styrene-butadiene-styrene (SBS), or the like. In some embodiments, the conductive particles include carbon nanotubes such as metal powder and carbon powder, silver nanowires, carbon black, graphite powder, graphene, or the like.

In some embodiments, the intermediate layer includes an elastic insulating material, and the capacitance structure is a capacitor structure. For example, the clastic insulating material includes silicone, rubber, polydimethylsiloxane (PDMS), thermoplastic polyurethane (TPU), or the like. In some embodiments, the intermediate layer includes a high-resistance elastic material. The resistivity of the intermediate layer may be greater than the resistivity of the first conductive layer and the resistivity of the second conductive layer by more than 1000 times. At this time, the capacitance structure is a capacitor-resistor composite structure.

In some embodiments, the thickness of each of the first conductive layer and the second conductive layer of each capacitance structure is within a range from 1 to 100 um. In some embodiments, the width of each of the first conductive layer and the second conductive layer of each capacitance structure is within a range from 0.5 to 10 mm. In some embodiments, a distance between the first conductive layer 721 of the first capacitance structure 720 and the first conductive layer 731 of the second capacitance structure 730 is within a range from 0.02 to 2 mm. In some embodiments, a distance between the second conductive layer 721 of the first capacitance structure 720 and the second conductive layer 732 of the second capacitance structure 730 is within a range from 0.02 to 2 mm. In some embodiments, a distance between the first conductive layer 741 of the third capacitance structure 740 and the first conductive layer 751 of the fourth capacitance structure 750 is within a range from 0.02 to 2 mm. In some embodiments, a distance between the second conductive layer 742 of the third capacitance structure 740 and the second conductive layer 752 of the fourth capacitance structure 750 is within a range from 0.02 to 2 mm.

In some embodiments, the conductivity of the first conductive layer is greater than the conductivity of the intermediate layer.

The conductivity refers to a parameter used to characterize the difficulty of the flow of electric charge in a substance. Since the conductivity of the first conductive layer is greater than the conductivity of the second conductive layer, the first conductive layer has better conductivity. Thus, the resistance of the first conductive layer is less than the resistance of the second conductive layer. It should be noted that, in the present disclosure, the resistance of a component refers to the resistance between two surfaces of the component spaced apart in the thickness direction of the flexible substrate 710. The resistance of the first conductive layer refers to the resistance between two surfaces of the first conductive layer that are spaced apart in the thickness direction of the flexible substrate 710, and the resistance of the second conductive layer refers to the resistance between two surfaces of the second conductive layer that are spaced apart in the thickness direction of the flexible substrate 710. In some embodiments, the conductivity of the first conductive layer may be more than 100 times the conductivity of the second conductive layer. In some embodiments, by setting the density of the conductive particles filled within the elastic material of the first conductive layer greater than the density of the conductive particles filled within the clastic material of the second conductive layer, the conductivity of the first conductive layer may be made greater than that of the second conductive layer.

When the capacitance structure (e.g., the first capacitance structure 720, the second capacitance structure 730, the third capacitance structure 740, and the fourth capacitance structure 750) is a capacitor-resistor composite structure or a single capacitor structure, the resistance between the two surfaces of the intermediate layer spaced apart in the thickness direction of the flexible substrate 710 should not be too small, to facilitate the subsequent measurement of the resistance and the analysis of the change in the value of the resistance. In some embodiments, the resistance between the two surfaces of the intermediate layer that are spaced apart in the thickness direction of the flexible substrate 710 is greater than 0.8 MΩ. For example, when the capacitance structure (e.g., the first capacitance structure 720, the second capacitance structure 730, the third capacitance structure 740, and the fourth capacitance structure 750) is a capacitor-resistor composite structure, the resistance between two surfaces of the intermediate layer that are spaced apart in the thickness direction of the flexible substrate 710 may be within a range from 0.8 MΩ to 1150 GΩ. As another example, when the capacitance structure (e.g., the first capacitance structure 720, the second capacitance structure 730, the third capacitance structure 740, and the fourth capacitance structure 750) is a single capacitor structure, the resistance between two surfaces of the intermediate layer that are spaced apart in the thickness direction of the flexible substrate 710 may be greater, for example, the resistance may be greater than 1150 GΩ.

By setting the resistance between two surfaces of the intermediate layer that are spaced apart in the thickness direction of the flexible substrate 710 to be greater than 0.8 MΩ, the intermediate layer can be made conductive and have a sufficiently high resistance, thereby ensuring that the measurement of the resistance of the intermediate layer and the analysis of the change in the value of the resistance can accurately reflect the bending of the first strain sensor 700.

In some embodiments, the relative dielectric constant of the intermediate layer is greater than 2. The relative dielectric constant is a physical parameter that characterizes the dielectric or polarization properties of a dielectric material. The value of the relative dielectric constant is equal to a ratio of the capacitance of a capacitor made with the dielectric material to the capacitance of a capacitor of the same size made with vacuum. The value of the relative dielectric constant is also a characterization of the electrical storage capacity of the material, also referred to as relative permittivity. Substances with a relative dielectric constant greater than 2 are polar substances, which means that the intermediate layer with a relative dielectric constant greater than 2 has a certain electrical storage capacity. Thus, the intermediate layer may be equated to a parallel combination of a resistive element and a capacitance element.

In some embodiments, the relative dielectric constant of the intermediate layer may also be greater than or equal to 4. In some embodiments, the relative dielectric constant of the intermediate layer is greater than 5. In some embodiments, the relative dielectric constant of the intermediate layer is greater than 10.

Setting the intermediate layer to have a relative dielectric constant greater than 2 allows the intermediate layer to be both a resistive element and a capacitance element. Both the capacitance and resistance of the intermediate layer change in response to the deformation of the flexible substrate 710 during the bending of the first strain sensor 700. Thus, the parameters of the intermediate layer relating to the capacitance and resistance may reflect the bending of the first strain sensor 700. The simultaneous presence of the capacitance and resistance in this embodiment reflects the bending of the first strain sensor 700, which results in a significant increase in the sensitivity and accuracy of the first strain sensor 700.

In addition, by setting the resistance between two surfaces of the intermediate layer that are spaced apart in the thickness direction of the flexible substrate 710 to be greater than 0.8 MΩ, the intermediate layer may embody both good resistive and capacitance properties, to ensure the sensitivity and accuracy of the first strain sensor 700.

In some embodiments, two capacitance structures on the same side of the surface of the flexible substrate 710 may share a first conductive layer, with the second conductive layers of the two capacitance structures spaced apart in a direction along a short-axis direction of the flexible substrate 710. In some embodiments, more conductive layers (e.g., a third conductive layer, etc.) may be stacked along the thickness direction of each capacitance structure, which may effectively improve the sensitivity of the sensor in detecting the deformation of each degree of freedom. For example, each capacitance structure includes a second conductive layer, a second intermediate layer, a third conductive layer, a first intermediate layer, and a first conductive layer that are stacked sequentially away from the flexible substrate 710 in the thickness direction. The third conductive layer, the first conductive layer, and the second conductive layer have the same parameters; the second intermediate layer, the first intermediate layer, and the intermediate layer have the same parameters.

In some embodiments, the at least two target finger joints further include at least two proximal interphalangeal joints corresponding to at least two metacarpophalangeal joints. The finger joint angles may be determined based on sensor data corresponding to at least two metacarpophalangeal joints and at least two corresponding proximal interphalangcal joints. At this time, the at least two strain sensors include at least two second strain sensors disposed at the at least two proximal interphalangeal joints, and each of the second strain sensors is configured to measure the deformation of the proximal interphalangeal joint corresponding thereto in a single degree of freedom. The deformation of the proximal interphalangeal joints in a single degree of freedom refers to deformation information of the proximal interphalangeal joints that occurs when the proximal interphalangeal joints undergo bending.

The second strain sensor is a strain sensor arranged at the proximal interphalangeal joint to capture deformation (e.g., bending) of the proximal interphalangeal joint in a single degree of freedom. In some embodiments, the second strain sensor may be a single-axis sensor, which may include a variety of flexible bending sensors, such as inductive sensors, resistive sensors, capacitance sensors, fiber optic sensors, or the like. Merely by way of example, the second strain sensor includes an inductive sensor, the inductance of the inductive sensor being capable of varying with the deformation of an interphalangeal joint, such as a proximal interphalangcal joint. Specifically, the inductive sensor deforms with the movement of the interphalangeal joint, and its inductance changes in response to the deformation of the inductive sensor. By collecting the parameters of the inductive sensor relating to inductance and analyzing the changes, the bending of the inductive sensor (e.g., the bending angle, the bending direction, etc.) may be calculated more accurately. For example, the electrical quantity of the inductance of the inductive sensor is proportional to the deformation amount of the inductive sensor, whereby a change in the electrical quantity of the inductance of the inductive sensor characterizes the deformation degree or flexion degree of the interphalangeal joint. Since the interphalangeal joint corresponds to only one degree of freedom of bending, the single-axis sensor (e.g., the inductive sensor) used to measure the movement of the interphalangeal joint is simple in structure and low in product cost. Alternatively, the second strain sensor may be arranged only at the interphalangeal joint closest to the metacarpophalangeal joint of each finger of the user, thereby simplifying the structure and reducing the cost of the product while ensuring the collection accuracy of the deformation data.

In some embodiments of the present disclosure, considering that the proximal interphalangeal joint corresponds to only one degree of freedom of bending, the single-axis sensor is used to measure the sensor data of the proximal interphalangcal joint during bending, which is simple in structure and low in cost.

In 620, the processing device 410A may obtain a first mapping relationship. The first mapping relationship reflects a relationship between sensor data corresponding to the at least two target finger joints and the joint angles of the at least two target finger joints, and the at least two target finger joints include at least two adjacent metacarpophalangeal joints of the user.

The first mapping relationship may be represented in the form of a mapping function, a machine learning model, etc. For example, the first mapping relationship may be a mapping function (e.g., a polynomial) with the sensor data as the independent variable and the joint angles as the dependent variables. As another example, the first mapping relationship may be a machine learning model, the machine learning model taking sensor data as input and joint angles as output. For example, the machine learning model may be a recurrent neural network (RNN) or other deep neural network models.

In some embodiments, the first mapping relationship includes a mapping function or machine learning model corresponding to each of the target finger joints. For example, for a specific target finger joint, the corresponding mapping function takes the sensor data of all target finger joints as independent variables and the joint angle of the specific target finger joint as a dependent variable. As another example, for a specific target finger joint, an input of the corresponding machine learning model is the sensor data of all target finger joints, and an output is the joint angle of the specific target finger joint.

In some embodiments, the first mapping relationship may be determined by the processing device 410A or the processing device 410B based on a plurality of data samples. More descriptions regarding generating the first mapping relationship may be found in FIG. 19 and its related description.

In 630, the processing device 410A may determine, based on the first sensor data and the first mapping relationship, the first joint angle of each target finger joint.

Figure 3:
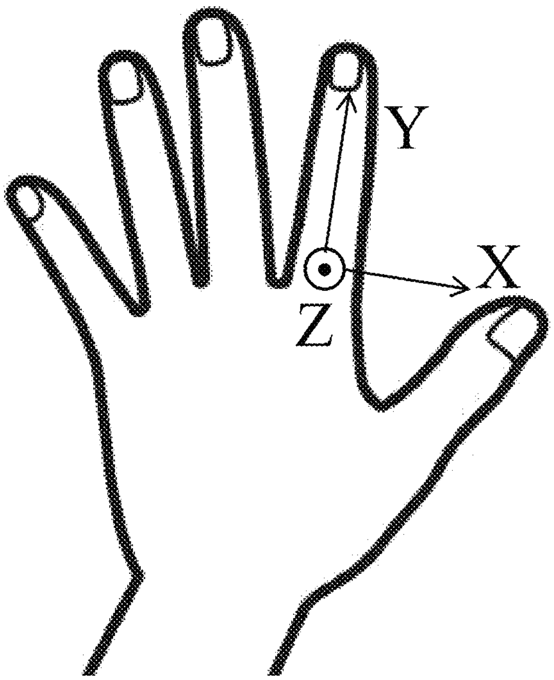
FIG. 3 is a schematic diagram illustrating a three-dimensional coordinate system of the hand of a user according to some embodiments of the present disclosure.

The first joint angle of the target finger joint may include an angle thereof in any one or more degrees of freedom. For example, the first joint angle includes a bending angle and/or a swinging angle. The bending angle refers to an angle at which the target finger joint rotates around the X-axis as shown in FIG. 3. The swing angle refers to the angle at which the target finger joint rotates around the Z-axis shown in FIG. 3. In some embodiments, when the target finger joint is a metacarpophalangeal joint, the first joint angle includes both the bending angle and the swing angle. When the target finger joint is a proximal interphalangeal joint, the first joint angle includes only the bending angle.

In some embodiments, the processing device 410A may input the first sensor data into the first mapping relationship, and the first mapping relationship may output the first joint angle of the target finger joint after processing the first sensor data. For example, when the first mapping relationship is represented by a mapping function, the first sensor data may be substituted into the mapping function to obtain the first joint angle. As another example, when the first mapping relationship is represented by a trained machine learning model, the first sensor data may be input into the machine learning model to obtain the first joint angle.

In some embodiments, the target finger joint may include a portion of the finger joints of the user or all of the metacarpophalangeal joints and all the proximal interphalangeal joints of the user, as described in operation 610. The processing device 410A may determine the first joint angle of each target finger joint of all the target finger joints based on the first mapping relationship. In some embodiments, the processing device 410A may determine the first joint angles of a portion of the target finger joints based on the first mapping relationship. For example, the first joint angles determined by the processing device 410A may be the angles of a portion of the metacarpophalangeal joints, and sensor data in the first sensor data relating to other metacarpophalangcal joints and/or proximal interphalangeal joints may be regarded as auxiliary information for improving the accuracy of the first joint angles. Merely by way of example, first sensor data relating to a plurality of finger joints may be sequentially used as input to the first mapping relationship, and the mapping relationship may be configured to output only the first joint angle corresponding to the first input finger joint angle. As another example, the processing device 410A may provide a selection window via an interactive interface, and the user may select one or more target finger joints on the selection window. The processing device 410A may output the first joint angle of the target finger joint selected by the user based on the received feedback.

In some embodiments, the glove body includes fabric wrapped around each finger of the user and fabric disposed between adjacent fingers. The clastic modulus of the fabric disposed between the adjacent fingers is less than the clastic modulus of the fabric wrapped around each finger. The fabric between adjacent fingers may be referred to as an elastic fabric structure (e.g., the clastic fabric structure 170 shown in FIG. 1). More descriptions regarding the clastic fabric structure may be found in FIG. 1 and related descriptions thereof. In some embodiments, parameters characterizing the fabric (i.e., the elastic fabric structure) between adjacent fingers can influence the strength of the coupling relationship between the finger joints of adjacent fingers. For example, the smaller the clastic modulus of the fabric between the adjacent fingers, the less likely the fabric on the adjacent fingers is to be tugged, and therefore the smaller the coupling relationship between the finger joints of the adjacent fingers. The processing device 410A may further determine the first joint angle based on the characteristic parameter.

In some embodiments, the processing device 410A may obtain the value of the characteristic parameter of the fabric between adjacent fingers, the characteristic parameter including at least one of an elastic coefficient, a transverse dimension, or a resilience coefficient. The first mapping relationship may further reflect a relationship between the characteristic parameter, sensor data corresponding to the at least two target finger joints, and the joint angles of the at least two target finger joints. Therefore, the first joint angle of each target finger joint may be further determined based on the value of the characteristic parameter of the fabric between adjacent fingers. For example, the first mapping relationship may be represented by a machine learning model, the training data for which includes sample sensor data of sample finger joints and sample values of characteristic parameters of a sample fabric between adjacent sample fingers. Correspondingly, when determining the first joint angle using the machine learning model, the processing device 410A may input the first sensor data and the values of the characteristic parameters (e.g., the elastic coefficient, the transverse dimension, or the resilience coefficient, or the like) of the fabric between adjacent fingers into the model, and the model outputs the first joint angle of the target finger joint.

In some embodiments of the present disclosure, taking into account the influence of the fabric characteristic of adjacent fingers on the coupling relationship between finger joints may make the first mapping relationship more in line with the actual situation, and make the first joint angle more accurate.

In some embodiments, the coupling relationship between the target finger joints is related to the distance between the target finger joints. Merely by way of example, different users have different palm sizes, different distances between the metacarpophalangeal joints and interphalangeal joints, and different gestures or hand movements that may be made (e.g., different bending degrees of the finger joints). As another example, the closer the distance, the stronger the coupling between the finger joints. Thus, the first joint angle may be further determined based on the distance information.

In some embodiments, the glove body may include position sensors arranged at each of the target finger joints, and the processing device 410A may further determine, based on position data collected by a position sensor arranged at each of the target finger joints, distance information between at least two strain sensors. The first mapping relationship may further reflect a relationship between a distance between the at least two strain sensors, the sensor data corresponding to the at least two target finger joints, and the joint angles of the at least two target finger joints. Thus, the first joint angle of each of the target finger joints may be further determined based on the distance information. For example, the first mapping relationship may be represented by a machine learning model, the training data of which includes sample sensor data of the sample finger joint and sample distance information between at least two sample strain sensors. Correspondingly, when determining the first joint angle using the machine learning model, the processing device 410A may input the distance information between the at least two strain sensors into the model, which outputs the first joint angle of the target finger joint.

In some embodiments, the first mapping relationship may reflect a mapping relationship between the characteristic parameter of the elastic fabric structure, the distance between the at least two strain sensors, the sensor data corresponding to the at least two target finger joints, and the joint angles of the at least two target finger joints. The processing device 410A may further determine the first joint angle based on the value of the characteristic parameter and the distance information.

It should be noted that the foregoing description of process 600 is for illustration purposes only and is not intended to limit the scope of the present disclosure. For those of ordinary skill in the art, a wide variety of variations and modifications may be made under the teachings of the present disclosure. However, these variations and modifications do not depart from the scope of the present disclosure. In some embodiments, process 600 may be accomplished with one or more additional operations not described and/or without one or more of the operations discussed above. In addition, the order of the process 600 is not limiting. For example, process 600 may include operations for generating a mapping relationship. As another example, process 600 may include an operation for correcting the mapping relationship. More descriptions regarding correcting the mapping relationship may be found in FIG. 16 and/or FIG. 17 and their related descriptions, which may not be repeated here. As yet another example, process 600 may further include the operation for determining the second joint angle of the distal interphalangeal joint based on the second mapping relationship.

In some embodiments, when the at least two target finger joints include proximal interphalangeal joints, for each proximal interphalangeal joint, the processing device 410A may determine, based on the second mapping relationship and the first joint angle of the proximal interphalangcal joint, a second joint angle of the distal interphalangeal joint corresponding to the proximal interphalangeal joint. The second mapping relationship reflects a relationship between the joint angle of the proximal interphalangeal joint and the joint angle of the distal interphalangeal joint. Because the distal interphalangeal joint exhibits a follow-up to the proximal interphalangeal joint, the second joint angle of the distal interphalangeal joint may be determined based on the first joint angle of the corresponding proximal interphalangeal joint The second mapping relationship may be represented by a mapping function or a trained machine learning model. For example, the second mapping relationship may be a mapping function representing a relationship between the first joint angle and the second joint angle, and the processing device 410A may input the first joint angle into the mapping function to obtain the second joint angle. As another example, the second mapping relationship may be a trained machine learning model into which the processing device may input the first joint angle and/or the first sensor data to obtain the second joint angle. In some embodiments, the second mapping relationship may be obtained by a data-fitting algorithm or a machine-learning algorithm. For example, the second mapping relationship may be represented by a machine learning model whose training data includes sample first joint angles of sample proximal interphalangeal joints and/or sample first sensor data, and whose training label includes sample second joint angles of sample distal interphalangeal joints corresponding to the sample proximal interphalangeal joints.

According to some embodiments of the present disclosure, by taking into account the linkage between the proximal interphalangeal joint and the distal interphalangeal joint, the second joint angle of the distal interphalangeal joint may be determined based on the first joint angle of the proximal interphalangcal joint, which avoids arranging sensors at the distal interphalangcal joints, thereby saving costs. Additionally, through the second mapping relationship, after the first joint angle of the proximal interphalangeal joint is determined, the second joint angle of the distal interphalangcal joint corresponding to the proximal interphalangeal joint may be determined quickly and accurately.

In some embodiments, since the first mapping relationship is determined based on a plurality of data samples, it reflects the relationship between the sensor data and the joint angles of the target finger joints in general. Due to individual differences, when different users wear the glove to perform the same action, the first sensor data may be different. For example, the first mapping relationship may be used to determine a relationship between the first sensor data in a predetermined data range and the joint angles of the target finger joints. Whereas the first sensor data of some users may exceed the predetermined data range. Therefore, the processing device 410A may correct the first mapping relationship for a specific user and utilize the corrected first mapping relationship to determine the first joint angle of each target finger joint of the user.

Figure 16:
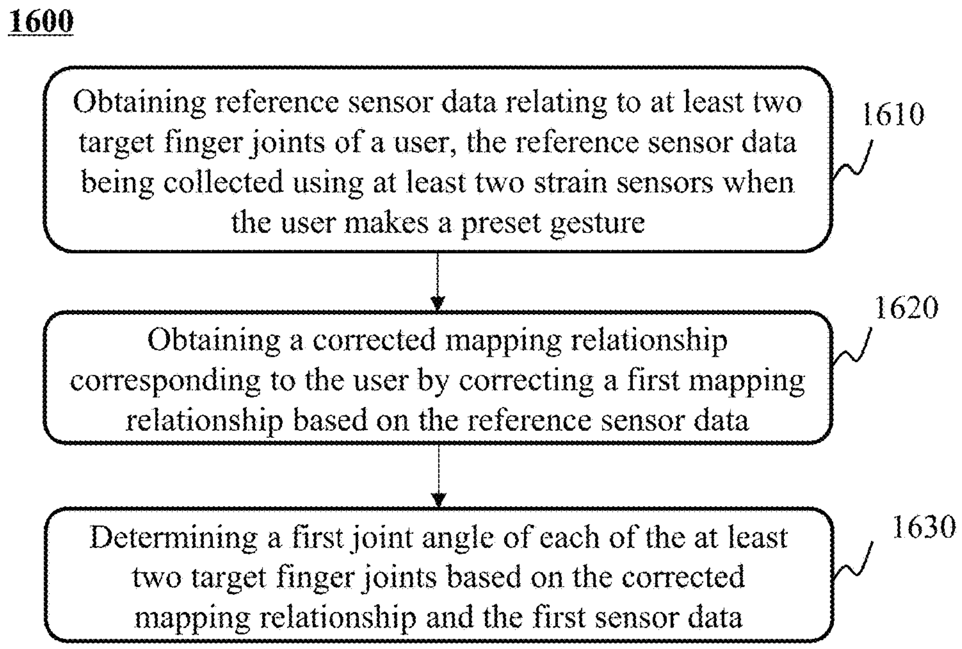
FIG. 16 is a flowchart illustrating another process for determining a finger joint angle according to some embodiments of the present disclosure.

FIG. 16 is a flowchart illustrating another process for determining a finger joint angle according to some embodiments of the present disclosure. In some embodiments, process 1600 may be performed by the processing device 410A. In some embodiments, operation 630 in process 600 may be realized by process 1600. As shown in FIG. 16, process 1600 may include the following operations.

In 1610, the processing device 410A may obtain reference sensor data relating to at least two target finger joints of the user. The reference sensor data may be collected using at least two strain sensors when the user makes a preset gesture.

The preset gesture may be various preset hand movements reflecting finger postures or deformations. In some embodiments, the preset gesture may be used to reflect upper and lower limits of the deformation (e.g., bending, swinging) of the fingers (e.g., maximum bending angles of the fingers, a maximum angle between two adjacent fingers, etc.). For example, the preset gesture may include a closing and stretching action, an opening action, a fist-clenching action, etc. of the palm. In some embodiments, deformations in different degrees of freedom may correspond to different preset gestures. For example, for deformations in the degree of freedom of bending, the preset gesture may include the fist-clenching action and the opening action (or the closing and stretching action). The fist-clenching action corresponds to a maximum joint angle that the finger joint can bend, and the opening action (or the closing and stretching action) corresponds to a minimum joint angle that the finger joint can bend. As another example, for the deformation in the degree of freedom of swinging, the preset gesture may include the closing and stretching action and the opening action. The closing and stretching action corresponds to a minimum joint angle that the finger joint can swing, and the opening action corresponds to a maximum joint angle that the finger joint can swing. The preset gesture may be displayed to the user in the form of an image, a video, or in other forms, and the user may make the preset gesture while wearing the glove body.

In 1620, the processing device 410A may obtain a corrected mapping relationship corresponding to the user by correcting the first mapping relationship based on the reference sensor data.

In some embodiments, when the user makes different preset gestures, the sensor data collected by the strain sensors (e.g., the first strain sensors and the second strain sensors) arranged at different target finger joints may be used as reference sensor data for correcting the first mapping relationship. For example, the preset gesture may be the fist-clenching action that corresponds to a maximum joint angle of each of one or more target finger joints (or all the finger joints). The processing device 410A may obtain the reference sensor data relating to at least two target finger joints during the fist-clenching action and determine whether the reference sensor data is outside a predetermined data range. In response to determining that the reference sensor data is outside the predetermined data range, the processing device 410A may update the predetermined data range. Merely by way of example, the deformation degree (e.g., bending degree) of the strain sensor at the target finger joint is the greatest when the target finger joint is at the maximum joint angle, and the processing device 410A may replace the upper limit of the predetermined data range with the reference sensor data at this time. As another example, the predetermined gesture may be the opening action, the opening action corresponding to a minimum joint angle of each of one or more target finger joints (or all the finger joints). The processing device 410A may obtain reference sensor data relating to the at least two target finger joints during the opening action and determine whether the reference sensor data is outside the predetermined data range. In response to determining that the reference sensor data is outside the predetermined data range, the processing device 410A may update the predetermined data range. For example, the deformation degree (e.g., the bending degree) of the strain sensor at the target finger joint is the smallest when the target finger joint is at the minimum joint angle, and the processing device 410A may replace the lower limit of the predetermined data range with the reference sensor data at this time.

After updating the predetermined data range, the processing device 410A may determine the corrected mapping relationship based on the updated predetermined data range. Merely by way of example, when the first mapping relationship is represented by a mapping function, the processing device 410A may obtain an updated mapping function by performing data fitting calculations based on the updated predetermined data range, and the updated mapping function may be used as the corrected mapping relationship.

In some embodiments, the first mapping relationship may be represented by a trained machine learning model, and the first mapping relationship may be corrected based on a migration learning algorithm. The trained machine learning model corresponding to the current first mapping relationship may be referred to simply as a generalized model.

In some embodiments, the processing device 410A may use the generalized model as an initial pre-training model and perform a further training process on the initial pre-training model. Training samples may be determined based on the reference sensor data, and training labels may be reference first joint angles corresponding to the reference sensor data (e.g., a finger joint angle of a certain gesture). In the training process, a value of the loss function may be determined based on the difference between the output of the initial pre-training model and the training labels. Parameters of the initial pre-training model may be iteratively updated based on the value of the loss function until training ending conditions are satisfied (e.g., the loss function converges, a specific count of iterations has been performed, etc.) to obtain an updated initial pre-training model. The processing device 410A may use the updated initial pre-training model as the corrected first mapping relationship, thereby realizing the correction of the first mapping relationship using the migration learning algorithm.

In some embodiments, the processing device 410A may train the generalized model for different users or user groups (e.g., male/female, elderly/children, and other users or groups) to obtain corrected first mapping relationships (i.e., a corrected generalized models) corresponding to the different users or user groups. In practical applications, different models (e.g., generalized models or the corrected generalized models) may be used for different users to determine a first joint angle of a target finger joint based on the first sensor data.

In 1630, the processing device may determine the first joint angle of each target finger joint based on the corrected mapping relationship and the first sensor data. For example, the processing device 410A may input the first sensor data into the corrected mapping relationship such that the corrected mapping relationship may output the first joint angle of the target finger joint after processing the first sensor data.

According to some embodiments of the present disclosure, the first mapping relationship is corrected based on the reference sensor data, thereby obtaining a corrected mapping relationship that better matches the current user, which in turn makes the first joint angle more accurate.

In some embodiments, process 1600 may be executed when the user first wears the glove system, and after the corrected mapping relationship corresponding to the user is determined, the corrected mapping relationship may be stored for use by the user every time he/she wears the glove system.

In some embodiments, the first mapping relationship may be represented by a mapping function, and the processing device 410A may correct the mapping function based on the distance information between the at least two strain sensors and use the corrected mapping function to determine the first joint angle of each target finger joint.

Figure 17:
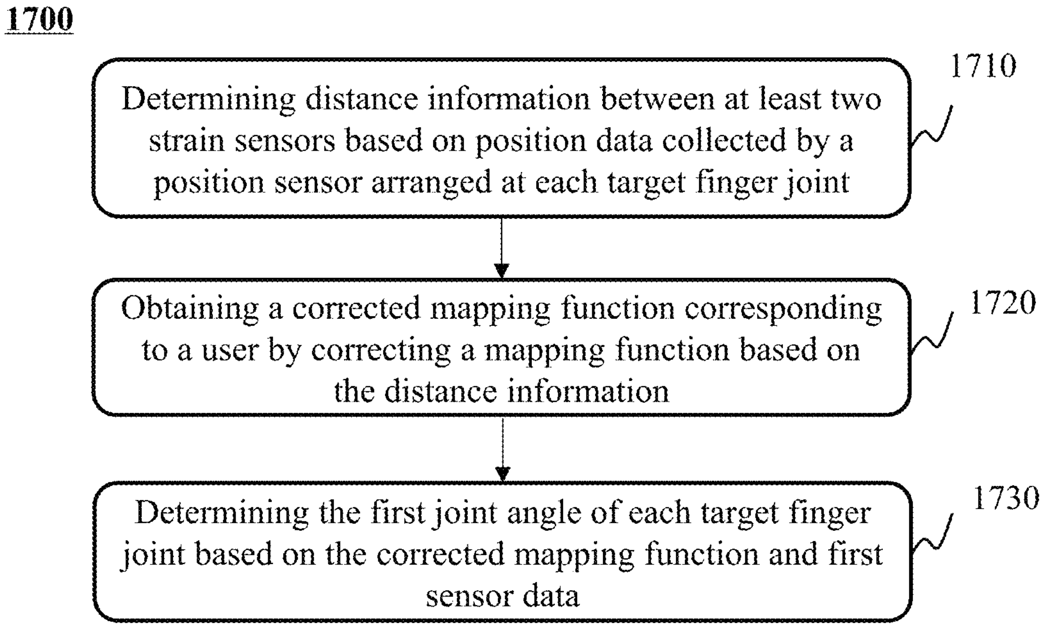
FIG. 17 is a flowchart illustrating another process for determining a finger joint angle according to some embodiments of the present disclosure.

FIG. 17 is a flowchart illustrating another process for determining a finger joint angle according to some embodiments of the present disclosure. In some embodiments, process 1700 may be performed by the processing device 410A. In some embodiments, operation 630 in process 600 may be realized by process 1700. As shown in FIG. 17, process 1700 may include the following operations.

In 1710, the processing device 410A determines distance information between at least two strain sensors based on position data collected by a position sensor arranged at each target finger joint.

The linkage or coupling relationship between at least two target finger joints is related to the distance between the target finger joints. Merely by way of example, different users have different palm sizes, different distances between the metacarpophalangcal joint and interphalangeal joint, and can make different gestures or hand actions (e.g., different degrees of bending of the finger joints). As another example, the closer the distance, the stronger the coupling between the finger joints. In such cases, the mapping function may be corrected based on the distance information between the target finger joints.

In some embodiments, the glove body is provided with a position sensor and a strain sensor corresponding to each target finger joint, and a relative positional relationship between the position sensor and the strain sensor is known. For any two strain sensors, a distance between the two strain sensors may be determined based on the position data collected by the corresponding position sensors, and the relative positional relationship between the position sensors and the strain sensors. The distance between the two strain sensors may be used to represent the distance between two target finger joints corresponding to the two strain sensors.

In 1720, the processing device 410A may obtain a corrected mapping function corresponding to the user by correcting the mapping function based on the distance information.

In some embodiments, the mapping function includes relationship coefficients reflecting the strength of coupling relationships (e.g., coupling degrees) between different target finger joints, and these relationship coefficients may be adjusted based on the distance information to obtain a corrected mapping function. For example, the mapping function corresponding to the first target joint takes the sensor data corresponding to all the target joints as an independent variable, takes the first joint angle of the first target joint as a dependent variable, and includes a relationship coefficient between each other target joint and the first target joint. When the distance between a strain sensor corresponding to a certain target joint and the strain sensor corresponding to the first target joint is less than a first distance threshold, which indicates that the coupling relationship between the target joint and the first target joint is strong, the relationship coefficient between the target joint and the first target joint may be increased. When the distance is greater than a second distance threshold, which indicates that the coupling relationship is weak, the value of the relationship coefficient between the target joint and the first target joint may be reduced. The first distance threshold is less than the second distance threshold. In some embodiments, the first distance threshold and the second distance threshold may be set by the user or determined based on statistical data. For example, a distribution of distances between sample strain sensors corresponding to data samples used to determine the mapping function may be analyzed to determine the first distance threshold and the second distance threshold.

In 1730, the processing device 410A may determine the first joint angle of each target finger joint based on the corrected mapping function and the first sensor data. For example, the processing device 410A may input the first sensor data to the corrected mapping function such that the corrected mapping function may output the first joint angle of the target finger joint after processing the first sensor data.

In some embodiments of the present disclosure, the influence of the distance between different finger joints (or finger joints of different users' hands) on the coupling relationship between the finger joints is considered, and the first mapping relationship is corrected according to the distance between the target finger joints of the different users. Thus, the first mapping relationship may be combined with the characteristics of the hands of the different users, which may make the first joint angle more targeted and more accurate.

In some embodiments, at least two target finger joints may include only at least two adjacent metacarpophalangeal joints of the user, and the processing device 410A may determine the first joint angle of each of the at least two adjacent metacarpophalangeal joints based on the process 600 described in FIG. 6. Further, the processing device 410A may determine a third joint angle of a proximal interphalangeal joint based on a third mapping relationship.

Figure 18:
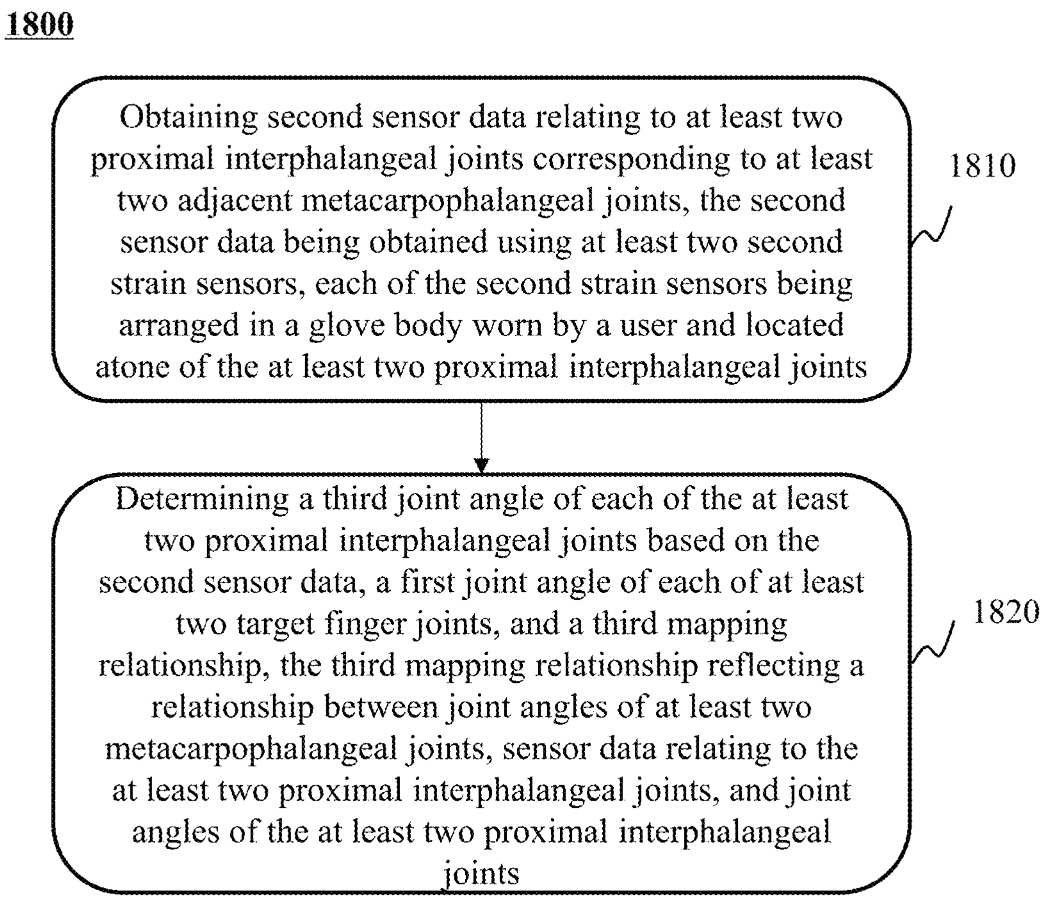
FIG. 18 is a flowchart illustrating an exemplary process for determining a third joint angle according to some embodiments of the present disclosure.

FIG. 18 is a flowchart illustrating an exemplary process for determining a third joint angle according to some embodiments of the present disclosure. In some embodiments, the process 1800 may be performed by the processing device 410A. In some embodiments, the process 1800 may be accomplished utilizing one or more additional operations/steps not described below, and/or not by one or more operations/steps discussed below. Additionally, the order of the operations/steps as shown in FIG. 18 is not limiting. As shown in FIG. 18, the process 1800 may include the following operations.

In 1810, the processing device 410A may obtain second sensor data relating to at least two proximal interphalangeal joints corresponding to the at least two adjacent metacarpophalangeal joints. The second sensor data may be obtained using at least two second strain sensors, each of the at least two second strain sensors is arranged in the glove body worn by the user and located at one of the at least two proximal interphalangeal joints.

In some embodiments, each of the at least two second strain sensors may be configured to measure the deformation of a corresponding proximal interphalangeal joint in a single degree of freedom. The deformation of the proximal interphalangeal joint in a single degree of freedom refers to information about the deformation of the proximal interphalangeal joint that occurs when the proximal interphalangeal joint undergoes bending. Descriptions regarding the second strain sensors may be found in FIG. 1 and related descriptions thereof.

In 1820, the processing device 410A may determine a third joint angle of each of the at least two proximal interphalangeal joints based on the second sensor data, the first joint angle of each of the at least two finger joints, and a third mapping relationship. The third mapping relationship may reflect a relationship between joint angles of the at least two adjacent metacarpophalangeal joints, sensor data relating to the at least two proximal interphalangcal joints, and joint angles of the at least two proximal interphalangeal joints.

The third joint angle refers to the bending angle of a proximal interphalangeal joint, for example, the bending angles of proximal interphalangeal joints of the index, middle, ring, and/or pinky fingers.

In some embodiments, there is a coupling relationship between the metacarpophalangcal joints (hereinafter referred to as a first coupling relationship), and there is a coupling relationship between the proximal interphalangeal joints and the metacarpophalangeal joints (hereinafter referred to as a second coupling relationship). For example, deformation (e.g., bending) of a particular proximal interphalangeal joint may have different degrees of linkage effect on both the metacarpophalangeal joint corresponding to the proximal interphalangeal joint and the adjacent metacarpophalangeal joints. The third mapping relation may be used to characterize the coupling relationship between the joint angle of the proximal interphalangcal joint and the joint angle of the metacarpophalangeal joint.

In some embodiments, the third mapping relationship may be obtained similarly to the first mapping relationship. In some embodiments, the third mapping relationship may be represented using a mapping function or a trained machine learning model. Taking the third mapping relationship being represented by a machine learning model as an example, the processing device 410A may input the joint angles of the at least two metacarpophalangeal joints and the sensor data of the at least two proximal interphalangeal joints into a trained machine learning model corresponding to the third mapping relationship, by which a third joint angle corresponding to each proximal interphalangeal joint is output. In some embodiments, the at least two proximal interphalangeal joints herein may be any at least two proximal interphalangcal joints, and the at least two metacarpophalangeal joints may be a portion of or all the metacarpophalangcal joints. For example, the at least two metacarpophalangeal joints may be the metacarpophalangeal joints corresponding to the proximal interphalangeal joints and one or two metacarpophalangeal joints of one or two adjacent fingers.

According to some embodiments of the present disclosure, the coupling relationship between the proximal interphalangeal joint and one or more metacarpophalangcal joints is considered, and the effect of the metacarpophalangeal joint angle is considered when determining the third joint angle of the proximal interphalangeal joint, which makes the third joint angle more accurate. In addition, in combination with the process 600 described in FIG. 6, the embodiments of the present disclosure determine joint angles corresponding to different types of finger joints (metacarpophalangeal joints and proximal interphalangeal joints) based on different mapping relationships (the first mapping relationship and the third mapping relationship), which may be combined with different coupling relationships (the first coupling relationship and the second coupling relationship) for different types of finger joints, respectively, so as to make the joint angles more accurate.

Figure 19:
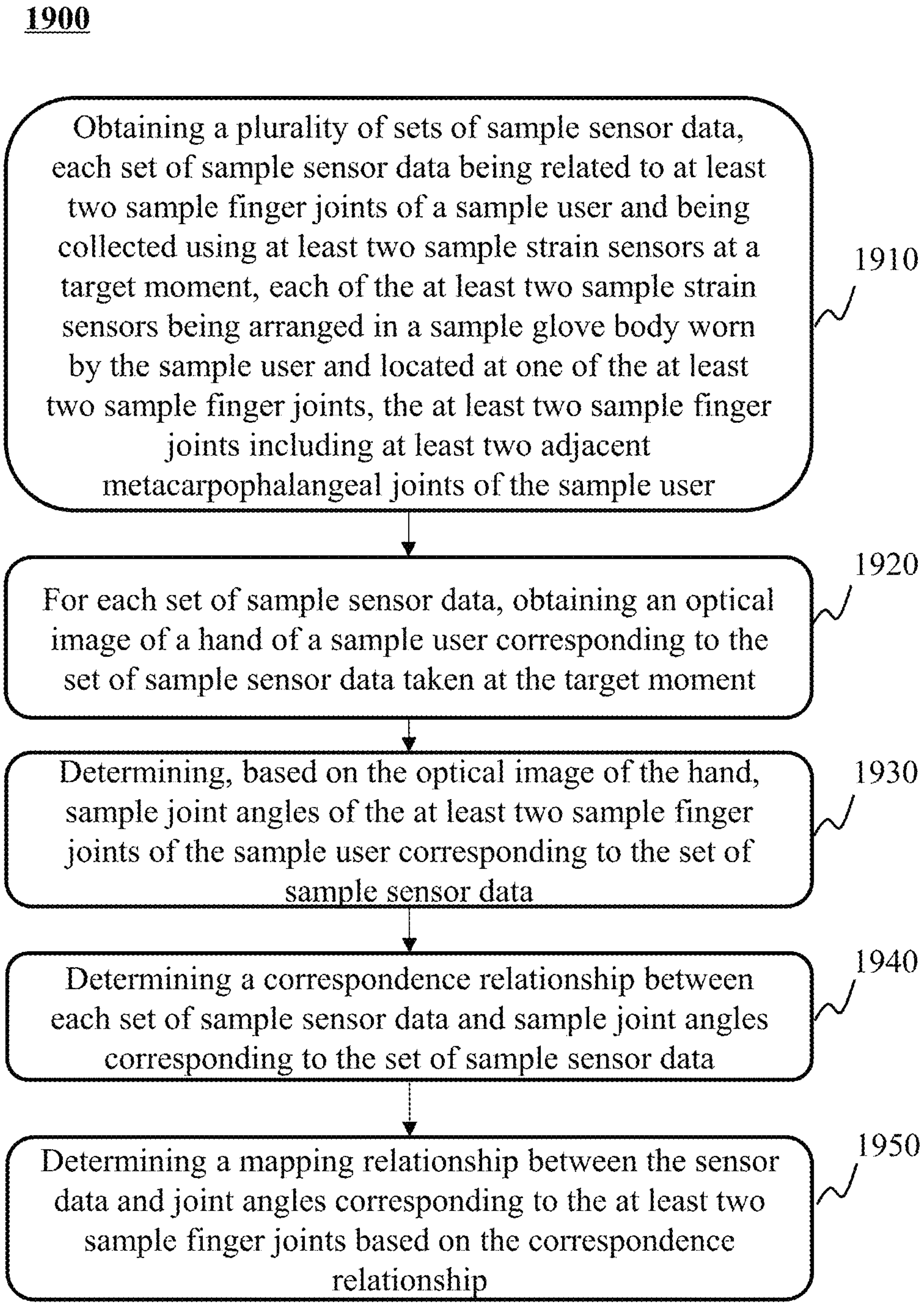
FIG. 19 is a flowchart illustrating an exemplary process for determining a correspondence relationship between sensor data and finger joint angles according to some embodiments of the present disclosure.

FIG. 19 is a flowchart illustrating an exemplary process for determining a correspondence relationship between sensor data and finger joint angles according to some embodiments of the present disclosure.

In some embodiments, process 1900 may be performed by processing device 410B. As shown in FIG. 19, process 1900 may include the following operations.

In 1910, the processing device 410B may obtain a plurality of sets of sample sensor data. Each set of sample sensor data of the plurality of sets of sample sensor data is related to at least two sample finger joints of a sample user and is collected using at least two sample strain sensors at a target moment. Each of the at least two sample strain sensors is arranged in a sample glove body worn by the sample user and located at one of the at least two sample finger joints. The at least two sample finger joints include at least two adjacent metacarpophalangeal joints of the sample user.

In the present disclosure, "sample" is used to indicate that the concepts it describes are used to determine mapping relationships (such as the first mapping relationship, the second mapping relationship, and the third mapping relationship described earlier). For example, the sample finger joint and the target finger joint described in FIG. 6 have similar meanings, but the sample finger joint is a concept involved in the process of determining the first mapping relationship, while the target finger joint is a concept involved in the process for applying the first mapping relationship.

The sample sensor data may be used to characterize posture and/or movement information of the sample finger joints of the sample user, which may be collected using at least two sample strain sensors at the target moment. Each sample strain sensor is arranged in the sample glove body worn by the sample user and located at one of the at least two sample finger joints. For example, the sample sensor data may be collected using a sample glove system that is the same as or similar to the sample glove system 100 as described in FIG. 1. The sample glove system includes a plurality of sample strain sensors, the plurality of sample strain sensors may include first sample strain sensors and second sample strain sensors arranged in the sample glove body. More descriptions regarding the sample glove system, the glove body, the first sample strain sensor, and the second sample strain sensor may be found in FIG. 1 and related descriptions thereof. In some embodiments, the sample sensor data may be historical data.

In some embodiments, the sample sensor data may be data collected by a sample strain sensor while the sample user is performing a hand movement (e.g., the sample user is mimicking a preset gesture). The target moment is the moment when a sample user makes/completes a specific gesture, which may be in the form of a timestamp. Different gestures completed by the sample user correspond to different target moments. The processing device 410B may record and/or store the sample sensor data collected by the sample strain sensors at each target moment to obtain a set of sample sensor data corresponding to each target moment.

The sample user may be any user. In some embodiments, the sample user includes a user and/or a group of users (e.g., male/female, elderly/children, etc.) with different hand characteristics (e.g., size of hand, length of fingers, etc.).

The sample finger joint may be one or a combination of finger joints (e.g., thumb, index finger, middle finger, ring finger, and pinky finger) of the sample user, such as interphalangeal joints (e.g., proximal interphalangcal joints and distal interphalangcal joints), metacarpophalangcal joints, or the like.

In some embodiments, the at least two sample finger joints include a portion of the finger joints of the sample user. The portion of finger joints may include a portion of finger joints with a coupling relationship. In some embodiments, the portion of finger joints includes a portion of finger joints that are more easily coupled or have high coupling degrees. Descriptions regarding the coupling relationship and the coupling degree may be found in FIG. 6 and will not be repeated here.

In some embodiments, the at least two sample finger joints include at least two adjacent metacarpophalangeal joints of the sample user. It will be appreciated that the adjacent metacarpophalangeal joints have a high coupling degree. The processing device 410B may determine at least two adjacent metacarpophalangeal joints of the user as the sample finger joints. In some embodiments, the at least two sample finger joints include all the metacarpophalangeal joints of the sample user.

In some embodiments, the at least two metacarpophalangeal joints include the metacarpophalangeal joints of at least one of the index, middle, and ring fingers of the sample user, and two adjacent fingers on either side thereof. For example, for an index finger, two adjacent fingers on either side thereof are the thumb and the middle fingers, and the at least two metacarpophalangeal joints include a metacarpophalangeal joint of the index finger of the sample user and metacarpophalangeal joints of the thumb and the middle fingers.

In some embodiments, the at least two metacarpophalangeal joints include the metacarpophalangeal joint of at least one of the thumb and the middle finger of the sample user and the metacarpophalangeal joint of one adjacent finger thereof. For example, for a thumb whose adjacent finger is the index finger, the at least two metacarpophalangeal joints include the metacarpophalangeal joint of the thumb of the sample user and the metacarpophalangcal joint of the index finger.

In some embodiments, the at least two sample finger joints further include at least two proximal interphalangcal joints corresponding to the at least two metacarpophalangeal joints of the sample user. For example, the at least two sample fingers include the metacarpophalangcal joints and the proximal interphalangeal joints of the index and middle fingers.

In some embodiments of the present disclosure, only sample sensor data corresponding to some of the finger joints may be obtained, making the calculation process more targeted and reducing the data amount in the calculation process.

In some embodiments, the at least two sample finger joints include all the metacarpophalangeal joints and all the proximal interphalangeal joints of the sample user. When the metacarpophalangeal joints move or deform, there may be a linkage impact on the sample sensor data of the proximal interphalangeal joints. Therefore, the processing device 410B also takes into account the coupling relationship between the metacarpophalangeal joints and the proximal interphalangcal joints when obtaining the sample sensor data. It will be appreciated that the at least two sample finger joints may be similar to the at least two target finger joints as described in FIG. 6. In some embodiments, the at least two sample finger joints are of the same type as the at least two target finger joints as described in FIG. 6. More descriptions regarding the target finger joints may be found in FIG. 6 and related descriptions thereof.

In some embodiments of the present disclosure, all the metacarpophalangeal joints and all the proximal interphalangeal joints are determined as the sample finger joints, such that there is no need to arrange sample sensors at the distal interphalangeal joints, which simplifies the structure of the sample glove system and saves the cost. In addition, the sample sensor data corresponding to the sample finger joints may be processed without data screening, thereby simplifying the processing operation. In addition, using all metacarpophalangeal joints and all proximal interphalangeal joints as sample finger joints allows the processing to take into account the coupling relationships between all metacarpophalangcal joints and all proximal interphalangeal joints, which makes the sample sensor data more complete, and a more accurate finger joint angle (e.g., the first joint angle) may be obtained using the mapping relationship (e.g., the first mapping relationship) obtained based on the sample sensor data.

The sample strain sensors include at least two strain sensors arranged at the at least two sample finger joints described above.

In some embodiments, the at least two sample strain sensors include at least two first sample strain sensors disposed at at least two metacarpophalangeal joints of the sample user. Each of the first sample strain sensors is configured to measure the deformation of the metacarpophalangeal joints in two degrees of freedom. The first sample strain sensors are the same as or similar to the first strain sensors described in FIG. 6.

In some embodiments, the at least two sample strain sensors include at least two second sample strain sensors disposed at the at least two proximal interphalangeal joints of the sample user. Each of the second sample strain sensors is configured to measure the deformation of a corresponding proximal interphalangeal joint in a single degree of freedom. The second sample strain sensors are the same as or similar to the second strain sensors described in FIG. 6.

More descriptions regarding the first strain sensor, the second strain sensor, and the degree of freedom may be found elsewhere in the present disclosure (e.g., FIG. 6 and its description).

In some embodiments, the processing device 410B may obtain the sample sensor data corresponding to the sample user in a manner similar to operation 610. For example, sample raw data collected by the sample strain sensors may be used as the sample sensor data. As another example, sample decoupled data determined based on the sample raw data may be used as the sample sensor data.

In 1920, for each set of sample sensor data, the processing device 410B may obtain an optical image of the hand of a sample user corresponding to the set of sample sensor data taken at the target moment.

The optical image of the hand refers to image data of the hand of the sample user captured when the sample user wears the glove. For example, the optical image of the hand may be an image of the hand captured when the sample user makes (accomplishes) the preset gesture (e.g., an opening action of the palm, a fist-clenching action, etc.) at the target moment. The optical image of the hand may be collected at the target moment using various types of image acquisition devices (e.g., depth cameras, etc.). It is understood that the optical image of the hand and the sample sensor data are collected at the same time. For example, the optical image of the hand may include a timestamp corresponding to the target moment, and the sample sensor data may correspond to the optical image of the hand collected at the same target moment based on the timestamp.

In some embodiments, the optical image of the hand is a two-dimensional (2D) planar image. In some embodiments, the optical image of the hand includes depth information. The depth information may reflect a three-dimensional (3D) spatial position of different position points or feature points (e.g., finger joints) of the hand of the sample user in the optical image of the hand. In some embodiments, the depth information may be used to determine distance information for different feature points in the optical image of the hand (e.g., distances between different finger joints, distances between finger joints and a camera position, etc.). In some embodiments, the depth information may be used to construct a hand model corresponding to the optical image of the hand. In some embodiments of the present disclosure, the use of the optical image of the hand including the depth information may make the hand model determined based on the optical image of the hand more realistic, which in turn may make the sample joint angles of the sample finger joints determined based on the optical image of the hand and/or the hand model more accurate.

In some embodiments, the optical image of the hand includes a single image. In some embodiments, the optical image of the hand includes a plurality of optical images of the hands at different shooting angles. The different shooting angles may be a plurality of predetermined angles. For example, with respect to the palm plane (e.g., X-plane) of the sample user, the different shooting angles may be n (e.g., 2, 4, 8) angles within a circumferential space of the palm plane. For example, a plurality of image acquisition devices may be arranged at two horizontal sides of the hand plane, at two sides vertical to the hand plane, or at other positions, to collect a plurality of optical images of the hand of the sample user collected at a plurality of shooting angles. As another example, one image acquisition device may be utilized to rotate around the hand of the sample user to collect the plurality of optical images of the hand, wherein the gesture of the sample user remains unchanged. Correspondingly, the target moment refers to a time period during which the user maintains the gesture.

It should be noted that, for the same action made by the sample user, a plurality of optical images of the hand captured at different shooting angles correspond to the same moment.

In some embodiments of the present disclosure, the use of the plurality of optical images of the hand at different shooting angles makes a hand model determined based on the optical images of the hand more closely reflect the hand movement or gestures of the sample user, such that the sample joint angle of the sample finger joint determined based on the optical images of the hand and/or the hand model may be more accurate. In some embodiments, the plurality of optical hand images captured at different shooting angles may also be scored, thereby filtering out optical images of the hand that meet the requirements. More description regarding scoring the optical image of the hand may be found in FIG. 21 and related descriptions thereof.

In 1930, the processing device 410B may determine, based on the optical image of the hand, the sample joint angles of the at least two sample finger joints of the sample user corresponding to the optical image of the hand.

In some embodiments, the processing device 410B may determine the sample joint angles of the at least two sample finger joints based on deformation information of the sample finger joints in the optical image of the hand.

The sample joint angle refers to a joint angle of the sample finger joint at the target moment. The sample joint angle is similar to the first joint angle described in operation 630 and may include angles in one or more degrees of freedom. For example, the processing device 410B may, through various types of image analysis algorithms, such as image recognition, recognize gesture information such as positions, angles, or the like, of the fingers and/or finger joints corresponding to the sample finger joint in the optical image, and determine the sample joint angle of the sample finger joint accordingly.

In some embodiments, the processing device 410B may determine the hand model based on the optical image of the hand and determine the sample joint angles of the at least two sample finger joints of the sample user based on the hand model.

The hand model is used to characterize the hand in the optical image of the hand, which may be in the form of an image model (e.g., 2D and 3D images). The hand model may reflect real gesture information of the hand of the sample user, e.g., position, bending, swinging, etc., of the fingers and/or finger joints. In some embodiments, the hand model is a 3D model. In some embodiments, the processing device 410B may generate the hand model based on the optical image of the hand using a modeling technique, such as a 3D image modeling algorithm. For example, the processing device 410B may determine spatial information (e.g., boundaries, positions of feature points, distances, etc.) of the hand of the sample user based on the depth information in the optical image of the hand and generate a 3D hand model corresponding to the optical image of the hand via the 3D image modeling algorithm. In some embodiments, the processing device 410B may adjust an initial hand model based on the optical image of the hand to obtain the hand model corresponding to the optical image of the hand. The initial hand model may be a model obtained by pre-modeling or obtained from an external platform. More descriptions regarding determining the hand model based on the initial hand model may be found in FIG. 20 and related descriptions thereof.

In some embodiments, the processing device 410B may determine the joint angle of the finger joint in the hand model as the sample joint angle. For example, the joint angle of the metacarpophalangeal joint (e.g., the metacarpophalangeal joint of the index finger) in the hand model may be determined as the sample joint angle of the corresponding sample metacarpophalangeal joint (i.e., the sample metacarpophalangeal joint corresponding to the sample index finger).

In some embodiments of the present disclosure, the hand model may be a 3D model, which better reflects the real gesture information of the hand of the sample user in the 3D space compared to the 2D optical image of the hand. Thus, the sample joint angle determined based on the hand model is more consistent with the real situation, thus making the sample joint angles more accurate. For example, when the sample finger joints in the optical image of the hand are occluded, the sample joint angle may be obtained more accurately based on the hand model. In some embodiments of the present disclosure, the hand model is generated by adjusting an initial hand model obtained by pre-modeling, and since information such as the angle and position of each finger joint in the pre-modeled initial hand model is known, the angle, position, etc. of the finger joint of the hand model may be determined quickly and accurately based on such known information, thereby improving the efficiency and accuracy of determining the sample joint angle.

In some embodiments, for each set of the at least one set of sample sensor data, before the target moment, the processing device 410B may control the terminal device to display to the sample user a hand model corresponding to the sample gesture to be imitated. Further, the processing device 410B may obtain sensor data collected by at least two sample sensors when the sample user imitates the sample gesture as the set of sample sensor data. The sample joint angles corresponding to the set of sample sensor data are further determined based on the hand model.

The sample gestures to be imitated may be various preset gestures or hand actions (e.g., fist actions, opening actions, etc.), which may be displayed to the sample user via a terminal device (e.g., a display device). The sample user may make the hand actions corresponding to the sample gestures to be imitated at the target moment.

When the gesture made by the sample user is consistent with (or similar to) the sample gesture to be imitated, which indicates that the sample user has completed the sample gesture, the sensor data collected by at least two sample sensors may be designated as the sample sensor data collected at the target moment. Further, the processing device 410B may determine the sample joint angles corresponding to the sample sensor data based on the hand model corresponding to the sample gesture.

In some embodiments, the processing device 410B may obtain sensor data collected by at least two sample sensors as sample sensor data based on user feedback information. For example, the sample user may determine whether the gesture he or she makes is consistent with the sample gesture to be imitated and input user feedback information via a terminal device (e.g., through voice, etc.). In response to receiving the user feedback information, the processing device 410B may obtain sensor data collected by the at least two sample sensors as sample sensor data. In some embodiments, the processing device 410B may obtain the optical image of the hand of the sample user, and determine, based on the optical image of the hand, whether the gesture made by the sample user is consistent with the sample gesture to be imitated. For example, the processing device 410B may determine whether a difference between the optical image of the hand and the sample gesture to be imitated (e.g., an average difference, an overall difference, etc., of the distance between each hand joint and/or finger joint in the sample gesture to be imitated and the optical image of the hand) is less than a difference threshold. In response to determining that the difference is less than the difference threshold, the processing device 410B may determine that the gesture made by the sample user is consistent with the sample gesture to be imitated. Further, the processing device 410B may designate the sensor data collected by at least two sample sensors as the sample sensor data. In some embodiments, in response to determining that a gesture made by the sample user is not consistent with the sample gesture to be imitated (e.g., the difference is greater than a difference threshold), the processing device 410B may send an alert signal to the sample user via the terminal device to remind and/or instruct the sample user to adjust his or her gesture to be consistent with the sample gesture.

According to some embodiments of the present disclosure, by instructing the sample user to intimate the sample gesture before the target moment, the sample sensor data may be collected only after the sample user intimates the sample gesture, and the sample joint angles may be determined directly based on the hand model corresponding to the sample gesture, which simplifies the complexity of determining the sample joint angles and improves the efficiency of obtaining the sample joint angles. In addition, the above approach is simple and easy to implement, and a plurality of sample gestures (hand models) may be provided for imitation by the sample users so that a plurality of pieces of sample sensor data and corresponding sample joint angles may be obtained, which in turn improves the accuracy and practicability of the mapping relationship.

In some embodiments, the processing device 410B may recognize feature points corresponding to the at least two sample finger joints from the optical image of the hand and determine sample joint angles for the at least two sample finger joints based on the feature points.

The feature points corresponding to the sample finger joints refer to a plurality of points recognized from the optical image of the hand that are located on or near the sample finger joints. For example, the feature points may include a plurality of points on the finger on which the sample finger joint is located. In some embodiments, the processing device 410B may recognize the optical image of the hand based on various types of algorithms (e.g., image recognition algorithms, machine vision algorithms, etc.) to determine the feature points corresponding to the sample finger joints, thereby determining the sample joint angles of the at least two sample finger joints based on the feature points. For example, the processing apparatus 410B may determine the bending direction of each sample finger joint and the bending magnitude of each sample finger joint based on a direction relationship or a geometrical relationship (e.g., a relative position, a direction, or the like) of feature points corresponding to each sample finger joint, thereby obtaining the sample joint angle of the sample finger joint in the degree of freedom of bending.

In some embodiments of the present disclosure, the processing process may be simplified, and the processing efficiency may be improved by recognizing the feature points corresponding to the sample finger joints from the optical image of the hand to determine the sample joint angles of at least two sample finger joints.

It is to be appreciated that the above method for determining the sample joint angles is only an exemplary illustration, and in some embodiments, the sample joint angles may be obtained by other methods. For example, the sample joint angles may be measured directly by a measuring tool (e.g., a joint ruler) and stored in a storage device (e.g., storage device 440 in FIG. 4), and the processing device 410B may obtain the sample joint angles from the storage device.

In 1940, the processing device 410B may determine a correspondence relationship between each set of sample sensor data and sample joint angles corresponding to the set of sample sensor data.

In the present disclosure, there is a correspondence relationship between a set of sample sensor data and an optical image of the hand collected at the same target moment, and there is a correspondence relationship between the set of sample sensor data and sample joint angles determined based on the optical image of the hand.

In some embodiments, process 1900 further includes operation 1950. In 1950, the processing device 410B may determine a mapping relationship between the sensor data corresponding to the at least two sample finger joints and the joint angles based on the correspondence relationship.

Since the at least two sample finger joints are of the same type as the at least two target finger joints described in FIG. 6, the mapping relationship between the sensor data corresponding to the at least two sample finger joints and the joint angles may also be referred to as a first mapping relationship between the sensor data corresponding to at least two target finger joints. For case of description, the mapping relationship determined in operation 1950 may be referred to as the first mapping relationship hereinafter. The first mapping relationship may be represented in the form of a mapping function, a machine learning model, etc. More descriptions regarding the first mapping relationship may be found in operation 620.

In some embodiments, a set of sample sensor data and sample joint angles having a correspondence relationship may form a data sample. The first mapping relationship may be determined based on a plurality of data samples. For example, when the first mapping relationship is represented by a mapping function, it may be obtained by a data-fitting algorithm based on the plurality of data samples. As another example, when the first mapping relationship is represented by a machine learning model, it may be obtained by model training based on the plurality of data samples. In the training process, the input of the training includes a plurality of sets of sample sensor data, and the training labels include sample joint angles corresponding to each set of sample sensor data.

In some embodiments, the processing device 410B may further determine a second mapping relationship (e.g., the second mapping relationship as described in FIG. 6), the second mapping relationship may reflect a relationship between the joint angle of a proximal interphalangcal joint and the joint angle of its corresponding distal interphalangeal joint. For example, the processing device 410B may obtain a sample joint angle of a proximal interphalangeal joint and a sample joint angle of a distal interphalangeal joint corresponding thereto, and determine the second mapping relationship by a data fitting algorithm or a machine learning algorithm. The second mapping relationship may be represented by a mapping function or a trained machine learning model.

In some embodiments, the processing device 410B may also determine a third mapping relationship (e.g., a third mapping relationship as described in FIG. 6), the third mapping relationship may reflect a relationship between joint angles of at least two metacarpophalangeal joints, sensor data of the at least two proximal interphalangcal joints, and joint angles of at least two proximal interphalangeal joints. For example, the processing device 410B may obtain sample joint angles of at least two sample metacarpophalangeal joints, sample sensor data of at least two proximal interphalangeal joints, and sample joint angles of at least two proximal interphalangcal joints, and determine the third mapping relationship using a data fitting algorithm or a machine learning algorithm. The third mapping relationship may be represented by a mapping function or a trained machine learning model.

More descriptions regarding the first mapping relationship, the second mapping relationship, and the third mapping relationship may be found in FIG. 6 and related descriptions thereof.

In some embodiments, the sample glove body includes sample fabric wrapped around each sample finger of the sample user and sample fabric disposed between adjacent sample fingers. The clastic modulus of the sample fabric between the adjacent sample fingers is less than the clastic modulus of the sample fabric wrapped around each sample finger. A characteristic parameter of the sample fabric between the adjacent sample fingers may affect the strength of the coupling relationship between the finger joints of the adjacent fingers. Therefore, the processing device 410B may obtain the sample value of the characteristic parameter of the sample fabric between the adjacent sample fingers. The characteristic parameter may include at least one of an elastic coefficient, a transverse dimension, and a resilience coefficient. Further, the processing device 410B may determine the first mapping relationship further based on the sample value of the characteristic parameter. The first mapping relationship may reflect a relationship between the characteristic parameter, the sensor data corresponding to the at least two sample finger joints, and the joint angles of the at least two sample finger joints.

More descriptions regarding information about the fabric between adjacent fingers and the characteristic parameter may be found in FIG. 6 and related descriptions thereof.

Merely by way of example, when the first mapping relationship is represented by a machine learning model. The training input may include the sensor data corresponding to at least two sample finger joints and a sample value of a characteristic parameter of the sample fabric between adjacent sample fingers (e.g., the elastic coefficient and the transverse dimension, etc.), and the training label may include sample joint angles corresponding to the sample sensor data. In a training process, the value of the loss function may be determined based on a difference between the output of the initial machine learning model and the training label. The parameters of the initial machine learning model may be iteratively updated based on the value of the loss function until the training ending conditions are met (e.g., the loss function converges, a specific count of iterations are performed, etc.) to obtain an updated initial machine learning model (i.e., the trained machine learning model). The trained machine learning model may be designated as the first mapping relationship.

In some embodiments of the present disclosure, when determining the mapping relationship, the influence of the characteristics of the sample fabric between adjacent sample fingers on the coupling relationship between finger joints is taken into account, which may make the mapping relationship more in line with the actual situation and the joint angle determined using the mapping relationship more accurate.

In some embodiments, the coupling relationship between the sample finger joints is related to the distance between the sample finger joints. Therefore, the mapping relationship may be further determined based on sample distance information.

In some embodiments, the sample glove body may include a sample position sensor arranged at each sample finger joint, and the processing device 410B may determine, based on the position data collected by the sample position sensor at each sample finger joint, sample distance information between at least two sample strain sensors, and further determine a first mapping relationship based on the sample distance information. The first mapping relationship may reflect a relationship between a sample distance between the at least two sample strain sensors, sensor data corresponding to the at least two sample finger joints, and the joint angles of the at least two sample finger joints.

The sample position sensor refers to a position sensor arranged at a sample finger joint, which may be configured to collect position data (i.e., sample position data) corresponding to each sample finger joint, and the sample distance characterizes the distance between two sample finger joints.

Merely by way of example, when the first mapping relationship is represented by a machine learning model, the training input may include the sample distance between the at least two sample strain sensors and the sensor data corresponding to the at least two sample finger joints. The training labels may include sample joint angles corresponding to the sample sensor data.

In some embodiments of the present disclosure, when determining the mapping relationship, the influence of the distance between the finger joints on the coupling relationship between the finger joints is taken into account, which makes the mapping relationship more in line with the actual situation and the joint angle determined using the mapping relationship more accurate.

It should be noted that the above description of the process 1900 is for illustration only and is not intended to limit the scope of the present disclosure. For those of ordinary skill in the art, a wide variety of variations and modifications may be made under the teachings of the present disclosure. However, these variations and modifications do not depart from the scope of the present disclosure. In some embodiments, the process 1900 may be accomplished with one or more additional operations not described and/or without one or more of the operations discussed above. In addition, the order of process 1900 is not limiting. For example, the process 1900 may include operations for correcting the mapping relationship. As another example, process 1900 may include an operation for determining the joint angle using the mapping relationship. As another example, process 1900 may include the operation for determining the hand model. More descriptions regarding determining the hand model may be found in FIG. 20 and its related descriptions, which may not be repeated here. As yet another example, process 1900 may further include the operation for displaying the hand model and receiving feedback on the hand model from the sample user. More descriptions regarding displaying the hand model and receiving feedback information on the hand model from the sample user may be found in FIG. 22 and its related descriptions, which will not be repeated here. As yet another example, the process 1900 may further include the operation for scoring and filtering the optical images of the hand. More descriptions regarding scoring and filtering the optical images of the hand may be found in FIG. 21 and its related descriptions, which are not repeated here.

Figure 20:
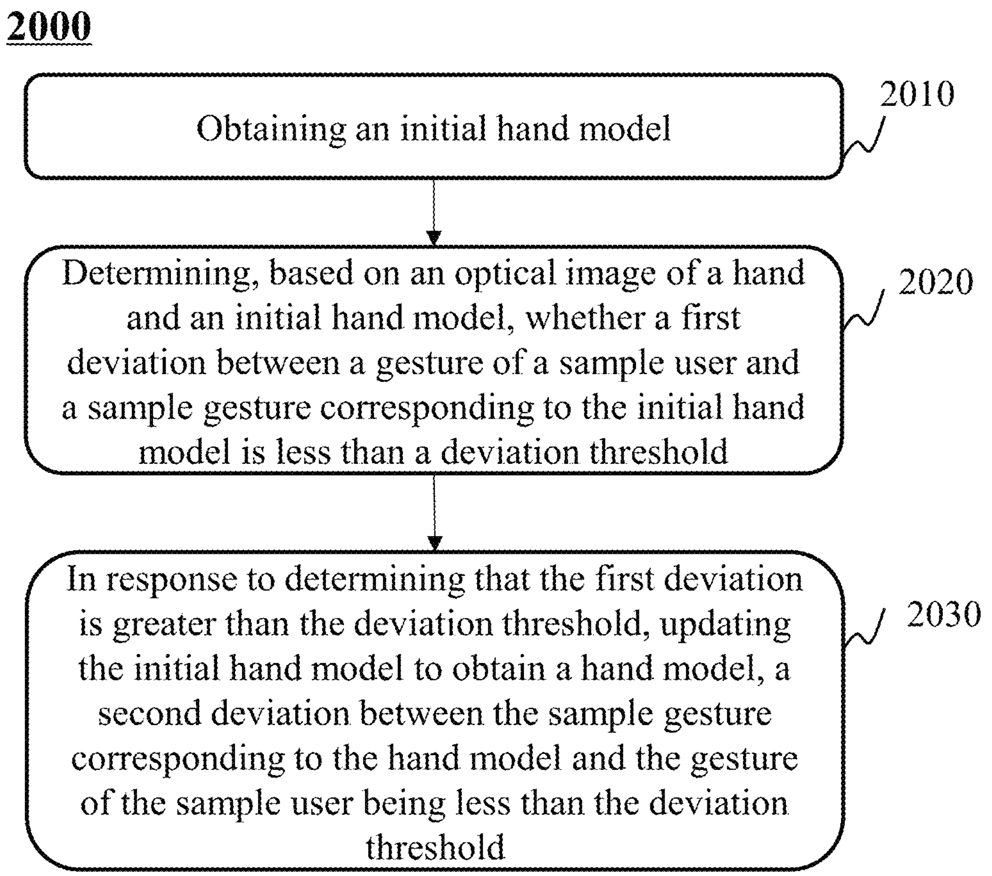
FIG. 20 is a flowchart illustrating an exemplary process for determining a hand model according to some embodiments of the present disclosure.

FIG. 20 is a flowchart illustrating an exemplary process for determining a hand model according to some embodiments of the present disclosure. In some embodiments, the process 2000 may be performed by the processing device 410B. In some embodiments, at least a portion of operation 1930 in process 1900 (e.g., determining the hand model based on the optical image of the hand) may be realized by process 2000. As shown in FIG. 20, the process 2000 may include the following operations.

In 2010, the processing device 410B may obtain an initial hand model.

The initial hand model may be a hand model obtained by pre-modeling or obtained from an external platform. For example, the processing device 410B may use various types of image modeling techniques to generate an initial hand model based on a plurality of pre-collected hand data and/or images (e.g., the optical image of the hand) of any user. For example, the processing device 410B may obtain the initial hand model from the external platform, and the initial hand model may be obtained by modeling based on a plurality of pieces of hand data and/or a plurality of images of any user. In some embodiments, the initial hand model may be a 3D model (e.g., a 3D image model), or a hand frame model including a plurality of points and/or lines including generic features of a hand (e.g., palm size, length of fingers, texture, etc.) as well as posture information about the hand (e.g., the bending angles of the fingers and/or finger joints, etc.). In some embodiments, the initial hand model may be presented on the terminal device and may be adjusted (e.g., positions, shapes, etc., of fingers and/or finger joints may be adjusted) to generate a hand model consistent with gestures made by the sample user.

In some embodiments, the initial hand model may include a generic hand model. The generic hand model is a pre-set base hand model, which may be a hand model generated based on a hand action (e.g., an arbitrary hand action). The processing device 410B may obtain the generic hand model from a storage device.

In some embodiments, the initial hand model may further include a specialized hand model. The specialized hand model is a hand model that is pre-set based on different preset gestures or actions. For example, the specialized hand model may include a fist-clenching hand model corresponding to a fist-clenching action, a stretching hand model corresponding to a closing and stretching action, an opening hand model corresponding to an opening action, or the likc.

In some embodiments, the specialized hand model may also include a plurality of hand models preset for different users and/or groups of users at different preset gestures or actions. For example, a fist-clenching hand model for males/females, a stretching hand model for the elderly/children, or the like.

In some embodiments, the processing device 410B may recognize the optical image of the hand and retrieve or match a target specialized hand model from a plurality of specific hand models as the initial hand model. The target specialized hand model corresponds to a hand action that has the highest degree of similarity to a gesture of the sample user in the optical image of the hand.

In some embodiments of the present disclosure, through the specialized hand model, the workload of updating the initial hand model may be reduced, thereby improving the efficiency of adjusting or updating the initial hand model through the optical image of the hand and reducing the computational resource loss.

In some embodiments, the initial hand model may be generated using a generator in a trained generative adversarial network (GAN). For example, the processing device 410B may input the optical images of the hand from a plurality of angles into the trained GAN model, and the generator of the trained GAN model outputs the initial hand model.

In some embodiments, an initial GAN model may be trained based on a plurality of sets of training samples to obtain a trained generator and a trained discriminator. The plurality of sets of training samples may include a plurality of sets of sample optical images of the hand and sample hand models corresponding to the sample optical images of the hand. Each set of sample optical images of the hand and the corresponding sample hand model may be obtained when the sample user makes the same gesture. A plurality of sample hand models (or real samples) may be constructed as real datasets.

In the training process, the plurality of sets of sample optical images of the hand may be input to the initial generator, respectively, and the initial generator outputs a plurality of intermediate hand models. The initial discriminator discriminates the authenticity of the plurality of intermediate hand models and the corresponding sample hand models. A value of the loss function may be determined based on differences between the intermediate hand models and the sample hand models and/or discrimination results of the initial discriminator. Accordingly, parameters of the initial generator and/or the initial discriminator are iteratively updated to enable the initial discriminator to generate a hand model that is as close as possible to the sample hand model and sufficient to confound the initial discriminator, while the initial discriminator is capable of accurately performing authenticity discrimination. The initial generator and initial discriminator may be trained alternately or together.

The trained generator may be configured to output a hand model based on the optical image of the hand. The hand model output by the trained generator may be designated as the initial hand model.

In 2020, the processing device 410B may determine, based on the optical image of the hand and the initial hand model, whether a first deviation between a gesture of the sample user and a sample gesture corresponding to the initial hand model is less than a deviation threshold.

The sample gesture refers to the hand action corresponding to the initial hand model. The gesture of the sample user refers to the current hand action (or current gesture or user gesture) of the sample user of the optical image of the hand. In some embodiments, gestures (e.g., the sample gestures and the user gesture) may be represented in the form of gesture vectors. The gesture vectors may be generated based on a plurality of hand features. The hand features include features of the fingers in the gesture (e.g., length, width, thickness), features of the finger joints (e.g., spatial position distribution, bending angles), and features of the hand feature points (e.g., positions, distances between a plurality of hand feature points, etc.). In some embodiments, the gestures may be represented by hand feature points and connection lines connecting the hand feature points. For example, the hand feature points may include a plurality of points corresponding to positions such as wrist joints, finger joints, fingertips, etc., and the processing device 410B may determine positions of the sample gesture and positions of the user gesture in the same coordinate system (e.g., a 3D coordinate system) and determine connection lines of the adjacent feature points in each gesture, and further obtain gesture representations of the sample gesture and the user gesture in the coordinate system, respectively.

The first deviation refers to the difference between the gesture of the sample user (i.e., the user gesture) and the sample gesture, which may also be referred to as the overall deviation between the user gesture and the sample gesture. For example, the first deviation may be a difference (e.g., a vector distance) between gesture vectors, a difference (a distance) between feature points, a difference between joint angles, etc. The first deviation may be expressed in various forms, for example, in the form of a numerical value, where a larger value indicates a larger difference.

In some embodiments, the processing device 410B may determine a vector distance between a gesture vector corresponding to the sample gesture and a gesture vector corresponding to the user gesture based on various vector distance algorithms (e.g., a Euclidean distance, a cosine distance, etc.) and determine a value of the first deviation based on the vector distance. The smaller the value of the first deviation, the more similar the sample gesture is to the user gesture, i.e., the smaller the first deviation. In some embodiments, the processing device 410B may determine the first deviation based on a distance between corresponding hand feature points in the sample gesture and the user gesture. The corresponding hand feature points refer to feature points in the sample gesture and the user gesture that correspond to the same hand position (e.g., the tip of the index finger).

In some embodiments, the value of the first deviation may be a statistical value (e.g., a sum, an average, etc.) of the differences in the plurality of hand features. For example, the first deviation may be an average or sum of distances between each hand feature point in the sample gesture and the corresponding hand feature point in the user gesture.

The processing device 410B may further determine whether the first deviation between the sample gesture and the user gesture is less than the deviation threshold. The deviation threshold may be predetermined.

In 2030, in response to determining that the first deviation is greater than the deviation threshold, the processing device 410B may update the initial hand model to obtain a hand model. A second deviation between the sample gesture corresponding to the hand model and the gesture of the sample user is less than the deviation threshold.

In some embodiments, the processing device 410B may perform a model update process on the initial hand model. The model update process refers to one or more rounds of adjustment or fitting of the initial hand model such that the sample gesture is adjusted in the direction that gradually approaches (or is similar to) the user gesture, thus obtaining an updated hand model. A deviation (or second deviation) between the sample gesture in the updated hand model and the user gesture may be less than the deviation threshold.

In some embodiments, the model update process includes adjusting one or more hand features (or feature points) corresponding to the sample gesture. For example, the processing device 410B may adjust the position and/or angle of the finger joints in the sample gesture by performing operations such as translating, rotating, etc., the position of a portion or a plurality of voxel points in the initial hand model, thereby making the position and/or angle of the finger joint in the sample gesture corresponding to the updated initial hand model (i.e., the updated hand model) close to the position and/or angle of the finger joint in the user gesture.

In some embodiments, in order to update the initial hand model, the processing device 410B may sequentially adjust the joint angles of the thumb, the index finger, the middle finger, the ring finger, and the pinky finger in the initial hand model. After each adjustment of the joint angle, the processing device 410B may determine whether the deviation (also referred to as a third deviation) between the sample gesture corresponding to the adjusted hand model and the gesture of the sample user is less than a deviation threshold. In response to determining that the third deviation is less than or equal to the deviation threshold, the adjustment of the other fingers is stopped, and the adjusted hand model is designated as the updated hand model. In response to determining that the third deviation is greater than the deviation threshold, the processing device 410B may continue to perform the adjustment on the other fingers to adjust the joint angles of the other fingers.

In some embodiments of the present disclosure, by sequentially adjusting the fingers in the initial hand model and stopping the adjustment of the other fingers after determining that the third deviation is less than or equal to the deviation threshold, the adjustment operation may be simplified under the condition of ensuring that the sample gesture in the updated hand model is consistent with the user gesture, thereby improving the adjustment efficiency.

In some embodiments, in order to update the initial hand model, for each finger of the sample user, the processing device 410B may determine whether a deviation (also referred to as a fourth deviation or a localized deviation) between the finger and a corresponding finger in the initial hand model is less than a second deviation threshold. In response to determining that the fourth deviation is greater than the second deviation threshold, the finger is adjusted. In response to determining that the fourth deviation is less than or equal to the second deviation threshold, the processing device 410B may determine that the finger doesn't need to be adjusted.

The fourth deviation refers to a difference between the sample gesture and the user gesture for a particular finger, for example, the difference between gesture vectors corresponding to the finger (e.g., the vector distance), the difference (the distance) between the feature points on the finger, and the difference between the joint angles of the finger. For example, taking the index finger as an example, the value of the fourth deviation is used to reflect the difference between the angle of the metacarpophalangeal joint of the index finger of the sample gesture and the angle of the metacarpophalangeal joint of the index finger of the user gesture.

The second deviation threshold refers to a threshold relating to the difference between the sample gesture and the user gesture in each finger. In some embodiments, second deviation thresholds corresponding to different fingers may be the same, which may simplify the calculation process. In some embodiments, the second deviation thresholds corresponding to different fingers may be different, so that corresponding deviation thresholds may be set according to the characteristics of different fingers, which makes the adjustment process more targeted and makes the adjustment results more accurate. In some embodiments, the second deviation threshold is smaller than the first deviation threshold.

In some embodiments of the present disclosure, by updating each finger and/or finger joint, a full update of each finger may be realized, so that the gesture between each finger in the sample gesture and the user gesture is consistent (less than the second deviation threshold), which makes the adjustment result more accurate.

In some embodiments of the present disclosure, a two-way optical recognition and adjustment of the hand model is realized by using the hand model and the optical image, so that, on the one hand, the sample joint angles may be obtained from the hand model that contains more posture information, making the sample joint angles more accurate; on the other hand, the initial hand model is generated in advance and only needs to be adjusted appropriately according to the optical image, which provides a plurality of data sets corresponding to the joint angles quickly, thus improving the accuracy and usefulness of the mapping relationship.

Figure 21:
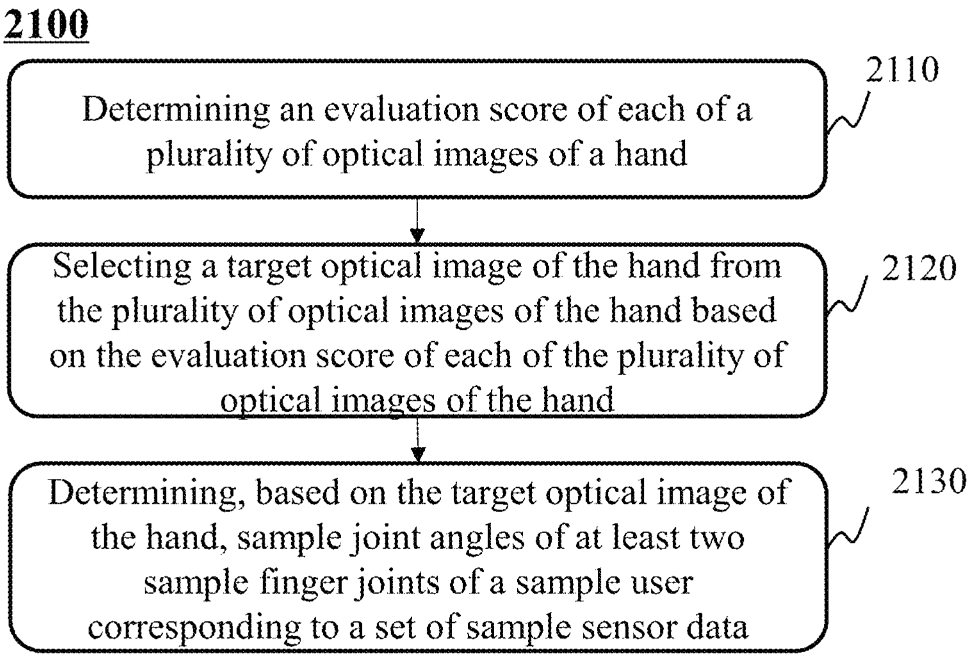
FIG. 21 is a flowchart illustrating an exemplary process for determining a sample joint angle according to some embodiments of the present disclosure.

FIG. 21 is a flowchart illustrating an exemplary process for determining a sample joint angle according to some embodiments of the present disclosure. In some embodiments, process 2100 may be performed by the processing device 410B. In some embodiments, operation 1930 in process 1900 may be realized by process 2100. As shown in FIG. 21, process 2100 may include the following operations.

In some embodiments, the optical image of the hand may include a plurality of optical images of the hand at different shooting angles. For example, the optical image of the hand may be a plurality of optical images of the hand captured by different shooting angles at a target moment.

In 2110, the processing device 410B may determine an evaluation score of each of the plurality of optical images of the hand.

The sample user may have different hand postures, positions of different fingers, etc. when making different gestures. The optical image of the hand captured at a certain shooting angle may have some of the finger joints obscured, etc. Thus, a plurality of optical images of the hand may be captured at different shooting angles and the evaluation score of each optical image of the hand may be determined, such that optical images meet the requirements may be selected from the plurality of optical images. The evaluation score may be used to assess the quality of the optical image of the hand (e.g., how much hand information is included), which may be expressed in the form of a numerical value (e.g., a numerical value in the interval [0,10]), with a larger value indicating a better quality and the more likely to be designated as a target optical image of the hand.

In some embodiments, the evaluation score is related to an occlusion degree of one or more sample finger joints in the optical image of the hand. The occlusion degree of a sample finger joint may reflect whether or not the sample finger joint is completely visible. For example, if a sample finger joint (e.g., the metacarpophalangeal joint or interphalangcal joint corresponding to the middle finger of the sample, etc.) is not visible in a certain optical image of the hand at a certain shooting angle, the occlusion degree of the sample finger joint is high, and correspondingly, the evaluation score of the optical image of the hand is low.

In some embodiments, the processing device 410B may obtain a plurality of optical images of the hand at different shooting angles and evaluate each optical image of the hand separately to determine the occlusion degree of one or more of the sample finger joints, thereby obtaining an evaluation score of each optical image of the hand.

In some embodiments, the evaluation score may also be related to other evaluation metrics. For example, exemplary evaluation metrics may include, but are not limited to, signal-to-noise ratios, clarity, or the like of the optical image of the hand. For example, the higher the signal-to-noise ratio and the higher the clarity of the optical image of the hand, the higher the evaluation score.

In some embodiments, the processing device 410B may determine the evaluation score of each optical image of the hand based on a trained scoring model. The scoring model may be a convolutional neural network (CNN) model or other deep neural network models. An input of the scoring model includes the optical image of the hand, and an output of the scoring model includes the evaluation score corresponding to the optical image of the hand. In some embodiments, an initial scoring model may be trained iteratively using supervised learning to obtain a trained scoring model. Training samples of the initial scoring model may include historically collected sample optical images of the hand (e.g., a plurality of sample optical images of the hand at different sample shooting angles), and a label of each training sample is an evaluation score corresponding to the sample optical image of the hand, which may be labeled manually or by other feasible means.

In 2120, the processing device 410B may select a target optical image of the hand from the plurality of optical images of the hand based on the evaluation score of each of the plurality of optical images of the hand.

The target optical image of the hand is an optical image of the hand that is filtered from a plurality of optical images of the hand for subsequent processing. In some embodiments, the processing device 410B may determine the evaluation score of each optical image of the hand separately and designate an optical image of the hand with the top-ranked evaluation score (e.g., the highest evaluation score) as the target optical image of the hand. In some embodiments, there may be one or more target optical images of the hand.

In 2130, the processing device 410B may determine, based on the target optical image of the hand, the sample joint angles of at least two sample finger joints of a corresponding sample user.

Determining the sample joint angles based on the target optical image of the hand is similar to the process of determining the sample joint angles of the sample finger joint based on the optical image of the hand as described in operation 1930, which is not described herein.

In some embodiments of the present disclosure, by selecting a suitable (e.g., with the highest evaluation score) optical image of the hand for the determination of the sample joint angles of the sample finger joint, the results of the subsequent determination of the sample joint angles may be more accurate, which may improve the efficiency of the calculation.

Figure 22:
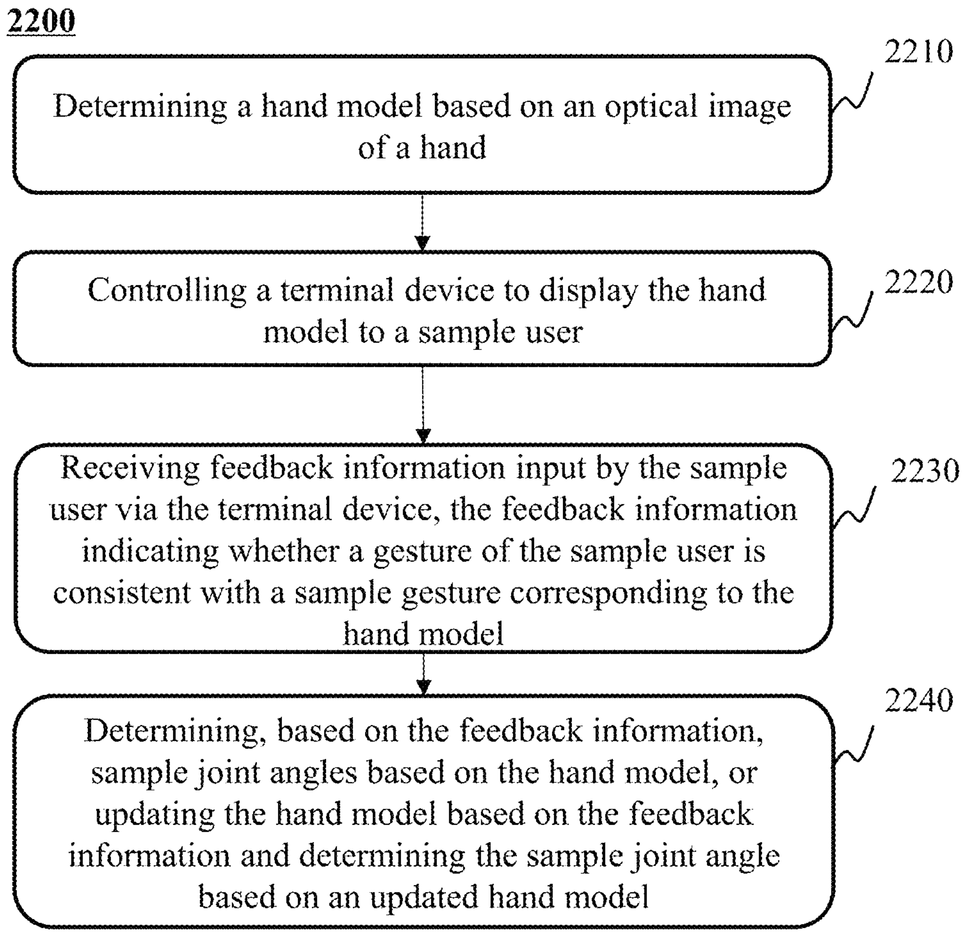
FIG. 22 is a flowchart illustrating another exemplary process for determining a sample joint angle according to some embodiments of the present disclosure.

FIG. 22 is a flowchart illustrating another exemplary process for determining a sample joint angle according to some embodiments of the present disclosure. In some embodiments, process 2200 may be performed by the processing device 410B. In some embodiments, operation 1930 in process 1900 may be realized by process 2200. As shown in FIG. 22, process 2200 may include the following operations.

In 2210, the processing device 410B may determine the hand model based on the optical image of the hand.

For example, the processing device 410B may obtain an initial hand model and determine, based on the optical image of the hand and the initial hand model, whether a first deviation between the gesture of the sample user and a sample gesture corresponding to the initial hand model is less than a deviation threshold, and update the initial hand model based on the determination result, thereby determining the hand model. Descriptions regarding the hand model and the determination of the hand model based on the optical image of the hand may be found in FIG. 20 and related description thereof, which will not be repeated here.

In 2220, the processing device 410B may control a terminal device to display the hand model to the sample user.

For example, the processing device 410B may control the terminal device (e.g., the terminal 430 shown in FIG. 1) to display the hand model. The sample user may determine, based on the displayed hand model, whether her/his gestures are consistent with the sample gesture corresponding to the hand model. In some embodiments, the processing device 410B may also control the terminal device to display the sample user's gestures to the sample user. For example, the gesture and the hand model of the sample user may be represented in the form of images or feature points and connection lines connecting the feature points, etc. The processing device 410B may control the terminal device to simultaneously display the gesture of the sample user and the sample gesture corresponding to the hand model. The sample user may determine whether the gesture of the sample user is consistent with the sample gesture corresponding to the hand model based on the displayed hand model and the displayed gesture of the sample user.

In 2230, the processing device 410B may receive feedback information input by the sample user via the terminal device. The feedback information indicates whether the gesture of the sample user is consistent with the sample gesture corresponding to the hand model.

The feedback information includes feedback information from the sample user on the consistency of the gesture made by the sample user (i.e., user gesture) with the sample gesture, which may include but is not limited to, one or a combination of various forms, such as voice, text, or the like.

For example, the feedback information may indicate that the gesture of the sample user is consistent (or inconsistent) with the sample gesture corresponding to the hand model. In some embodiments, the feedback information may also include information related to the consistency of all or a portion of the fingers and/or finger joints of the user gesture. For example, when the gesture of the sample user is inconsistent with the sample gesture corresponding to the hand model, the feedback information may specifically indicate that the bending angles of the index fingers are inconsistent, the included angles between the thumbs and the index fingers are inconsistent, etc. and/or an adjustment instruction for adjusting the hand model.

In 2240, based on the feedback information, the processing device 410B may determine the sample joint angles based on the hand model, or update the hand model and determine the sample joint angles based on the updated hand model.

For example, if the feedback information indicates that the gesture of the sample user is consistent with the sample gesture corresponding to the hand model, the processing device 410B may determine the sample joint angles directly based on the hand model. If the feedback information indicates that the gesture of the sample user is inconsistent with the hand model corresponding sample gesture, the processing device 410B may update the hand model and determine the sample joint angles based on the updated hand model.

In some embodiments, the terminal device may include an interactive interface for adjusting the sample gesture. For example, the sample user (or other users) may adjust the bending angles of one or more fingers (e.g., the index finger, the middle finger, etc.) via the interaction interface to make the sample gesture displayed by the terminal device consistent with the posture (e.g., positions, bending angles, etc.) of the fingers in the user gesture.

In some embodiments, the processing device 410B may also automatically update the hand model displayed by the terminal device based on the feedback information to obtain a hand model consistent with the user gesture. For example, the processing device 410B may perform an automatic update of the hand model based on the method described in operations 2020-2030 of process 2000. As another example, the processing device 410B may process the feedback information based on techniques such as speech recognition, text recognition, or the like, to determine an adjustment instruction for updating the hand model. The adjustment instruction may be used to adjust the hand features of the sample gesture, for example, position adjustment (e.g., translation) and posture adjustment (e.g., the magnitude, the direction, etc. of bending) of the fingers and/or finger joints in the hand model. The processing device 410B may further determine the sample joint angles based on the automatically updated hand model.

In some embodiments of the present disclosure, the hand model is adjusted through the feedback information of the sample user, which further improves the compliance of the hand model, thus improving the accuracy of the determined sample joint angles.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and amendments are intended to be suggested by this disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment", "one embodiment", or "an alternative embodiment" in various portions of the present disclosure are not necessarily all referring to the same embodiment. In addition, some features, structures, or characteristics of one or more embodiments in the present disclosure may be properly combined.

Furthermore, the recited order of processing elements or sequences, or the use of numbers, letters, or other designations, therefore, is not intended to limit the claimed processes and methods to any order except as may be specified in the claims. Although the above disclosure discusses some embodiments of the invention currently considered useful by various examples, it should be understood that such details are for illustrative purposes only, and the additional claims are not limited to the disclosed embodiments. Instead, the claims are intended to cover all combinations of corrections and equivalents consistent with the substance and scope of the embodiments of the present disclosure. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that object of the present disclosure requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially," For example, "about," "approximate," or "substantially," may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes. History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for determining a finger joint angle, comprising:

obtaining first sensor data relating to at least two target finger joints of a user, wherein the first sensor data is obtained using at least two strain sensors, each of the strain sensors is arranged in a glove body worn by the user and located at one of the at least two target finger joints, the at least two target finger joints include at least two adjacent metacarpophalangeal joints of the user and at least two proximal interphalangeal joints corresponding to the at least two metacarpophalangeal joints, and the at least two strain sensors include at least two first strain sensors disposed at the at least two metacarpophalangeal joints and second strain sensors disposed at the at least two proximal interphalangeal joints, each of the at least two first strain sensors being configured to measure a deformation of a corresponding metacarpophalangeal joint in two degrees of freedom, each of the second strain sensors being configured to measure a deformation of the corresponding proximal interphalangeal joint in a single degree of freedom;

obtaining a first mapping relationship, wherein the first mapping relationship reflects a relationship between sensor data corresponding to the at least two target finger joints and joint angles of the at least two target finger joints;

determining a first joint angle of each of the at least two target finger joints based on the first sensor data and the first mapping relationship; and for each proximal interphalangeal joint among the at least two proximal interphalangeal joints, determining, based on a second mapping relationship and the first joint angle of the proximal interphalangeal joint, a second joint angle of a distal interphalangeal joint corresponding to the proximal interphalangeal joint, wherein the second mapping relationship reflects a relationship between a joint angle of the proximal interphalangeal joint and a joint angle of the distal interphalangeal joint.

2. The method of claim 1, wherein the at least two metacarpophalangeal joints include metacarpophalangeal joints of at least one finger of the index finger, the middle finger, or the ring finger of the user and two adjacent fingers on two sides of the at least one finger.

3. The method of claim 1, wherein the at least two metacarpophalangeal joints include metacarpophalangeal joints of at least one finger of the thumb or the pinky thumb of the user and one adjacent finger of the at least one finger.

4. The method of claim 1, wherein the at least two strain sensors include at least two second strain sensors disposed at the at least two proximal interphalangeal joints, each of the second strain sensors being configured to measure a deformation of a corresponding proximal interphalangeal joint in a single degree of freedom.

5. The method of claim 1, wherein the first sensor data includes decoupling data of the at least two target finger joints, the decoupling data being determined based on raw data collected by the at least two strain sensors.

6. The method of claim 1, wherein the determining a first joint angle of each of the at least two target finger joints based on the first sensor data and the first mapping relationship includes:

obtaining reference sensor data relating to the at least two target finger joints of the user, the reference sensor data being collected using the at least two strain sensors when the user makes a preset gesture;

obtaining a corrected mapping relationship corresponding to the user by correcting the first mapping relationship based on the reference sensor data; and determining the first joint angle of each of the at least two target finger joints based on the corrected mapping relationship and the first sensor data.

7. The method of claim 6, wherein the first mapping relationship is represented by a trained machine learning model, and the first mapping relationship is corrected based on a migration learning algorithm.

8. The method of claim 1, wherein the glove body includes fabric wrapped around each finger of the user and fabric disposed between adjacent fingers, an elastic modulus of the fabric disposed between the adjacent fingers is less than an elastic modulus of the fabric wrapped around each finger, the method further comprises obtaining a value of a characteristic parameter of the fabric disposed between the adjacent fingers, the characteristic parameter including at least one of an elastic coefficient, a transverse dimension, or a resilience coefficient, the first mapping relationship further reflects a relationship between the characteristic parameter, the sensor data corresponding to the at least two target finger joints, and the joint angles of the at least two target finger joints, and the first joint angle of each of the at least two target finger joints is further determined based on the value of the characteristic parameter.

9. The method of claim 1, wherein the glove body includes a position sensor arranged at each of the at least two target finger joints, the method further comprises determining distance information between the at least two strain sensors based on position data collected by the position sensor arranged at each of the at least two target finger joints, the first mapping relationship further reflects a relationship between a distance between the at least two strain sensors, the sensor data corresponding to the at least two target finger joints, and the joint angles of the at least two target finger joints, and the first joint angle of each of the at least two target finger joints is further determined based on the distance information.

10. The method of claim 1, wherein the first mapping relationship is determined by:

obtaining a plurality of data samples, each of the plurality of data samples corresponding to a sample user making a sample gesture and including sample sensor data relating to at least two sample finger joints of the sample user and sample joint angles of the at least two sample finger joints, the sample sensor data being collected using at least two sample sensors arranged in a sample glove body worn by the sample user, and the at least two sample finger joints being of the same type as the at least two target finger joints; and determining, based on the plurality of data samples, the first mapping relationship based on a data fitting algorithm or a machine learning algorithm.

11. The method of claim 10, wherein at least one data sample of the plurality of data samples is obtained by:

for each data sample of the at least one data sample, obtaining sensor data collected by the at least two sample sensors when the sample user makes the sample gesture as the sample sensor data of the data sample;

obtaining an optical image of a hand captured when the sample user makes the sample gesture; and determining the sample joint angles of the data sample based on the optical image of the hand.

12. The method of claim 10, wherein at least one of the plurality of data samples is obtained by:

for each data sample of at least one data sample, controlling a terminal device to display a hand model corresponding to the sample gesture to the sample user corresponding to the data sample;

obtaining sensor data collected by the at least two sample sensors when the sample user imitates the sample gesture as the sample sensor data of the data sample; and determining the sample joint angles of the data sample based on the hand model.

13. The method of claim 12, wherein the obtaining sensor data collected by the at least two sample sensors when the sample user imitates the sample gesture as the sample sensor data of the data sample includes:

obtaining an optical image of a hand of the sample user captured when the sample user imitates the sample gesture;

determining, based on the optical image of the hand, whether a gesture of the sample user is the sample gesture; and in response to determining that the gesture of the sample user is the sample gesture, obtaining sensor data currently collected by the at least two sample sensors as the sample sensor data; or in response to determining that the gesture of the sample user is not the sample gesture, controlling the terminal device to display an alert message for adjusting the gesture to the sample user.

14. The method of claim 1, wherein the first mapping relationship is represented by a mapping function, the glove body includes a position sensor arranged at each of the at least two target finger joints, and the determining a first joint angle of each of the at least two target finger joints based on the first sensor data and the first mapping relationship includes:

determining distance information between the at least two strain sensors based on position data captured by the position sensor arranged at each of the at least two target finger joints;

obtaining a corrected mapping function corresponding to the user by correcting the mapping function based on the distance information; and determining the first joint angle of each of the at least two target finger joints based on the corrected mapping function and the first sensor data.

15. The method of claim 1, wherein the second mapping relationship is represented by a mapping function or a trained machine learning model.

16. A method for determining a finger joint angle, comprising:

obtaining first sensor data relating to at least two adjacent metacarpophalangeal joints of a user and second sensor data relating to at least two proximal interphalangeal joints corresponding to the at least two adjacent metacarpophalangeal joints;

determining a first joint angle of each of the at least two adjacent metacarpophalangeal joints based on the first sensor data and a first mapping relationship, wherein the first mapping relationship reflects a relationship between sensor data corresponding to the at least two adjacent metacarpophalangeal joints and joint angles of the at least two adjacent metacarpophalangeal joints; and determining a third joint angle of each of the at least two proximal interphalangeal joints based on the second sensor data, the first joint angle of each of the at least two adjacent metacarpophalangeal joints, and a third mapping relationship, wherein the third mapping relationship reflects a relationship between joint angles of the at least two adjacent metacarpophalangeal joints, sensor data relating to the at least two proximal interphalangeal joints, and joint angles of the at least two proximal interphalangeal joints.

17. The method of claim 16, wherein the first sensor data is obtained using at least two first strain sensors, each of the first strain sensors is arranged in a glove body worn by the user and located at one of the at least two adjacent metacarpophalangeal joints, the second sensor data is obtained using at least two second strain sensors, each of the second strain sensors is arranged in the glove body and located at one of the at least two proximal interphalangeal joints.

18. The method of claim 17, wherein each of the at least two first strain sensors is configured to measure a deformation of a corresponding metacarpophalangeal joint in two degrees of freedom, and each of the second strain sensors is configured to measure a deformation of the corresponding proximal interphalangeal joint in a single degree of freedom.

* * * * *